(12) United States Patent
Rothberg et al.

(10) Patent No.: US 12,076,189 B2
(45) Date of Patent: Sep. 3, 2024

(54) ULTRASONIC IMAGING DEVICES, SYSTEMS AND METHODS

(71) Applicant: BFLY Operations, Inc., Guilford, CT (US)

(72) Inventors: Jonathan M. Rothberg, Miami Beach, FL (US); Keith G. Fife, Palo Alto, CA (US); Tyler S. Ralston, Clinton, CT (US); Gregory L. Charvat, Guilford, CT (US); Nevada J. Sanchez, Guilford, CT (US)

(73) Assignee: BFLY OPERATIONS, INC, Burlington, MA (US)

( * ) Notice: Subject to any disclaimer, the term of this patent is extended or adjusted under 35 U.S.C. 154(b) by 0 days.

(21) Appl. No.: 17/890,985

(22) Filed: Aug. 18, 2022

(65) Prior Publication Data
US 2023/0079579 A1 Mar. 16, 2023

Related U.S. Application Data

(60) Continuation of application No. 15/638,331, filed on Jun. 29, 2017, now Pat. No. 11,439,364, which is a
(Continued)

(51) Int. Cl.
*A61B 8/00* (2006.01)
*A61B 8/14* (2006.01)
(Continued)

(52) U.S. Cl.
CPC .............. *A61B 8/4494* (2013.01); *A61B 8/14* (2013.01); *A61B 8/145* (2013.01); *A61B 8/4483* (2013.01); *A61B 8/4488* (2013.01); *A61B 8/54* (2013.01); *A61N 7/00* (2013.01); *A61N 7/02* (2013.01); *B06B 1/02* (2013.01); *B81C 1/00246* (2013.01); *G01S 7/52019* (2013.01);
(Continued)

(58) Field of Classification Search
CPC ......... A61B 8/14; A61B 8/145; A61B 8/4483; A61B 8/4488; A61B 8/4494; A61B 8/485; A61B 8/54; A61N 7/00; A61N 7/02; B06B 1/02; B81C 1/00246; G01S 15/02; G01S 15/8915; G01S 15/8977; G01S 7/52019; G01S 7/52034; G01S 7/52047; G01S 7/5208; H04R 1/00
See application file for complete search history.

(56) References Cited

U.S. PATENT DOCUMENTS

| | | | |
|---|---|---|---|
| 6,880,137 B1 * | 4/2005 | Burlison | G01R 31/318547 714/724 |
| 11,439,364 B2 * | 9/2022 | Rothberg | A61N 7/00 |
| 2011/0060225 A1 * | 3/2011 | Cogan | B06B 1/0207 600/459 |

* cited by examiner

Primary Examiner — Michael T Rozanski
(74) Attorney, Agent, or Firm — Boston & Galway

(57) ABSTRACT

A hand-held ultrasound device, for placement on a subject, includes a semiconductor device and a housing to support the semiconductor device. The semiconductor device includes: a plurality of ultrasonic transducer elements; a plurality of pulsers coupled to the plurality of ultrasonic transducer elements; a plurality of waveform generators configured to drive the plurality of pulsers; receive processing circuitry configured to process ultrasound signals received by the plurality of ultrasonic transducer elements; and a plurality of independently controllable registers configured to store a plurality of different parameters for the waveform generators.

20 Claims, 45 Drawing Sheets

Related U.S. Application Data continuation of application No. 15/143,369, filed on Apr. 29, 2016, now abandoned, which is a division of application No. 14/208,281, filed on Mar. 13, 2014, now Pat. No. 9,521,991.

(60) Provisional application No. 61/798,851, filed on Mar. 15, 2013.

(51) Int. Cl.
| | |
|---|---|
| *A61N 7/00* | (2006.01) |
| *A61N 7/02* | (2006.01) |
| *B06B 1/02* | (2006.01) |
| *B81C 1/00* | (2006.01) |
| *G01S 7/52* | (2006.01) |
| *G01S 15/02* | (2006.01) |
| *G01S 15/89* | (2006.01) |
| *H04R 1/00* | (2006.01) |
| *A61B 8/08* | (2006.01) |

(52) U.S. Cl.
CPC ...... *G01S 7/52034* (2013.01); *G01S 7/52047* (2013.01); *G01S 7/5208* (2013.01); *G01S 15/02* (2013.01); *G01S 15/8915* (2013.01); *G01S 15/8977* (2013.01); *H04R 1/00* (2013.01); *A61B 8/485* (2013.01)

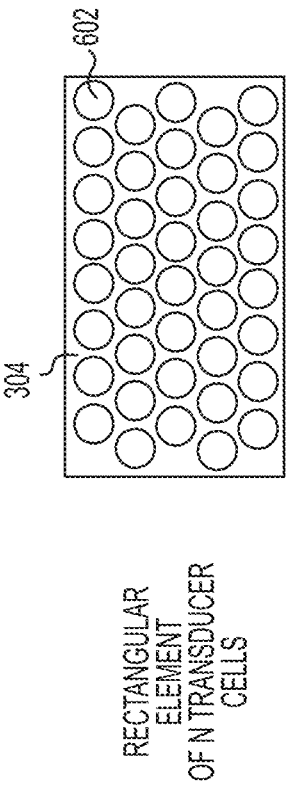
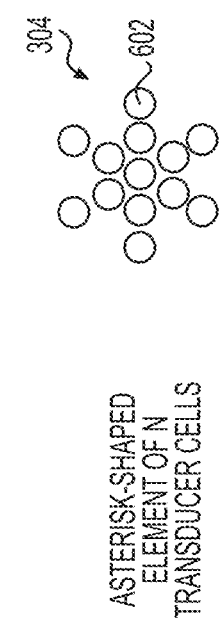
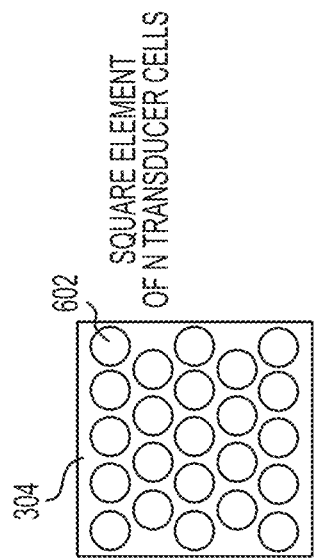
FIG. 6A  SINGLE TRANSDUCER CELL
FIG. 6B  CIRCULAR ELEMENT OF N TRANSDUCER CELLS
FIG. 6C  ASTERISK-SHAPED ELEMENT OF N TRANSDUCER CELLS
FIG. 6D  SQUARE ELEMENT OF N TRANSDUCER CELLS
FIG. 6E  RECTANGULAR ELEMENT OF N TRANSDUCER CELLS

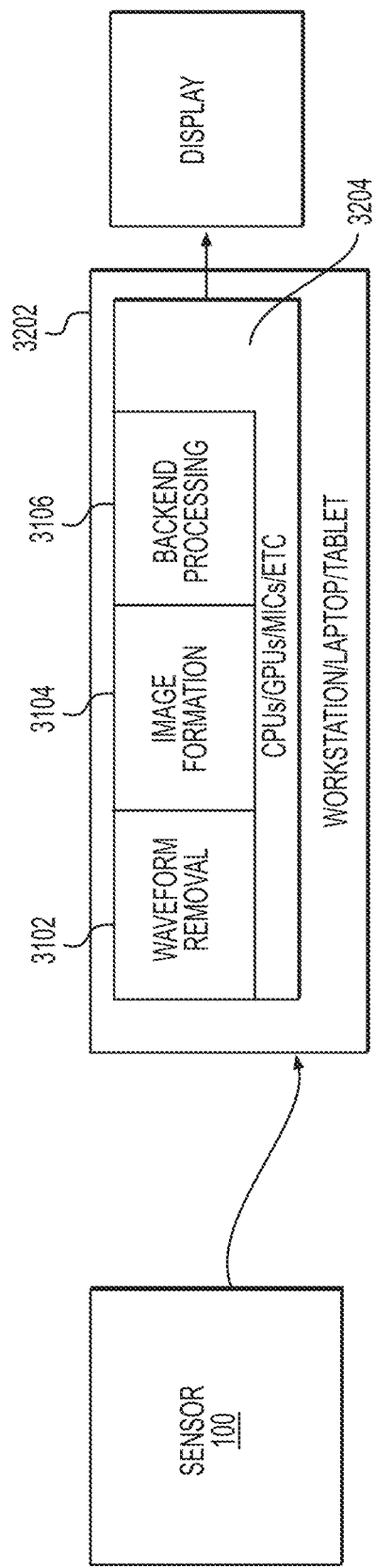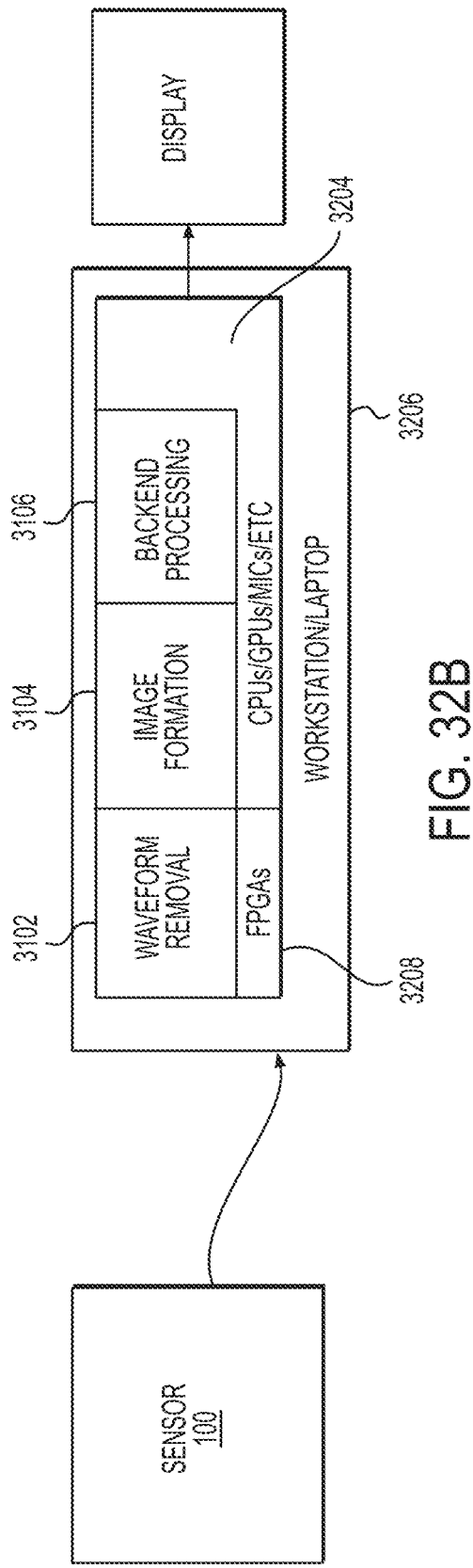

ULTRASONIC IMAGING DEVICES, SYSTEMS AND METHODS

CROSS-REFERENCE TO RELATED APPLICATIONS

This Application is a continuation claiming the benefit under 35 U.S.C. § 120 of U.S. patent application Ser. No. 15/638,331, entitled "ULTRASONIC IMAGING DEVICES, SYSTEMS AND METHODS", filed on Jun. 29, 2017, which is hereby incorporated herein by reference in its entirety.

U.S. patent application Ser. No. 15/638,331 is a continuation claiming the benefit under 35 U.S.C. § 120 of U.S. patent application Ser. No. 15/143,369, entitled "MONOLITHIC ULTRASONIC IMAGING DEVICES, SYSTEMS AND METHODS", filed on Apr. 29, 2016, which is hereby incorporated herein by reference in its entirety.

U.S. patent application Ser. No. 15/143,369 is a divisional claiming the benefit of U.S. patent application Ser. No. 14/208,281, entitled "MONOLITHIC ULTRASONIC IMAGING DEVICES, SYSTEMS AND METHODS", filed Mar. 13, 2014, which is hereby incorporated herein by reference in its entirety.

U.S. patent application Ser. No. 14/208,281 claims the benefit under 35 U.S.C. § 119(c) of U.S. Provisional Patent Application Ser. No. 61/798,851, filed on Mar. 15, 2013, and entitled "MONOLITHIC ULTRASONIC IMAGING DEVICES, SYSTEMS AND METHODS", which is hereby incorporated herein by reference in its entirety.

FIELD

Aspects of the present disclosure relate to devices, systems, and methods for imaging and/or or treatment (e.g., ultrasonic imaging and/or treatment technology). For example, certain aspects of the architecture and techniques disclosed herein allow an entire ultrasonic imaging system to be integrated on a single semiconductor substrate. Accordingly, many of the features and methodologies described herein relate to a single-chip ultrasonic imaging solution, or to devices and systems wherein at least a substantial portion of the ultrasonic imaging system is provided on a single chip.

BACKGROUND

Conventional ultrasound scanners have hardware configurations such as linear scanning with beamforming for transmit and receive operations that limit the types of imaging algorithms that can be used for image processing.

Furthermore, the cost and scalability of ultrasonic scanners has been approaching the limitations of the piezoelectric transducer technology currently dominating the industry. Piezoelectric transducers are still made using "dice and fill" manufacturing processes in which individual piezoelectric elements are cut and then positioned individually on a substrate to form the transducer. Such processes are prone to the cost, non-uniformity, and non-scalability of machining and wiring.

The problem of transporting multiple channels of analog signals from a piezoelectric transducer array to the electronics in an ultrasound scanner has greatly limited the utility of the larger and denser arrays of transducers needed to push the resolution of ultrasound imaging forward and to enable high-quality 3D volumetric imaging.

Recent advances in the fabrication techniques of capacitive micromachined ultrasound transducers (CMUTs) allow high quality ultrasound transducers to be fabricated in the same semiconductor foundries that are currently driving the electronics industry. CMUT devices also have superior bandwidth and acoustic impedance matching capabilities when compared to piezoelectric transducers. Also, the increased flexibility available to design CMUT arrays enables advanced array design techniques that can suppress imaging artifacts, improve signal quality, and reduce channel counts. The ultrasonic imaging solutions using CMUT arrays that have heretofore been proposed, however, employ conventional architectures and signal processing paradigms, and thus suffer severe limitations and drawbacks.

SUMMARY

The present disclosure details various aspects of a new paradigm for the design of a micromachined ultrasonic transducer-based ultrasonic imager. In some embodiments, on-chip signal processing may be employed in the receive signal path, for example, to reduce data bandwidth and/or a high-speed serial data module may be used to move data for all received channels off-chip as digital data stream. The digitization of received signals on-chip according to some embodiments of the present disclosure allows advanced digital signal processing to be performed on-chip, and thus permits complete or substantially complete integration of an entire ultrasonic imaging system on a single semiconductor substrate. In some embodiments, a complete "ultrasound system on a chip" solution is provided.

In some embodiments, the devices and architectures disclosed herein may be fully integrated with one or more sophisticated methods, such as, for example, one or more synthetic aperture techniques. Synthetic aperture techniques may, for example, allow the formation of high-resolution imagery from multiple receive aperture collections.

In some embodiments, a method for processing a signal from an ultrasonic transducer element involves using a component integrated on the same semiconductor die as the ultrasonic transducer element to convert an analog signal corresponding to an output of the ultrasonic transducer element into a digital signal. In some implementations, the method further involves using at least one additional component integrated on the semiconductor die to transmit data corresponding to the digital signal out of the semiconductor die as a high-speed serial data stream.

In other embodiments, an ultrasound device may include at least one ultrasonic transducer element and an analog-to-digital (ADC) converter integrated on the same semiconductor die.

In some embodiments, a method for processing a signal from an ultrasonic transducer element involves using at least one component integrated on the same semiconductor die as the ultrasonic transducer element to process a signal corresponding to an output of the transducer element to decouple waveforms therefrom.

In other embodiments, an ultrasound device may include at least one component, integrated on the same semiconductor die as an ultrasonic transducer element, that is configured to process a signal corresponding to an output of the at least one ultrasonic transducer element to decouple waveforms therefrom.

In some embodiments, a method for configuring at least two ultrasonic transducer elements involves coupling at least one ultrasonic transducer cell in one of the two transducer elements to at least one ultrasonic transducer cell in another of the two transducer elements.

In other embodiments, at least one ultrasonic transducer cell in one of at least two ultrasonic transducer elements is coupled to at least one ultrasonic transducer cell in another of the at least two ultrasonic transducer elements.

In some embodiments, a method involves using the output of a pulser to apply a bias signal to an ultrasonic transducer element on at least some occasions when the pulser is not being used to drive the ultrasonic transducer element so that the ultrasonic transducer element emits an ultrasonic pulse.

In other embodiments, an ultrasound device includes at least one ultrasonic transducer element and a pulser, wherein the pulser is configured and arranged such that, on at least some occasions when the at least one transducer element is being used to sense received ultrasonic energy, an output of the pulser is used to bias the at least one ultrasonic transducer element.

In some embodiments, a method for biasing at least one ultrasonic transducer element integrated on a semiconductor die involves biasing the at least one ultrasonic transducer element using a bias voltage applied to the semiconductor die.

In other embodiments, an ultrasound device comprises at least one ultrasonic transducer element that is configured and arranged on a semiconductor die such that a bias voltage applied to the die is also used to bias the at least one ultrasonic transducer element.

In some embodiments, a method for biasing at least one ultrasonic transducer element involves applying a ground to a side of the at least one ultrasonic transducer element facing a subject while the at least one ultrasonic transducer element is being used to image or treat the subject.

In other embodiments, an ultrasonic device is configured so that a side of at least one ultrasonic transducer element configured to face the subject during imaging or treatment is connected to a ground.

In some embodiments, a method involves configuring first and second transmit control circuits in an ultrasound device differently so that a length of a first delay between when the first control circuit receives a transmit enable signal and when a first waveform generated by the first waveform generator is applied to the first pulser is different than a length of a second delay between when the second control circuit receives the transmit enable signal and when a second waveform generated by the second waveform generator is applied to the second pulser.

In other embodiments, an ultrasound device may include at least first and second ultrasonic transducer elements and first and second transmit control circuits. The first transmit control circuit may, for example, comprise a first pulser coupled to the first ultrasonic transducer element so as to drive the first ultrasonic transducer element so that the first ultrasonic transducer element emits an ultrasonic pulse, a first waveform generator coupled to the first pulser to provide a first waveform to the first pulser in response to receipt of a transmit enable signal by the first transmit control circuit, and at least one first component that impacts a length of a first delay between when the first transmit control circuit receives the transmit enable signal and when the first waveform is applied to the first pulser. The second transmit control circuit may, for example, comprise a second pulser coupled to the second ultrasonic transducer element so as to drive the second ultrasonic transducer element so that the second ultrasonic transducer element emits an ultrasonic pulse, a second waveform generator coupled to the second pulser to provide a second waveform to the second pulser in response to receipt of the transmit enable signal by the second transmit control circuit, and at least one second component that impacts a length of a second delay between when the second transmit control circuit receives the enable signal and when the second waveform is applied to the second pulser. In some implementations, the at least one first component may be configured differently than the at least one second component, so that the length of the second delay is different than the length of the first delay.

In some embodiments, a method for configuring at least first and second waveform generators may involve using a controller to control values of first and second configurable operational parameters of the at least first and second waveform generators.

In other embodiments, a device may include at least first and second waveform generators and a controller. The waveform generators may be configured to generate waveforms for transmission by at least first and second corresponding ultrasonic transducer elements. The first waveform generator may include at least one first configurable operational parameter, and the second waveform generator may comprise at least one second configurable operational parameter. The controller may be configured to control values of the first and second configurable operational parameters.

In some embodiments, a method for making an ultrasound device comprises an act of integrating digital receive circuitry on the same semiconductor die as at least one CMOS ultrasonic transducer element.

In other embodiments, a device comprises at least one CMOS ultrasonic transducer element and digital receive circuitry formed on a single integrated circuit substrate.

In some embodiments, a method for making an ultrasound device involves fabricating at least first and second ultrasonic transducer elements above CMOS circuitry comprising at least first and second transmit control circuits and at least first and second receive control circuits corresponding to the first and second ultrasonic transducer elements.

In other embodiments, an ultrasound device comprises at least first and second ultrasonic transducer elements, and CMOS circuitry disposed underneath the at least first and second ultrasonic transducer elements, wherein the CMOS circuitry has integrated therein first and second transmit control circuits and first and second receive control circuits corresponding to the first and second ultrasonic transducer elements.

In some embodiments, a method for processing a signal from an ultrasonic transducer element involves using a component integrated on the same semiconductor die as the ultrasonic transducer element to transmit data corresponding to an output of the ultrasonic transducer element out of the semiconductor die as a high-speed serial data stream.

In other embodiments, an ultrasound device comprises at least one ultrasonic transducer element integrated on a semiconductor die, and a high-speed serial data module configured to transmit data corresponding to an output of the ultrasonic transducer element out of the semiconductor die as a high-speed serial data stream.

In some embodiments, a method involves using a controller to control values of operational parameters of transmit and/or control circuits for at least first and second ultrasonic transducer elements integrated on the same semiconductor die as the transmit and/or control circuits.

In other embodiments, a device includes at least first and second ultrasonic transducer elements integrated on a semiconductor die, transmit and/or control circuits, integrated on the semiconductor die, and a controller configured to control values of operational parameters of the transmit and/or control circuits.

BRIEF DESCRIPTION OF THE DRAWINGS

Various aspects and embodiments of the disclosed technology will be described with reference to the following figures. It should be appreciated that the figures are not necessarily drawn to scale. Items appearing in multiple figures are indicated by the same reference number in all the figures in which they appear.

FIGS. 6A-E show five different examples of how a given transducer element within an array might be configured in some embodiments;

FIGS. 32A-B illustrate embodiments in which some or all of waveform removal circuit and/or software, image formation circuit and/or software, and/or backend processing circuit and/or software may be located off-chip;

DETAILED DESCRIPTION

Figure 1:
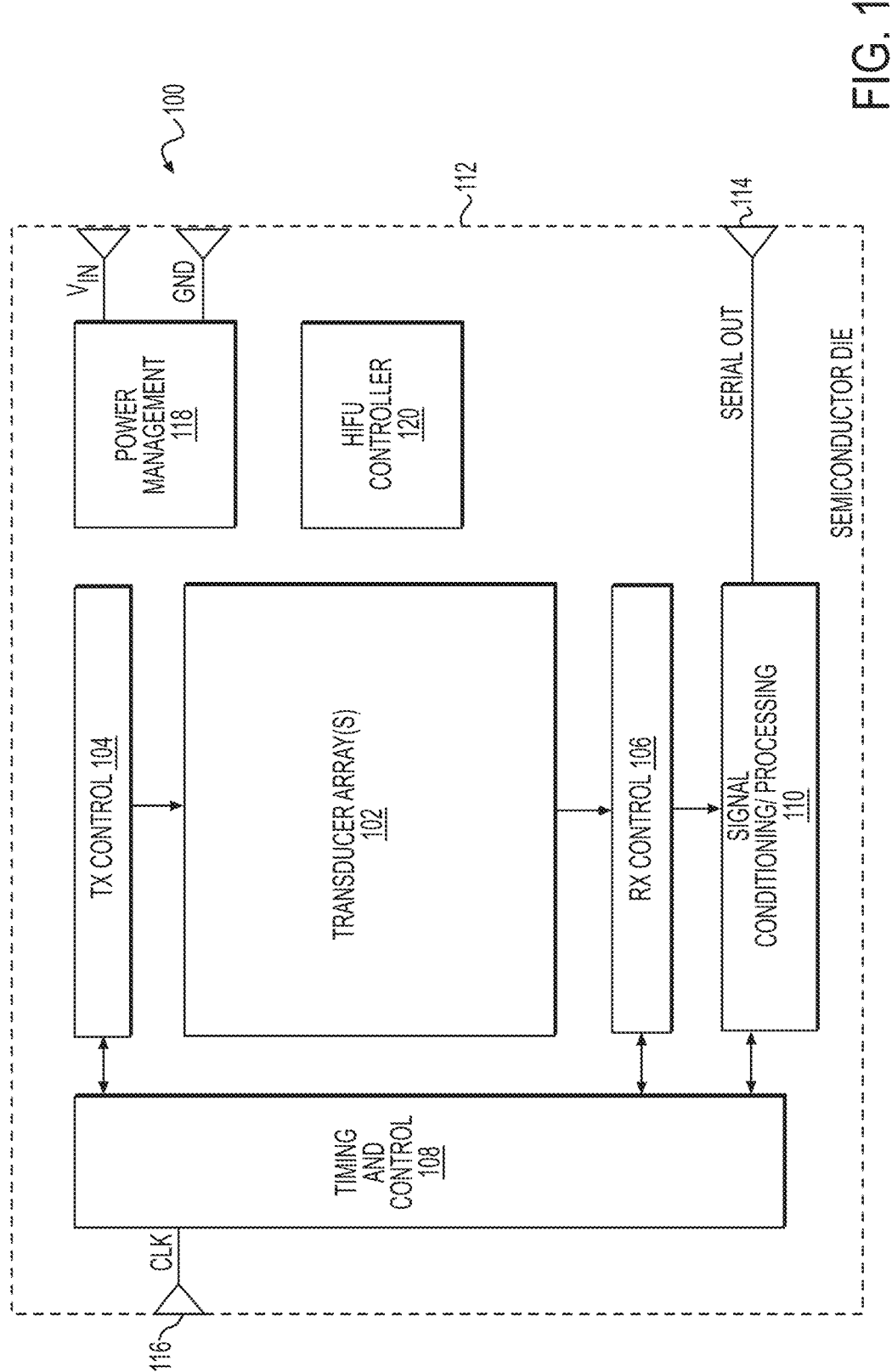
FIG. 1 shows an illustrative example of a monolithic ultrasound device embodying various aspects of the present invention.

Some embodiments of the present disclosure provide new apparatuses, systems, and methods that leverage the benefits of CMUT technology and push the forefront of ultrasound image formation processing in ultrasonic scanners. In some embodiments, a robust and highly integrated ultrasound "system on a chip" is provided with direct integration with ultrasonic transducer arrays fabricated on the same die as a fully digital ultrasound front-end. According to some aspects of the present disclosure, this architecture may allow sufficient access to fully digitized channel data to permit the use of state-of-the-art, off-the-shelf compute platforms for performing sophisticated image formation algorithms.

Previous efforts in this area to a large degree have either been focused on tight integration of standard ultrasound architecture—by designing ASICs capable of performing standard beamforming, but not more advanced techniques—or focused on implementation of advanced imaging techniques, typically creating expensive devices lacking scalable integrated technologies. The present disclosure addresses both of these issues by providing a unique, cost-effective, and scalable integrated ultrasound platform-on-a-chip that is sufficiently robust for advanced imaging applications.

Moving beyond standard beamforming methods requires an architecture that can support more than just the transmission of time-delayed pulses. The full flexibility to implement advanced waveform coding techniques requires dedicated system resources for each element in a transducer array. The present disclosure overcomes this limitation with, for example, a novel waveform generator. In some embodiments, integrated circuitry uniquely enables this waveform generator to control a multi-level (e.g., 3 or more level) pulser and provides the capability to implement many advanced ultrasound techniques in subsequent processing—a feature that has not been previously achieved in a fully integrated transducer/CMOS configuration.

Often, ultrasound receiver architectures need to reduce the data bandwidth from multiple channels. One way to do this in conventional ultrasound is to use standard beamforming methods. This operation is irreversible and is not compatible with many more advanced ultrasound image reconstruction techniques. In many cases, the full channel data rates may exceed the bandwidth of a system's external digital link. Some embodiments disclosed herein employ a novel architecture that provides the flexibility to use the full channel data in a way that enables an unprecedented level of control of the data rates for the data leaving the chip.

The integrated circuit detailed herein is uniquely designed for an integrated ultrasound imaging device. The CMOS contacts facilitate direct wafer bonding, sacrificial release, flip-chip bonding, and/or other techniques for establishing interconnections to ultrasound transducing elements.

The aspects and embodiments described above, as well as additional aspects and embodiments, are described further below. These aspects and/or embodiments may be used individually, all together, or in any combination of two or more, as the disclosure is not limited in this respect.

FIG. 1 shows an illustrative example of a monolithic ultrasound device 100 embodying various aspects of the present invention. As shown, the device 100 may include one or more transducer arrangements (e.g., arrays) 102, a transmit (TX) control circuit 104, a receive (RX) control circuit 106, a timing & control circuit 108, a signal conditioning/processing circuit 110, a power management circuit 118, and/or a high-intensity focused ultrasound (HIFU) controller 120. In the embodiment shown, all of the illustrated elements are formed on a single semiconductor die 112. It should be appreciated, however, that in alternative embodiments one or more of the illustrated elements may be instead located off-chip, as discussed in more detail below. In addition, although the illustrated example shows both a TX control circuit 104 and an RX control circuit 106, in alternative embodiments (also discussed in more detail below) only a TX control circuit or only an RX control circuit may be employed. For example, such embodiments may be employed in a circumstance where one or more transmission-only devices 100 are used to transmit acoustic signals and one or more reception-only devices 100 are used to receive acoustic signals that have been transmitted through or reflected by a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

The one or more transducer arrays 102 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 102 may, for example, include one or more CMUTs, one or more CMOS ultrasonic transducers (CUTs), and/or one or more other suitable ultrasonic transducer cells. In some embodiments, the transducer elements 304 of each transducer array 102 may be formed on the same chip as the electronics of the TX control circuit 104 and/or RX control circuit 106. Numerous examples of ultrasonic transducer cells, elements, and arrangements (e.g., arrays), as well as methods of integrating such devices with underlying CMOS circuitry, are discussed in detail in U.S. application Ser. No. 61/794,744, entitled COMPLEMENTARY METAL OXIDE SEMICONDUCTOR (CMOS) ULTRASONIC TRANSDUCERS AND METHODS FOR FORMING THE SAME, and filed on Mar. 15, 2013, the entire disclosure of which is incorporated herein by reference.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer).

The TX control circuit 104 (if included) may, for example, generate pulses that drive the individual elements of, or one or more groups of elements within, the transducer array(s) 102 so as to generate acoustic signals to be used for imaging. The RX control circuit 106 (if included), on the other hand, may receive and process electronic signals generated by the individual elements of the transducer array(s) 102 when acoustic signals impinge upon such elements.

In some embodiments, the timing & control circuit 108 may, for example, be responsible for generating all timing and control signals that are used to synchronize and coordinate the operation of the other elements in the device 100. In the example shown, the timing & control circuit 108 is driven by a single clock signal CLK supplied to an input port 116. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1) in the signal conditioning/processing circuit 110, or a 20 Mhz or 40 MHz clock used to drive other digital components on the die 112, and the timing & control circuit 108 may divide or multiply the clock CLK, as necessary, to drive other components on the die 112. In other embodiments, two or more clocks of different frequencies (such as those referenced above) may be separately supplied to the timing & control circuit 108 from an off-chip source. An illustrative example of a suitable clock generation circuit 1904 that may be included within the timing & control circuit 108 is discussed below in connection with FIGS. 19 and 20.

The power management circuit 118 may, for example, be responsible for converting one or more input voltages VIN from an off-chip source into voltages needed to carry out operation of the chip, and for otherwise managing power consumption within the device 100. In some embodiments, for example, a single voltage (e.g., 12V, 80V, 100V, 120V, etc.) may be supplied to the chip and the power management circuit 118 may step that voltage up or down, as necessary, using a charge pump circuit or via some other DC-to-DC voltage conversion mechanism. In other embodiments, multiple different voltages may be supplied separately to the power management circuit 118 for processing and/or distribution to the other on-chip components.

As shown in FIG. 1, in some embodiments, a HIFU controller 120 may be integrated on the die 112 so as to enable the generation of HIFU signals via one or more elements of the transducer array(s) 102. In other embodiments, a HIFU controller for driving the transducer array(s) 102 may be located off-chip, or even within a device separate from the device 100. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 120.

Moreover, it should be appreciated that the HIFU controller 120 may not represent distinct circuitry in those embodiments providing HIFU functionality. For example, in some embodiments, the remaining circuitry of FIG. 1 (other than the HIFU controller 120) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage) appropriate for imaging applications may cause the system to operate as an imaging system, whereas providing a higher power level (or voltage) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities. Additional details with respect to HIFU implementations and operational features that may be employed in the various embodiments set forth in the present disclosure are described in co-pending and co-owned U.S. patent application Ser. No. 13/654,337, entitled TRANSMISSIVE IMAGING AND RELATED APPARATUS AND METHODS, filed Oct. 17, 2012, the entire contents of which is incorporated herein by reference.

In the example shown, one or more output ports 114 may output a high-speed serial data stream generated by one or more components of the signal conditioning/processing circuit 110. Such data streams may, for example, be generated by one or more USB 3.0 modules, and/or one or more 10 GB, 40 GB, or 100 GB Ethernet modules, integrated on the die 112. In some embodiments, the signal stream produced on output port 114 can be fed to a computer, tablet, or smartphone for the generation and/or display of 2-dimensional, 3-dimensional, and/or tomographic images. In embodiments in which image formation capabilities are incorporated in the signal conditioning/processing circuit 110 (as explained further below), even relatively low-power devices, such as smartphones or tablets which have only a limited amount of processing power and memory available for application execution, can display images using only a serial data stream from the output port 114. Examples of high-speed serial data modules and other components that may be included in the signal conditioning/processing circuit 110 are discussed in more detail below in connection with FIGS. 21 and 31. As noted above, the use of on-chip analog-to-digital conversion and a high-speed serial data link to offload a digital data stream is one of the features that helps facilitate an "ultrasound on a chip" solution according to some embodiments of the present disclosure.

Devices 100 such as that shown in FIG. 1 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 102 (either together or individually) during one or more transmit phases, and receiving and processing signals generated by some or all of the elements in the array(s) 102 during one or more receive phases, such that during each receive phase the CMUT elements sense acoustic signals reflected by the subject. In other implementations, some of the elements in the array(s) 102 may be used only to transmit acoustic signals and other elements in the same array(s) 102 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 100 or on a single die 112.

In yet other implementations, a pair of imaging devices can be positioned so as to straddle a subject, such that one or more CMUT elements in the device(s) 100 of the imaging device on one side of the subject can sense acoustic signals generated by one or more CMUT elements in the device(s) 100 of the imaging device on the other side of the subject, to the extent that such pulses were not substantially attenuated by the subject. Moreover, in some implementations, the same device 100 can be used to measure both the scattering of acoustic signals from one or more of its own CMUT elements as well as the transmission of acoustic signals from one or more of the CMUT elements disposed in an imaging device on the opposite side of the subject.

Figure 2A:
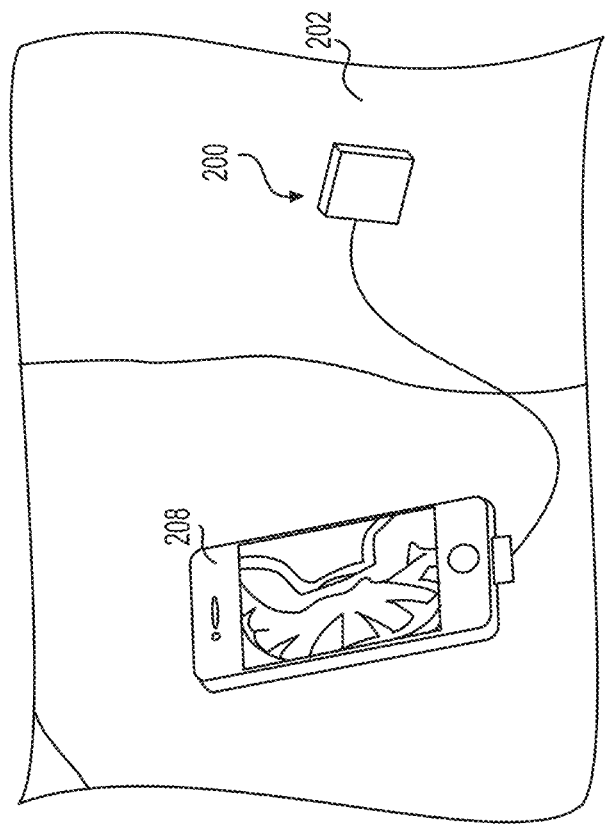
FIGS. 2A-B show example implementations of an imaging device adapted to transmit acoustic signals and receive only pulses that are backscattered from a subject.
Figure 2B:
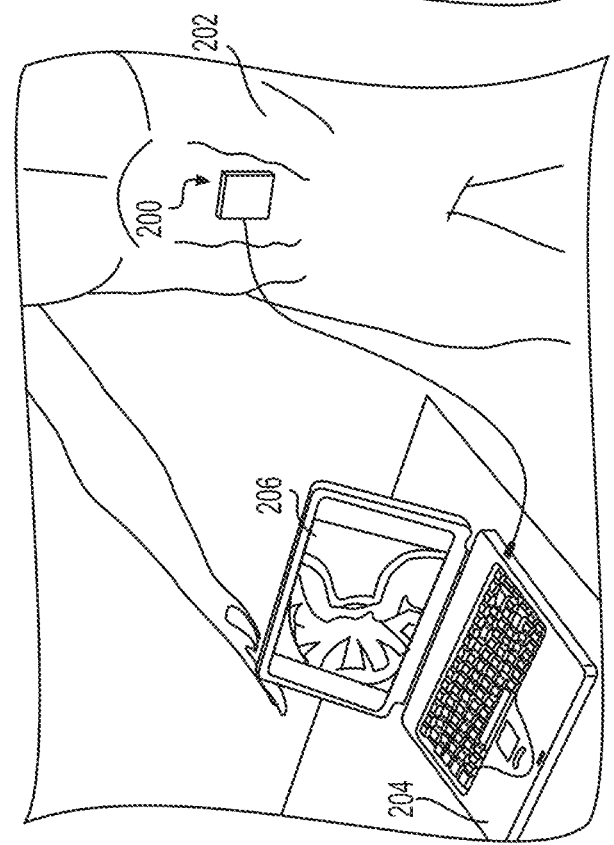

An illustrative example of an embodiment of an ultrasound unit 200 that is adapted to transmit acoustic signals and receive only pulses that are backscattered from a subject 202 is shown in FIGS. 2A-B. The ultrasound unit 200 may, for example, comprise one or more devices 100 arranged in an array on a circuit board (not shown) and supported by a housing of the ultrasound unit 200. In the example implementation of FIG. 2A, a high-speed serial data stream from the ultrasound unit 200 may be output to a serial port (e.g., a USB port) of a computer 204 for further processing and/or display on a screen 206 of the computer 204. As discussed in more detail below, the computer 204 may or may not be required to perform functions such as waveform removal, image formation, backend processing, etc., prior to displaying the image on the computer's display screen 206, depending on whether components for achieving such functionality are integrated on the die 112 of one or more of the devices 100, or are otherwise provided for in the ultrasound unit 200.

As shown in FIG. 2B, in other implementations, the high-speed serial data stream from the ultrasound unit 200 may be provided to an input port of a smartphone 208 for further processing and/or display. Because the processing power and memory available for application execution in this type of device can be limited, in some embodiments, some or all of the data processing (e.g., waveform removal, image formation, and/or backend processing, etc.) may be performed on the die 112 of one or more of the device(s) 100, or otherwise, within the ultrasound unit 200. In other embodiments, however, some or all of such data processing may additionally or alternatively be performed by one or more processors on the smartphone 208.

Figure 3B:
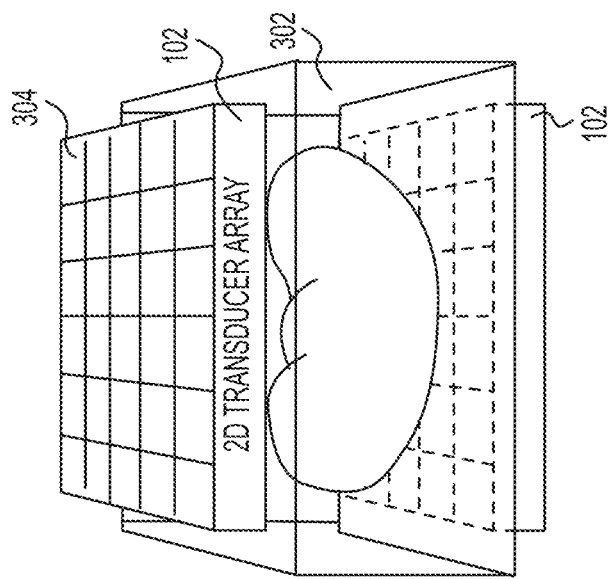
FIGS. 3A-B show an example implementation of a system that employs a pair of opposing imaging devices to image a subject.
Figure 3A:
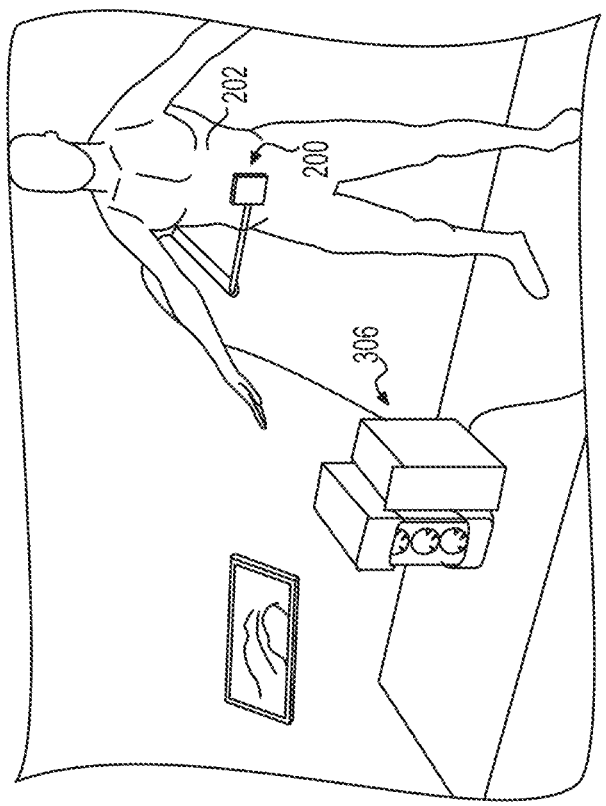

Another example of an implementation that employs a pair of opposing ultrasound units 200 is illustrated in FIGS. 3A-B. As shown in FIG. 3A, a pair of ultrasound units 200 may be arranged so as to straddle a subject 202 (the ultrasound unit 200 behind the subject 202 is not visible in FIG. 3A) and to output a serial stream of data to a desktop computer or workstation 306. FIG. 3B illustrates how transducer array(s) 102 of the device(s) 100 can be positioned so as to image a region 302 within the subject 202. As discussed above, the individual transducer elements 304 in a given array 102 can be used to generate acoustic signals or to receive acoustic signals, or both, depending on the imaging technique and methodology that is to be employed. Any of the foregoing examples may, for example, allow 2D brightness mode (B-mode), 3D B-mode, or tomographic ultrasonic imaging.

In some embodiments, the devices and architectures disclosed herein may be fully integrated with one or more sophisticated methods, such as, for example, one or more synthetic aperture techniques. Synthetic aperture techniques may, for example, allow the formation of high-resolution imagery from multiple receive aperture collections. Examples of such techniques include, but are not limited to (1) transmit and receive on all pairs of transducer elements (2) plane wave compounding, (3) inverse scattering solutions for any transmit modes, (4) interpolation range migration (e.g., Stolt interpolation) or other Fourier resampling techniques, (5) dynamic focusing. (6) delay-and-sum, and (7) virtual sources.

Numerous examples of other configurations and implementations of arrays of ultrasonic transducer elements 304 that may additionally or alternatively be employed using device(s) 100 such as those disclosed herein are described in co-pending and co-owned U.S. patent application Ser. No. 13/654,337, entitled TRANSMISSIVE IMAGING AND RELATED APPARATUS AND METHODS, filed Oct. 17, 2012, incorporated by reference above.

Figure 4A:
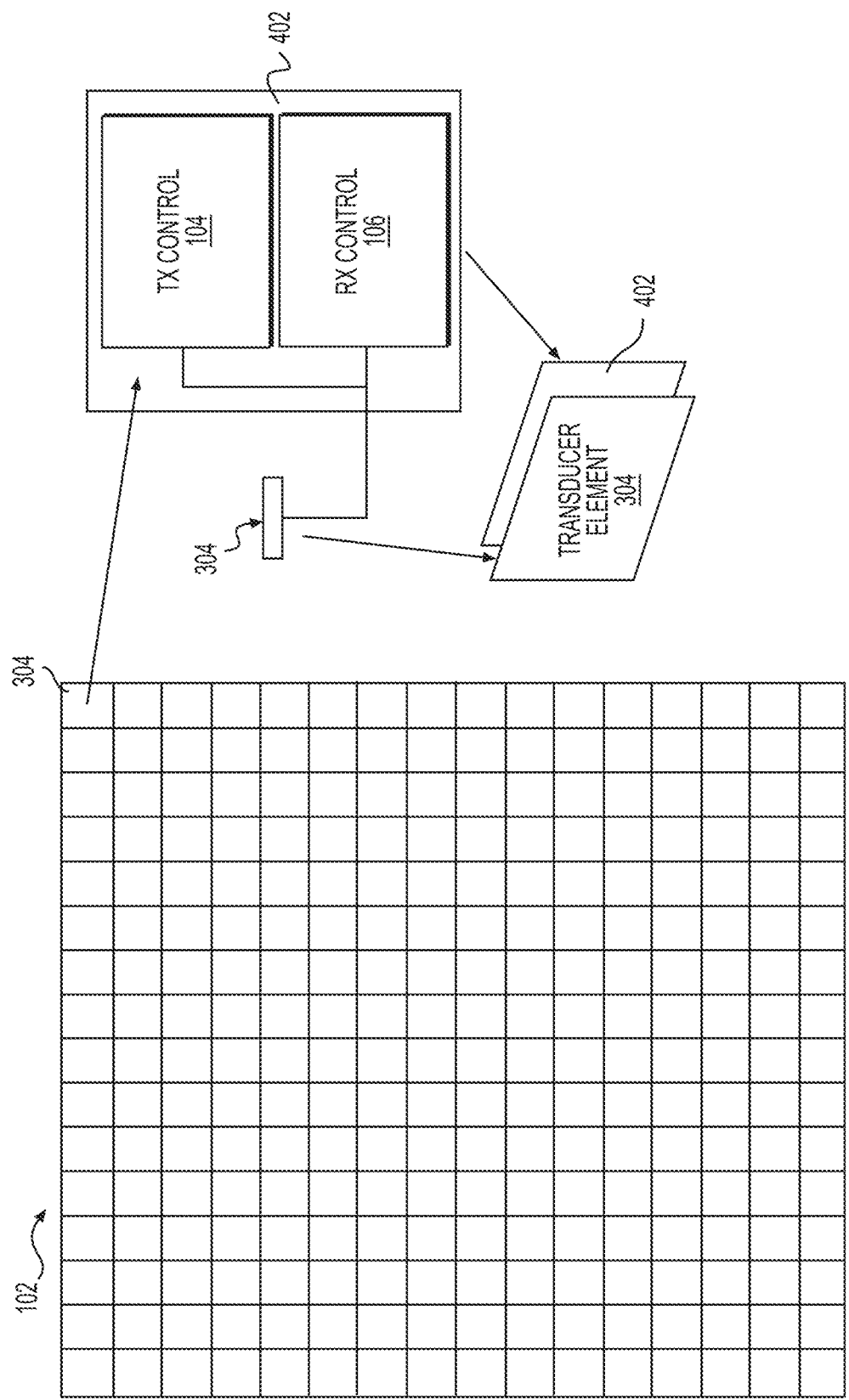
FIG. 4A shows an illustrative example of how an individual transducer element in a transducer array may be arranged with respect to CMOS circuitry for that element.

FIG. 4A shows an illustrative example of how an individual transducer element 304 in a transducer array 102 may be arranged with respect to CMOS circuitry 402 (including a TX control circuit 104 and/or an RX control circuit 106) for that transducer element 304. As shown, in some embodiments, each transducer element 304 may have associated with it a corresponding TX control circuit 104 and a corresponding RX control circuit 106. Details of example implementations of such circuits are described below. In the embodiment shown in FIG. 4A, each of the transducer elements 304 is disposed directly above its corresponding TX control circuit 104 and/or RX control circuit 106 so as to, for example, facilitate interconnections, minimize crosstalk between components, minimize parasitic capacitances, etc. (As discussed previously, details as to how transducer cells (e.g., transducer cells 602 described below), transducer elements 304, and transducer array(s) 102 may be integrated with or otherwise formed above CMOS circuitry in this manner are provided in U.S. application Ser. No. 61/794,744, entitled COMPLEMENTARY METAL OXIDE SEMICONDUCTOR (CMOS) ULTRASONIC TRANSDUCERS AND METHODS FOR FORMING THE SAME, and filed on Mar. 15, 2013, incorporated by reference above.)

It should be appreciated, however, that in other embodiments one or more of the transducer elements 304 may be otherwise arranged with respect to one or more TX control circuits 104 and/or one or more RX control circuits 106, so as to achieve other benefits or advantages. As noted above, moreover, it should be appreciated that, in some embodiments, some or all of the components of the TX control circuit 104 and/or the RX control circuit 106 may be omitted from the die 112, the device 100, and/or the ultrasound unit 200. In certain implementations, for example, the functionality of the TX control circuit 104 and/or the RX control circuit 106 may be performed by a different chip or even a different device, e.g., a computer.

Figure 4B:
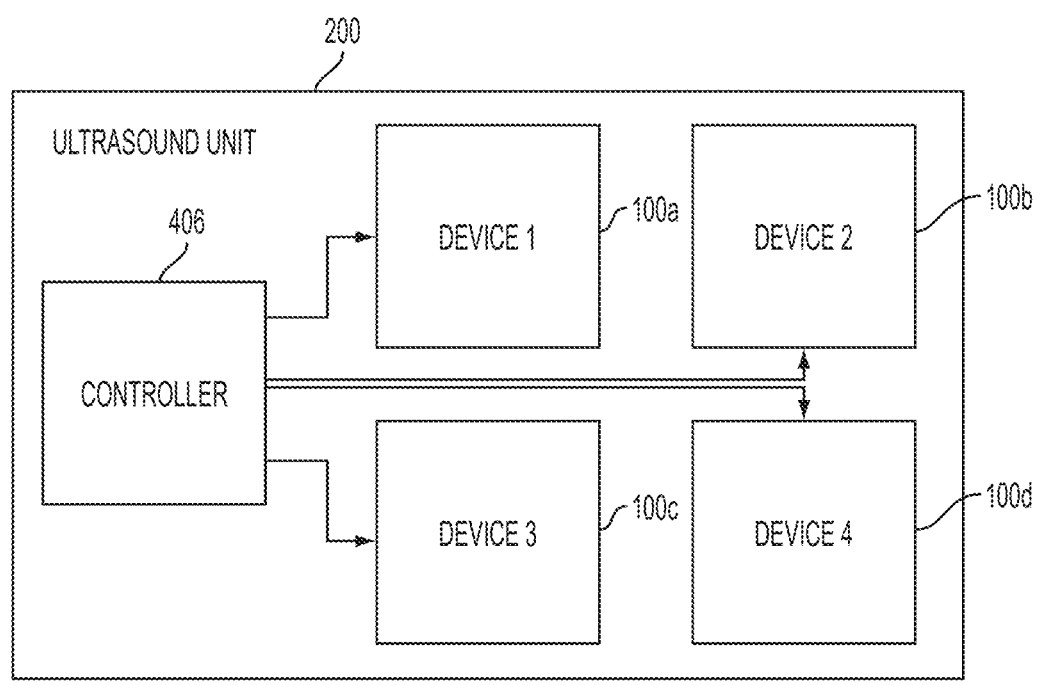
FIG. 4B shows an illustrative example of an ultrasound unit comprising a group of individual ultrasound devices that can operate together under the direction of a controller.

FIG. 4B shows an illustrative example of an ultrasound unit 200 comprising a group of individual ultrasound devices 100a-100d that can operate together under the direction of a controller 406. The ultrasound devices 100a-100d may be of the type described herein for device 100, may be an ultrasound-on-a-chip device in some embodiments, or may be other ultrasound devices. In some embodiments, each of devices 100a-100d may be a single chip device including ultrasound transducers and integrated circuitry.

Moreover, the devices 100a-100d may be the same as each other or different types of devices. For example, in some embodiments, the devices 100a-100d may all provide the same functionality (e.g., ultrasound imaging functionality). In some embodiments, one or more of the devices 100a-100d may be configured as ultrasound imaging devices and one or more may be configured as HIFU devices. In some embodiments, one or more of the devices 100a-100d may be controllable to operate as either an imaging device or a HIFU device, or both.

It should be appreciated that any number of individual devices 100 may be arranged in an array of two, four, eight, sixteen, or any other quantity, so as to form a larger area that can be used to emit and/or detect ultrasonic energy. Thus, the four illustrated devices 100a-100d represent a non-limiting example. In some such embodiments in which multiple devices 100a-100d are coupled as shown, the devices 100a-100d may be packaged within a common package or housing, may be disposed on a common substrate (e.g., a board or interposer), or may be mechanically coupled in any suitable manner.

An example of a clock generation circuit 1904 that may be included on the dies 112 of individual devices 100 in some embodiments so as to allow the operation of multiple devices 100a-100d to be synchronized is described below in connection with FIGS. 19 and 20.

Figure 5:
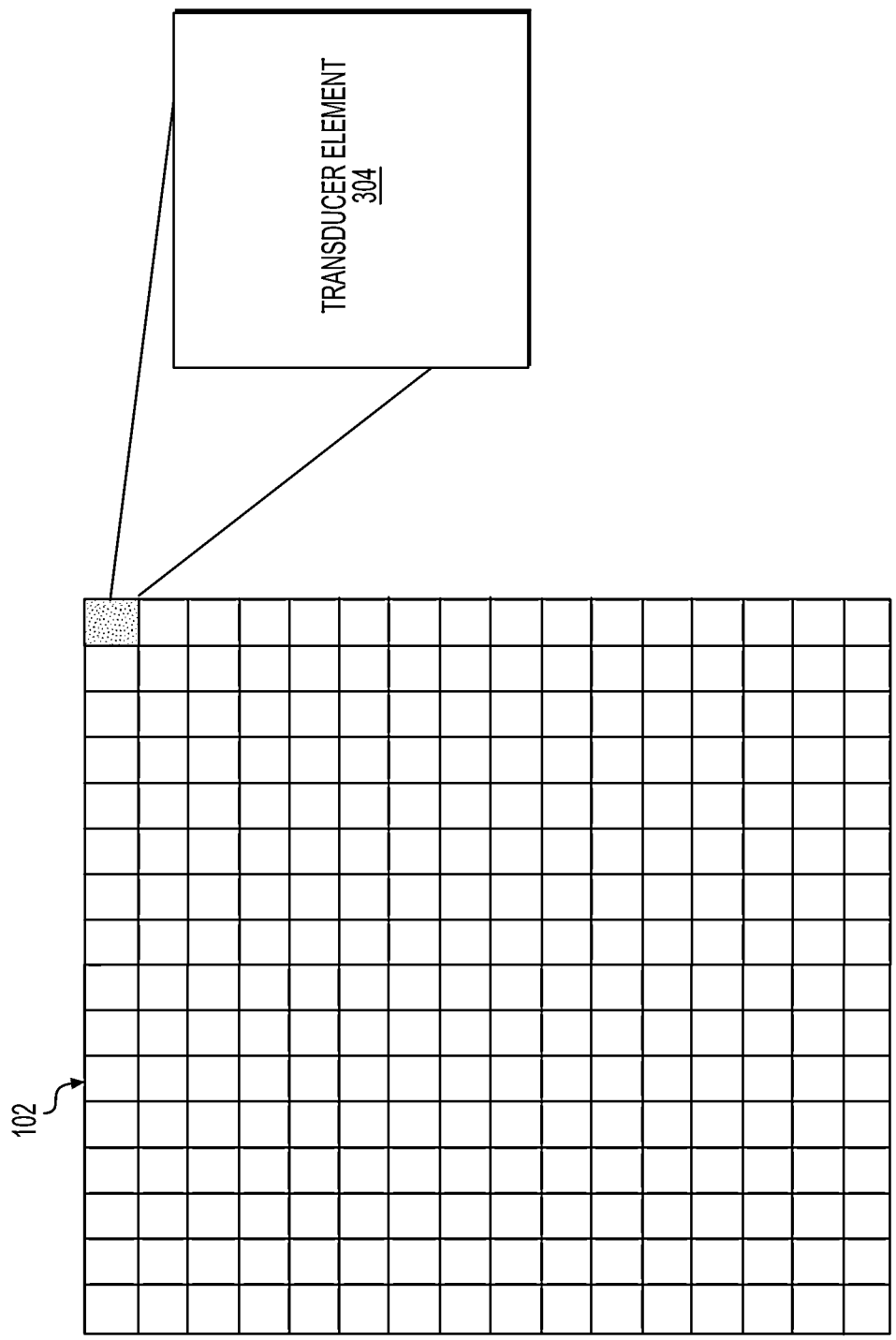
FIG. 5 illustrates how, in some embodiments, a single transducer element may fit within a larger transducer array.

FIG. 5 illustrates how, in some embodiments, a single transducer element 304 may fit within a larger transducer array 102. FIGS. 6A-E show five different examples of how a given transducer element 304 comprised of circular transducer cells 602 within an array 102 might be configured in some embodiments. As shown in FIG. 6A, in some embodiments, each transducer element 304 in an array 102 may include only a single transducer cell 602 (e.g., a single CUT or CMUT). As shown in FIGS. 6B-E, in other embodiments, each transducer element 304 in an array 102 may include a group of individual transducer cells 602 (e.g., CUTs or CMUTs). Other possible configurations of transducer elements 304 include trapezoidal elements, triangular elements, hexagonal elements, octagonal elements, etc. Similarly, each transducer cell 602 (e.g., CUT or CMUT) making up a given transducer element 304 may itself take on any of the aforementioned geometric shapes, such that a given transducer element 304 may, for example, include one or more square transducer cells 602, rectangular transducer cells 602, circular transducer cells 602, asterisk-shaped transducer cells 602, trapezoidal transducer cells 602, triangular transducer cells 602, hexagonal transducer cells 602, and/or octagonal transducer cells 602, etc.

In some embodiments, at least two of (e.g., all) of the transducer cells 602 within each given transducer element 304 act as a unit and together generate outgoing ultrasonic pulses in response to the output of the same pulser (described below) and/or together receive incident ultrasonic pulses and drive the same analog reception circuitry. When multiple transducer cells 602 are included in each transducer element 304, the individual transducer cells 602 may be arranged in any of numerous patterns, with the particular pattern being chosen so as to optimize the various performance parameters, e.g., directivity, signal-to-noise ratio (SNR), field of view, etc., for a given application. In some embodiments in which CUTs are used as transducer cells 602, an individual transducer cell 602 may, for example, be on the order of about 20-110 µm wide, and have a membrane thickness of about 0.5-1.0 µm, and an individual transducer element 304 may have a depth on the order of about 0.1-2.0 µm, and have a diameter of about 0.1 mm-3 mm, or any values in between. These are only illustrative examples of possible dimensions, however, and greater and lesser dimensions are possible and contemplated.

Figure 7A:
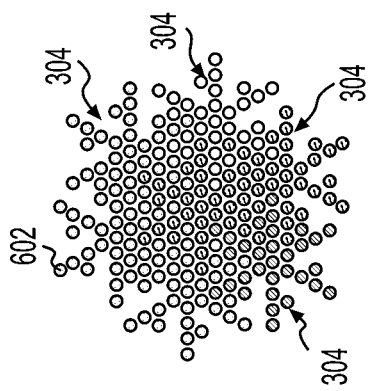
FIGS. 7A-C show examples of how transducer elements may be intermingled to reduce grating lobes, etc., in some embodiments.
Figure 7B:
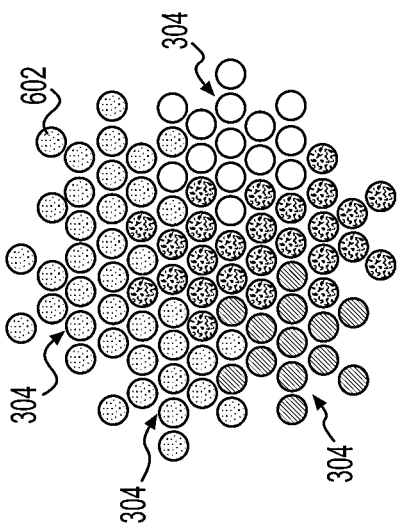
Figure 7C:
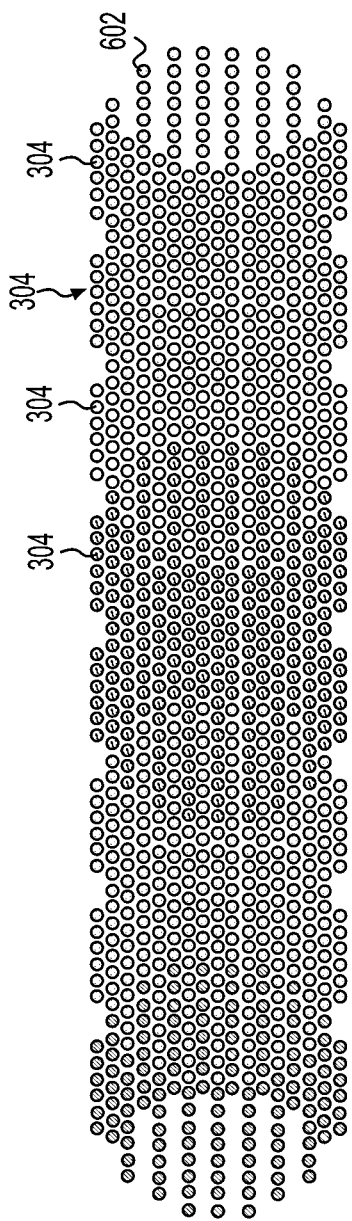

As described, for example, in Bavaro, V., et al., "Element Shape Design of 2-D CMUT Arrays for Reducing Grating Lobes, IEEE Transactions on Ultrasonics, Ferroelectrics, and Frequency Control, Vol. 55, No. 2, February 2008, which is incorporated by reference in its entirety, it is possible to select the shape of and interrelationships among transducer elements 304 so as to optimize the performance parameters of a transducer array 102. Embodiments of the ultrasonic devices described herein may employ such techniques. FIGS. 7A-B show illustrative examples in which the transducer cells 602 (e.g., CUTs or CMUTs) of asterisk-shaped transducer elements 304 are intermingled, and FIG. 7C shows an illustrative example in which the transducer cells 602 of circular-shaped transducer elements 306 are intermingled, so as to achieve advantages such as the reduction of grating lobes.

In some embodiments, a similar effect of reducing grating lobes, etc., can be achieved, either in addition to or in lieu of intermingling transducer elements 304 in the array 102, by coupling one or more transducer cells 602 in a given transducer element 304 with one or more transducer cells 602 in one or more adjacent or nearby transducer elements 304. By using such a technique, better use of the total transducer area can be attained because a given transducer cell 602 need not belong to only a single transducer element 304 and can instead be shared by multiple transducer elements 304. This cell sharing technique may, in some embodiments, be combined with an apodization technique in which some transducer cells 602 in a transducer element 304 are caused to radiate less power than other transducer cells 602 in the same element.

Figure 8:
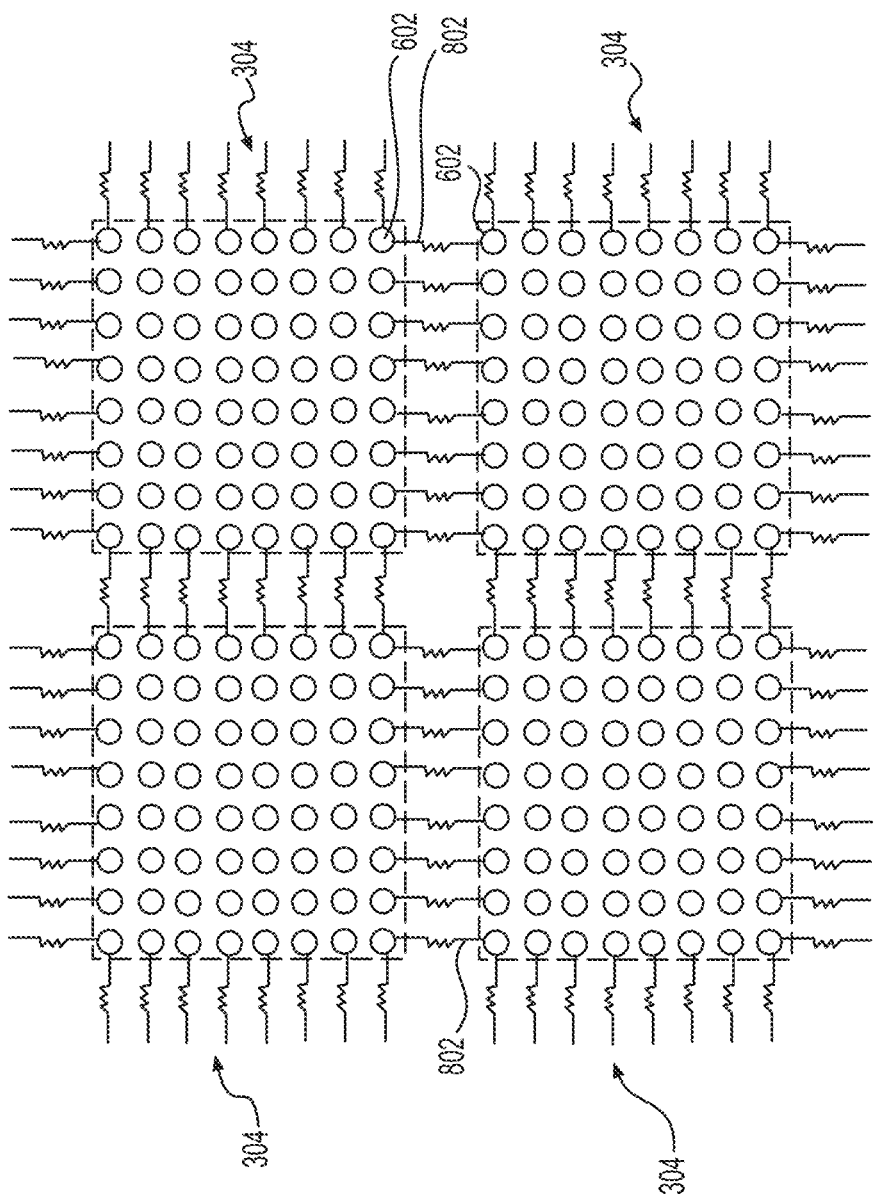
FIGS. 8-9 illustrate examples of how transducers cells included in respective transducer elements of an array may be coupled together to reduce grating lobes, etc., in some embodiments.

An illustrative example of a suitable cell-sharing technique is shown in FIG. 8. In this example, transducer cells 602 (e.g., CUTs or CMUTs) at the peripheries of transducer elements 304 are coupled to one another via coupling elements 802. In some embodiments, the coupling elements 802 may, for example, comprise polysilicon resistors. In other implementations, the coupling elements 802 may additionally or alternatively comprise capacitive and/or inductive elements or features. For example, inductive couplings may be created between pairs of transducer cells 602 by running conductors for to-be-coupled transducer cells 602 in close proximity to one another. In some embodiments, certain transducer cells 602, e.g., the transducer cells 602 on the periphery of the shared transducer elements 304, may additionally be operated according to a desired apodization scheme. In the embodiment shown in FIG. 8, for example, an apodization scheme may be applied to the transducer cells 602 that are coupled to the transduce cells 602 in other elements so that they radiate less power than the transducer cells 602 that are not so coupled.

Figure 9:
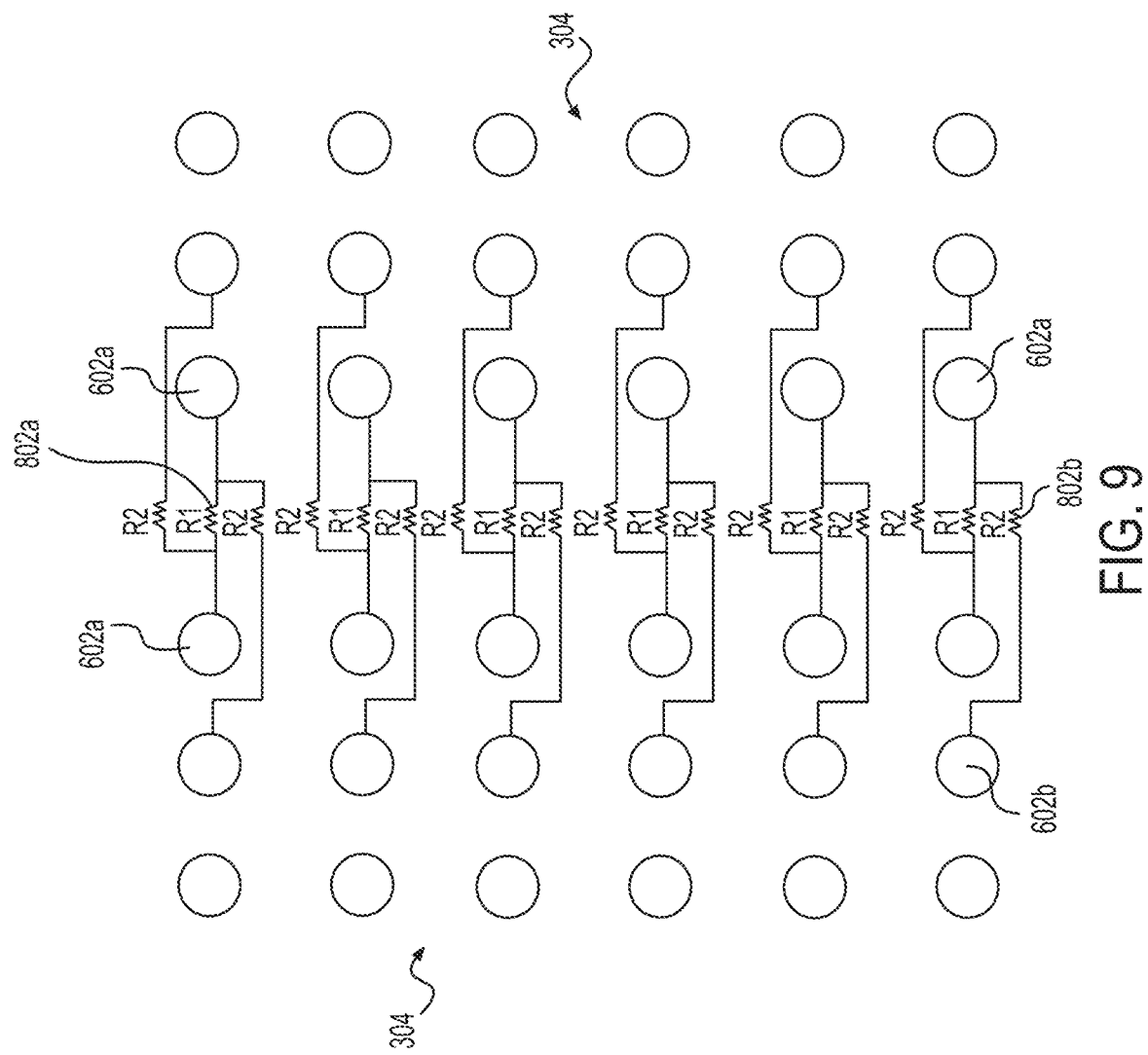

In some embodiments, it can also be advantageous for different impedance values to be used between different pairs of transducer cells 602, depending, for example, on the proximity of a transducer cell 602 to the periphery of its transducer element 304. In some embodiments, for example, pairs of transducer cells 602 that are both located on the peripheries of two transducer elements 304 may be coupled together with an impedance value that is higher than the impedance value used to couple together pairs of transducer cells 602 for which one of the transducer cells 602 is not on the periphery of its transducer element 304. This possible configuration is illustrated in FIG. 9. As shown, transducer cells 602a on the periphery of two transducer elements 304 may be coupled together via a coupling 802a (e.g., a polysilicon resistor) having a resistance value R1, whereas a transducer cell 602b closer to the center of a transducer element 304 may be coupled to another transducer cell 602 via a coupling 802b having a resistance value R2. The resistance value R2 may, for example, be greater than the resistance value R1. In some embodiments, a gradient of impedance values may be employed that increases gradually from the periphery to the middle portion of a transducer element 304. Again, such a cell sharing technique employing different impedance values, or a gradient of impedance values, may be combined with an apodization technique so as optimize the performance of the array(s) 102 for a particular application.

As noted above, the above techniques for sharing and/or apodizing the transducer elements 304 in the array(s) 102, either symmetrically or asymmetrically, and either uniformly about the perimeters, according to some gradient, or otherwise, may be combined with the intermingling technique discussed above, such that transducer elements 304 may have transducer cells 602 that are both intermingled and coupled together at their peripheries or via a gradient of impedance values, or otherwise.

Figure 10:
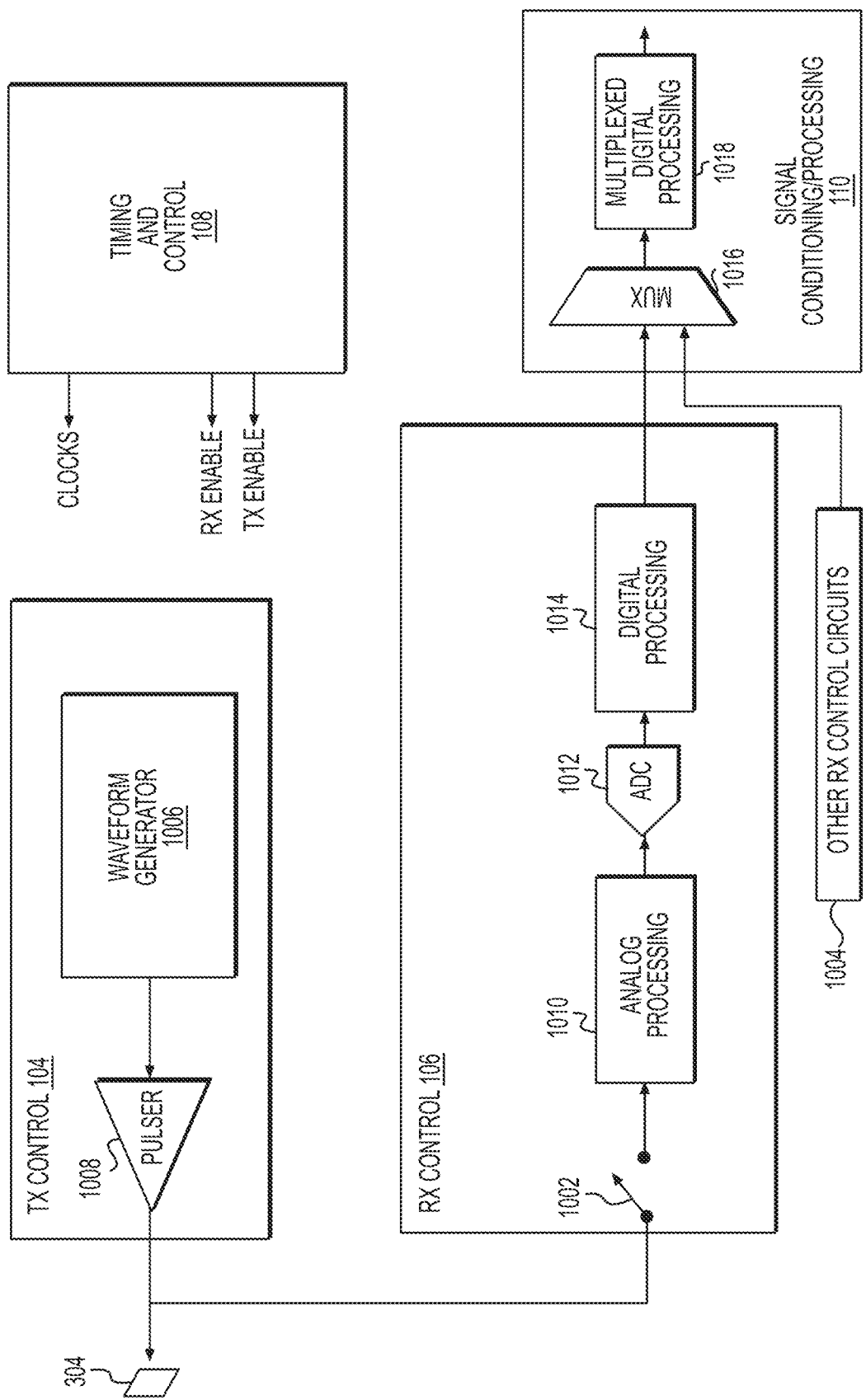
FIG. 10 is a block diagram illustrating how, in some embodiments, the TX control circuit and the RX control circuit for a given transducer element may be used either to energize the element to emit an ultrasonic pulse, or to receive and process a signal from the element representing an ultrasonic pulse sensed by it.

FIG. 10 is a block diagram illustrating how, in some embodiments, the TX control circuit 104 and the RX control circuit 106 for a given transducer element 304 may be used either to energize the transducer element 304 to emit an ultrasonic pulse, or to receive and process a signal from the transducer element 304 representing an ultrasonic pulse sensed by it. In some implementations, the TX control circuit 104 may be used during a "transmission" phase, and the RX control circuit may be used during a "reception" phase that is non-overlapping with the transmission phase. In other implementations, one of the TX control circuit 104 and the RX control circuit 106 may simply not be used in a given device 100, such as when a pair of ultrasound units 200 is used for only transmissive imaging. As noted above, in some embodiments, a device 100 may alternatively employ only a TX control circuit 104 or only an RX control circuit 106, and aspects of the present technology do not necessarily require the presence of both such types of circuits. In various embodiments, each TX control circuit 104 and/or each RX control circuit 106 may be associated with a single transducer cell 602 (e.g., a CUT or CMUT), a group of two or more transducer cells 602 within a single transducer element 304, a single transducer element 304 comprising a group of transducer cells 602, a group of two or more transducer elements 304 within an array 102, or an entire array 102 of transducer elements 304.

In the example shown in FIG. 10, there is a separate TX control circuit 104/RX control circuit 106 combination for each transducer element 304 in the array(s) 102, but there is only one instance of each of the timing & control circuit 108 and the signal conditioning/processing circuit 110. Accordingly, in such an implementation, the timing & control circuit 108 may be responsible for synchronizing and coordinating the operation of all of the TX control circuit 104/RX control circuit 106 combinations on the die 112, and the signal conditioning/processing circuit 110 may be responsible for handling inputs from all of the RX control circuits 106 (see element 1004 in FIG. 10) on the die 112.

As shown in FIG. 10, in addition to generating and/or distributing clock signals to drive the various digital components in the device 100, the timing & control circuit 108 may output either an "TX enable" signal to enable the operation of each TX control circuit 104, or an "RX enable" signal to enable operation of each RX control circuit 106. In the example shown, a switch 1002 in the RX control circuit 106 may always be opened before the TX control circuit 104 is enabled, so as to prevent an output of the TX control circuit 104 from driving the RX control circuit 106. The switch 1002 may be closed when operation of the RX control circuit 106 is enabled, so as to allow the RX control circuit 106 to receive and process a signal generated by the transducer element 304.

As shown, the TX control circuit 104 for a respective transducer element 304 may include both a waveform generator 1006 and a pulser 1008. The waveform generator 1006 may, for example, be responsible for generating a waveform that is to be applied to the pulser 1008, so as to cause the pulser 1008 to output a driving signal to the transducer element 304 corresponding to the generated waveform.

In the example shown in FIG. 10, the RX control circuit 106 for a respective transducer element 304 includes an analog processing block 1010, an analog-to-digital converter (ADC) 1012, and a digital processing block 1014. The ADC 1012 may, for example, comprise a 10-bit. 20 Msps, 40 Msps, or 80 Msps ADC.

After undergoing processing in the digital processing block 1014, the outputs of all of the RX control circuits 106 on the die 112 (the number of which, in this example, is equal to the number of transducer elements 304 on the chip) are fed to a multiplexer (MUX) 1016 in the signal conditioning/processing circuit 110. The MUX 1016 multiplexes the digital data from the various RX control circuits 106, and the output of the MUX 1016 is fed to a multiplexed digital processing block 1018 in the signal conditioning/processing circuit 110, for final processing before the data is output from the die 112, e.g., via one or more high-speed serial output ports 114. Examples implementations of the various circuit blocks shown in FIG. 10 are discussed further below. As explained in more detail below, various components in the analog processing block 1010 and/or the digital processing block 1014 may serve to decouple waveforms from the received signal and otherwise reduce the amount of data that needs to be output from the die 112 via a high-speed serial data link or otherwise. In some embodiments, for example, one or more components in the analog processing block 1010 and/or the digital processing block 1014 may thus serve to allow the RX control circuit 106 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

Although particular components that may optionally be included in the analog processing block 1010 are described below, it should be appreciated that digital counterparts to such analog components may additionally or alternatively be employed in the digital processing block 1014. The converse is also true. That is, although particular components that may optionally be included in the digital processing block 1014 are described below, it should be appreciated that analog counterparts to such digital components may additionally or alternatively be employed in the analog processing block 1010.

Figure 11A:
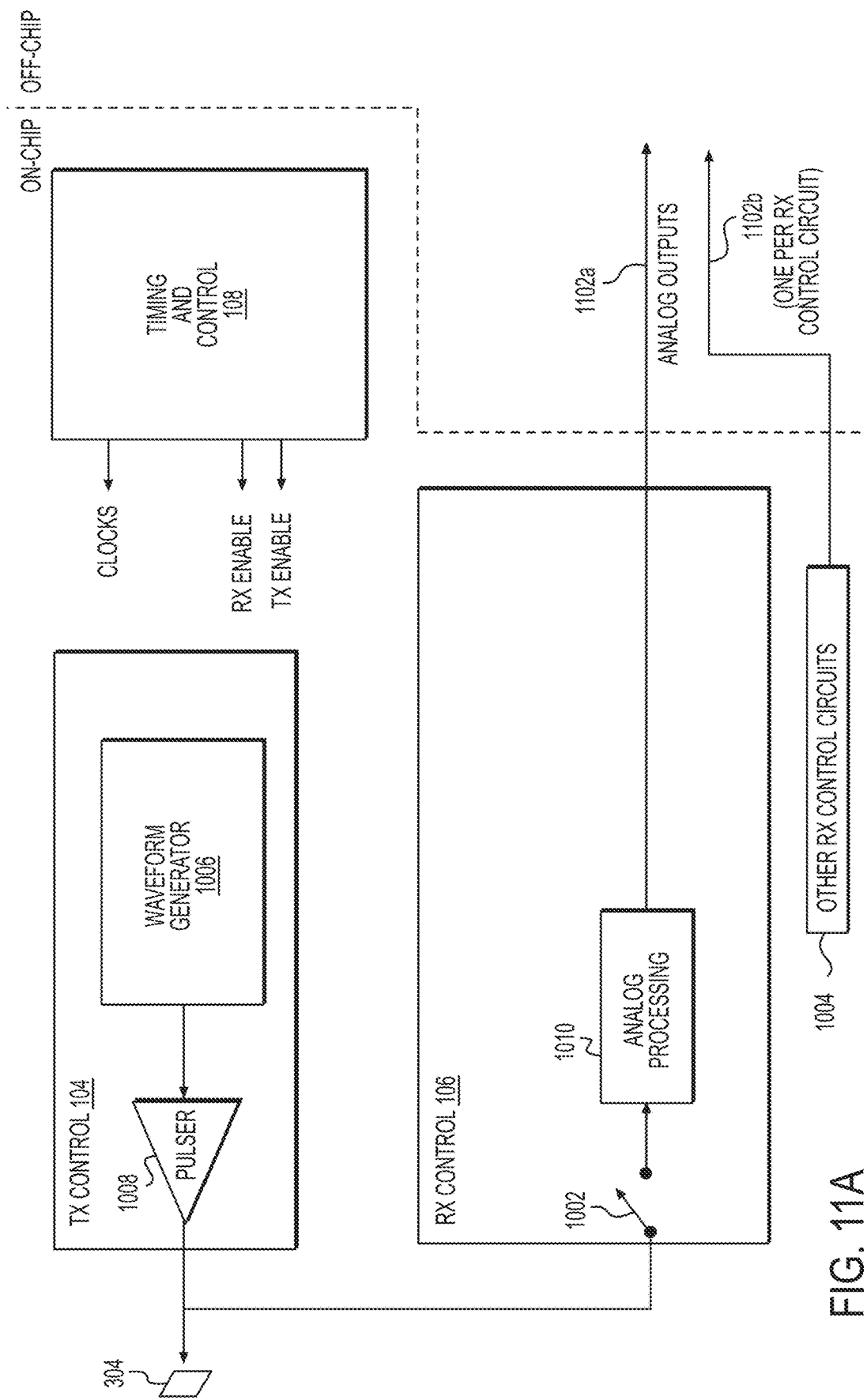
FIG. 11A illustrates an embodiment of an ultrasound device in which digital processing of a received signal may be performed off-chip.

FIG. 11A illustrates an embodiment of a device 100 in which digital processing of a received signal is not performed on the die 112. In some implementations, this embodiment may be essentially identical to the embodiment of FIG. 10 in terms of its basic structure and function, except that the RX control circuits 106 might not, for example, employ an ADC 1012 or a digital processing block 1014, and an on-chip signal conditioning/processing circuit 110 may be omitted. It should be appreciated, however, that in the embodiment of FIG. 11A one or more buffers/drivers (not shown) may additionally be employed to drive the analog signals onto output lines 1102a-b of the die 112.

Figure 11B:
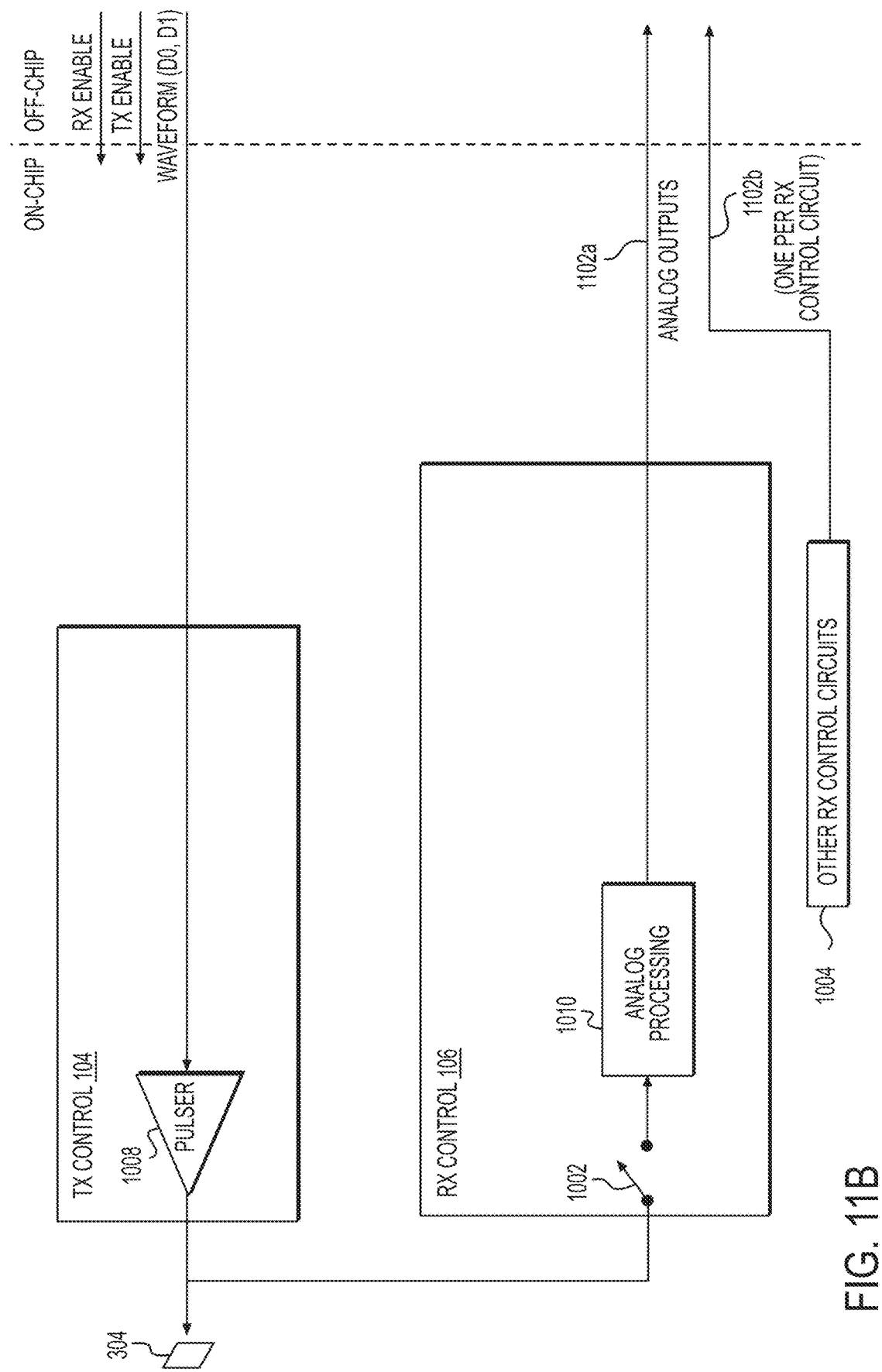
FIG. 11B illustrates an embodiment of an ultrasound device in which a waveform generator and some or all of the other digital circuitry may be located off-chip.

FIG. 11B illustrates an embodiment of an ultrasound device in which a waveform generator (not shown) and some or all of the other digital circuitry discussed herein may be located off-chip, rather than on the semiconductor die 112. In some implementations, this embodiment may be otherwise identical to the embodiment of FIG. 10 in terms of its basic structure and functionality. In some embodiments, the pulsers 1008 may additionally or alternatively be located off-chip.

Figure 12A:
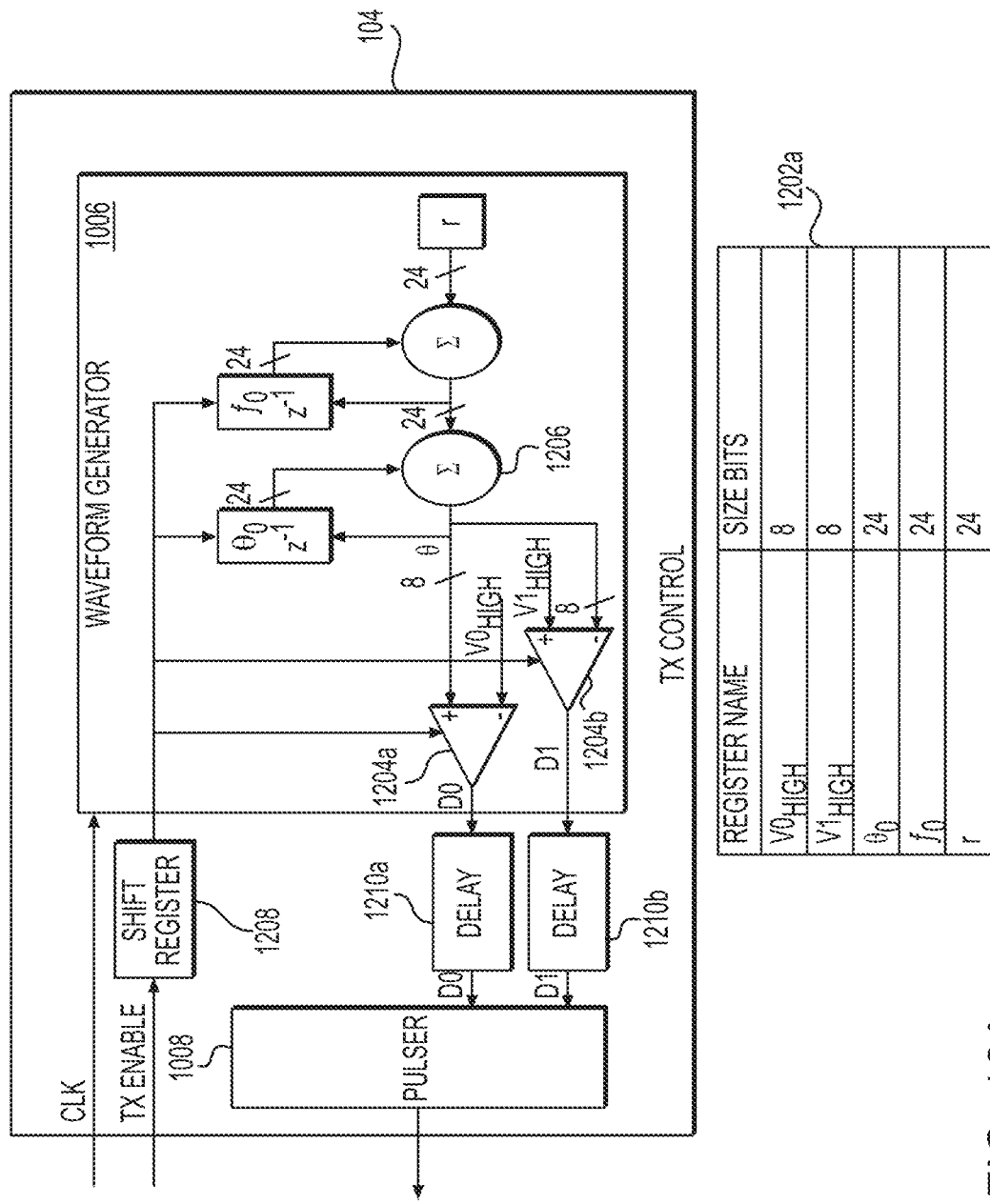
FIG. 12A-B show examples of circuitry that may be included in each TX control circuit, in some embodiments, so as to allow for true time delay and amplitude control at every transmit location of the transducer array(s)

FIG. 12A shows an example of circuitry that may be included in each TX control circuit 104, in some embodiments, so as to allow for true time delay and amplitude control at every transmit location of the array(s) 102. In the illustrated example, the waveform generator 1006 is a chirp generator that includes a set of registers 1202a that can be set to control the characteristics of the chirp that is supplied to a tri-level pulser 1008. Specifically, a phase register "$\theta_0$" controls the starting phase of the chirp, the frequency register "$f_0$" controls the starting frequency of the chirp, and the chirp rate register "r" controls the rate at which the frequency of the chirp changes over time. The comparators 1204a-b serve to discretize the waveform signal output by accumulator 1206, so that the logical values D0, D1 supplied to the tri-level pulser 1008 are either "1,0," "0,0," or "0,1," depending on comparisons of the output of the accumulator 1206 to the values $V0_{HIGH}$ and $V1_{HIGH}$ in the registers 1202a.

Figure 12B:
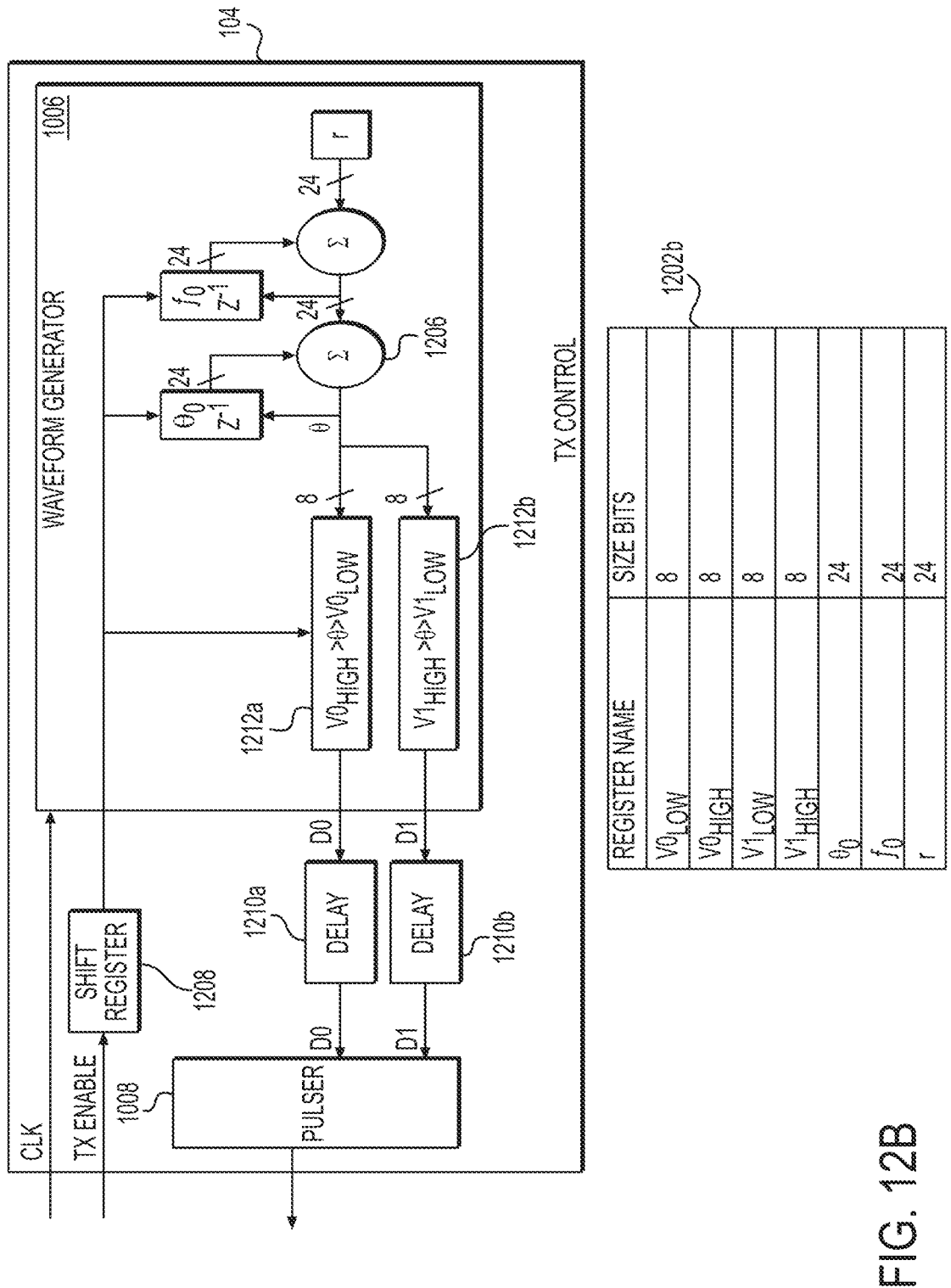

FIG. 12B shows an alternative embodiment of the waveform generator 1006. In the FIG. 12B embodiment, rather than using comparators 1204a-b to discretize the simulated sine-wave signal output by the accumulator 1206, a look up table 1212a is used to determine whether the output of accumulator 1206 is within a range defined by the values of $V0_{HIGH}$ and $V0_{LOW}$ in the registers 1202b, and a look up table 1212b is used to determine whether the output of accumulator 1206 is within a range defined by the values of $V1_{HIGH}$ and $V1_{LOW}$ in the registers 1202b.

The configuration and operation of a tri-level pulser suitable for use as the pulser 1008 of FIGS. 12A-B according to some embodiments, as well as the benefits of employing such a pulser to drive a CMUT element, are described in Kailiang. C, "Ultrasonic Imaging Front-End Design for CMUT: A 3-Level 30 Vpp Pulse-Shaping Pulser with Improved Efficiency and a Noise-Optimized Receiver," IEEE Asian Solid-State Circuits Conference," Nov. 12-14, 2012/Kobe, Japan, which is incorporated herein by reference in its entirety. Those details will therefore not be repeated here.

In the example embodiments shown in FIGS. 12A-B, the TX control circuit 104 is provided with three levels of control over the timing of the output of the pulser 1008. The coarsest level of timing control is provided by a shift register 1208 (which, in some embodiments, may be programmable, e.g., via the timing & control unit 108) located at the input of the waveform generator 1006. The next finest level of timing control is provided by the settings of the values "$\theta_0$" and "$f_0$" in the registers 1202a-b. The finest level of timing control is provided by delay lines 1210a-b, which may, for example, include PIN diodes that provide for delays on the order of about 72 picoseconds to 22 nanoseconds, or any delay value in between, though lesser and greater delays are also possible and contemplated.

Embodiments of the waveform generator 1006 thus described allow for wideband or narrowband beamforming, coded excitation, e.g., Golay codes, Hadamard codes, Walsh codes, Cyclic Algorithm New (CAN) coding, azimuth phase coding, and/or other orthogonal waveforms, and/or may also allow the generation of gated continuous wave (CW) or impulse generation. Numerous additional examples of waveform generation techniques and options are described in co-pending and co-owned U.S. patent application Ser. No. 13/654,337, incorporated by reference above, and will thus not be described further here.

Figure 13A:
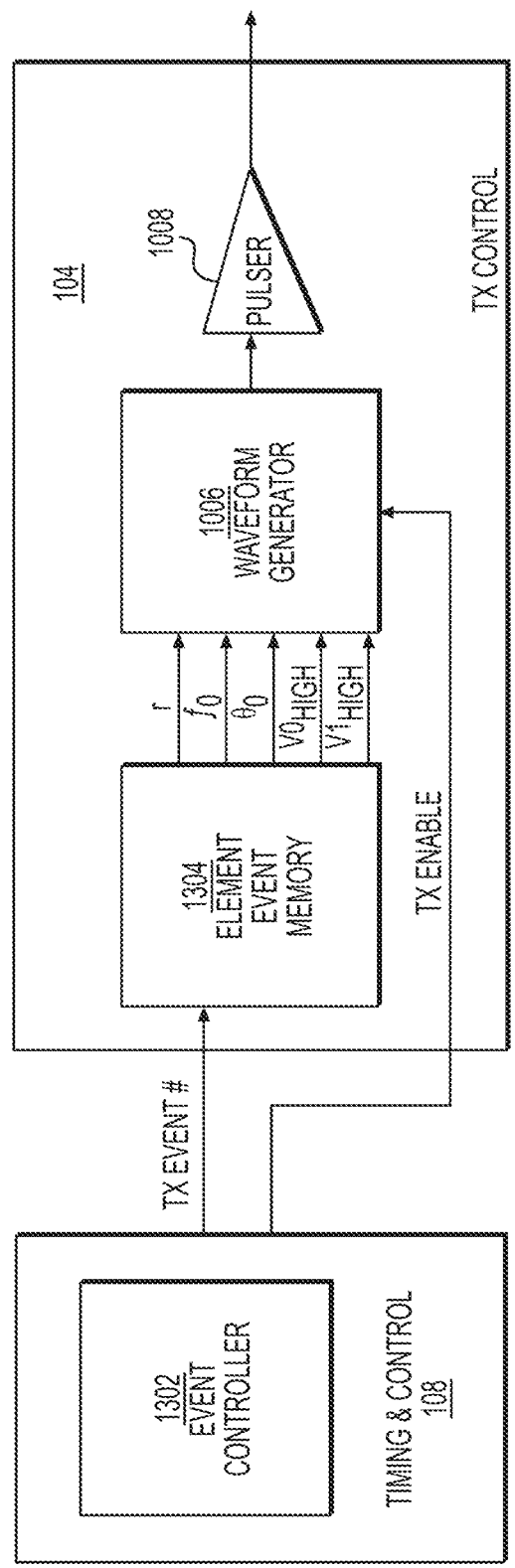
FIG. 13A shows an illustrative example of components that may be employed in the timing & control circuit and each TX control circuit to selectively determine values for the registers used by the waveform generator in the embodiments of FIGS. 12A-B.

FIG. 13A shows an illustrative example of components that may be employed in the timing & control circuit 108 and each TX control circuit 104 to selectively determine values for the registers 1202a-b used by the waveform generator 1006 in the embodiments of FIGS. 12A-B. As shown, each TX control circuit 104 may include an element event memory 1304 that stores values for the registers 1202a-b corresponding to each of several "TX event" numbers, and the timing & control circuit 108 may include an event controller 1302 that is responsible for communicating appropriate TX event numbers to each of the TX control circuits 104 on the die 112. With such an arrangement, the waveform supplied to each transducer element 304 in an array 102 can change from pulse to pulse, and by appropriately programming the event element memory 1304, complicated event sequencing, such as the excitation coding, e.g., Azimuth coding, mentioned above, focus/planewave scanning, etc., can be achieved. Although not illustrated in FIG. 13, it should be appreciated that, for operation with the waveform generator embodiment of FIG. 12B, values of $V0_{low}$ and $V1_{low}$ may additionally be provided from the element event memory 1304 to the waveform generator 1006.

Figure 14:
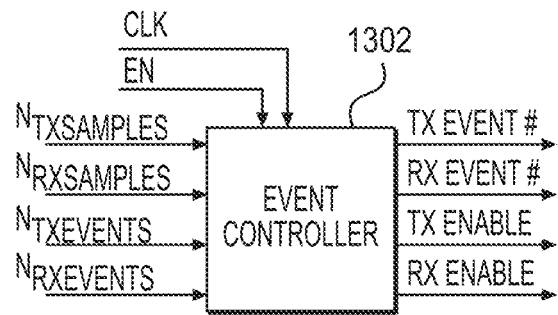
FIG. 14 shows examples of inputs and outputs for an event controller of the timing & control circuit that may be provided, in some embodiments, so as to control both the transmission events and the receive events that occur in an ultrasound device.

FIG. 14 shows inputs and outputs for an event controller 1302 of the timing & control circuit 108 that may be provided, in some embodiments, so as to control both the transmission events and the receive events that occur in a ultrasound device 100. In the embodiment shown, the event controller is provided with the parameters $N_{TXSamples}$, $N_{RXSamples}$, $N_{TXEvents}$, and $N_{RXEvents}$, and, when enabled via an enable signal "En." generates and outputs TX and RX event numbers, as well as TX and RX enable signals, in response to an input clock "Clk."

Figure 15A:
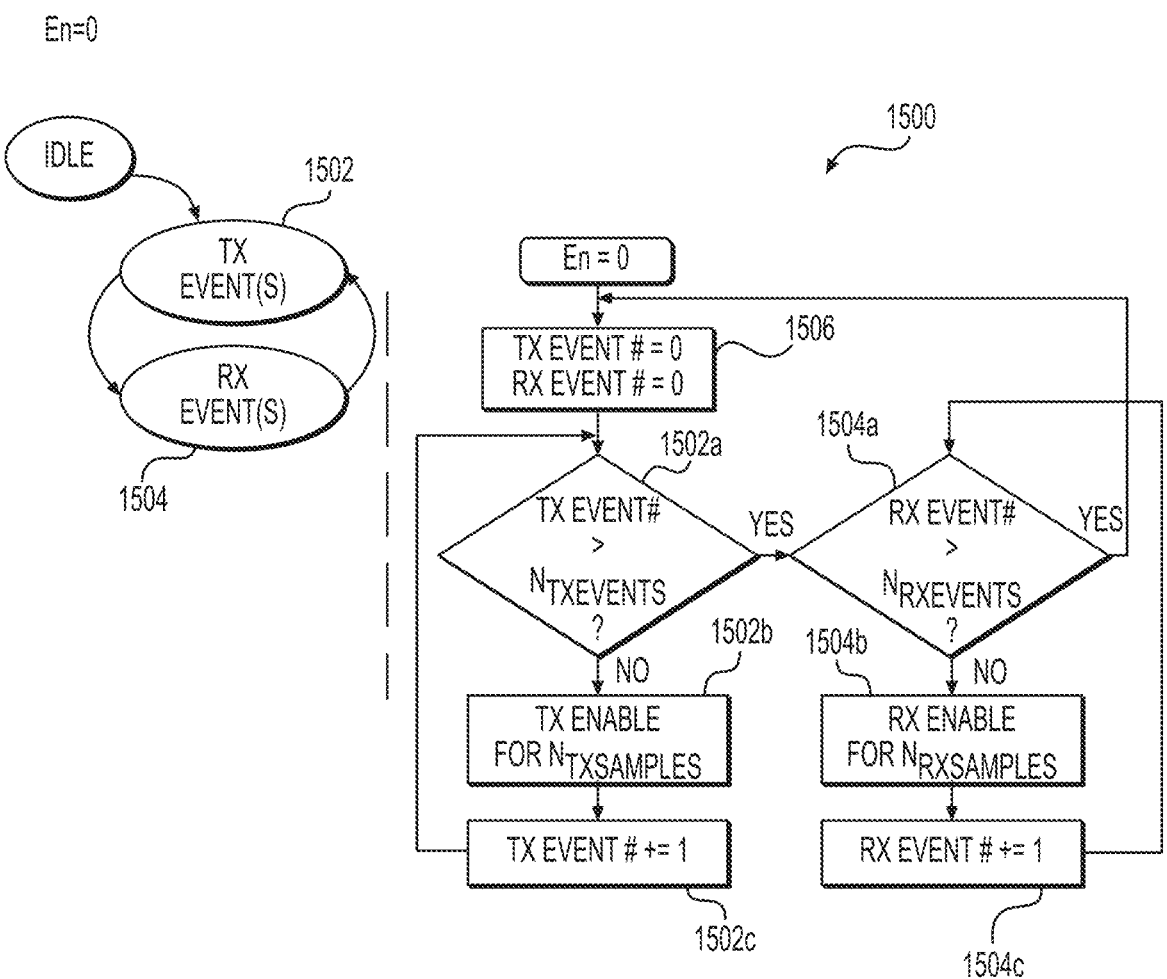
FIG. 15A shows an illustrative example of a routine that may be performed by the event controller shown in FIG. 14 so as to generate a suitable sequence of outputs for controlling transmission and/or reception events.

FIG. 15A shows an illustrative example of a routine 1500 that may be performed by the event controller 1302 so as to generate a suitable sequence of outputs for controlling transmission and reception events. The flowchart on the left-hand side of FIG. 15A is an abstraction of the example routine illustrated by the flowchart on the right-hand side of that figure. As shown, when the enable signal "En" is high, the routine alternates between performing a TX event subroutine 1502 and an RX event subroutine 1504, until the enable signal "En" transitions to low. In the example routine shown, after being enabled, the routine 1500 first initializes the TX and RX event numbers to "0" (step 1506), and then proceeds with the TX event subroutine 1502a-c. The TX event subroutine 1502 causes the TX enable signal to be high for the number of samples specified by the $N_{TXSamples}$ parameter (step 1502b), and increments the TX event number by one (step 1502c) until the current TX event number exceeds the value of the $N_{TXEvents}$ parameter (step 1502a). When the current TX event number exceeds the value of the $N_{TXEvents}$ parameter (step 1502a), the routine 1500 proceeds to the RX event subroutine 1504.

The RX event subroutine 1504 causes the RX enable signal to be high for the number of samples specified by the $N_{RXSamples}$ parameter (step 1504b), and increments the RX event number by one (step 1504c) until the current RX event number exceeds the value of the $N_{RXEvents}$ parameter (step 1504a). When the current RX event number exceeds the value of the $N_{RXEvents}$ parameter (step 1504a), the routine 1500 returns to the step 1506, at which the TX and RX event numbers are again initialized to "0." before beginning the TX subroutine 1502 once again. By using a routine such as that shown in FIG. 15A, the event controller 1302 is able to interact with the TX control circuits 104 in a device 100 so that any number of the transducer elements 304 can fire a pulse at a time, and is able to interact with the RX control circuits 106 so that an acquisition window can be acquired in a specified manner.

Possible operating modes of the event controller 1302 using the routine 1500 include (1) single transmit event/ single receive event, (2) multiple transmit events/single receive event, (3) single transmit event/multiple receive events, and (4) multiple transmit events/multiple receive events. In some embodiments, for example, in connection with a backscatter mode of operation, it may be desirable to follow each TX event with a corresponding RX event, rather than cycling through a number of TX events and then cycling through a number of RX events. Furthermore, for more complex events (e.g., a shear wave backscatter event), it may be desirable to cycle through a number of TX events followed by a single RX event during each iteration of the subroutines 1502, 1504. These are just a few possible event control methodologies, however, and other sequences of events are possible and contemplated.

Figure 13B:
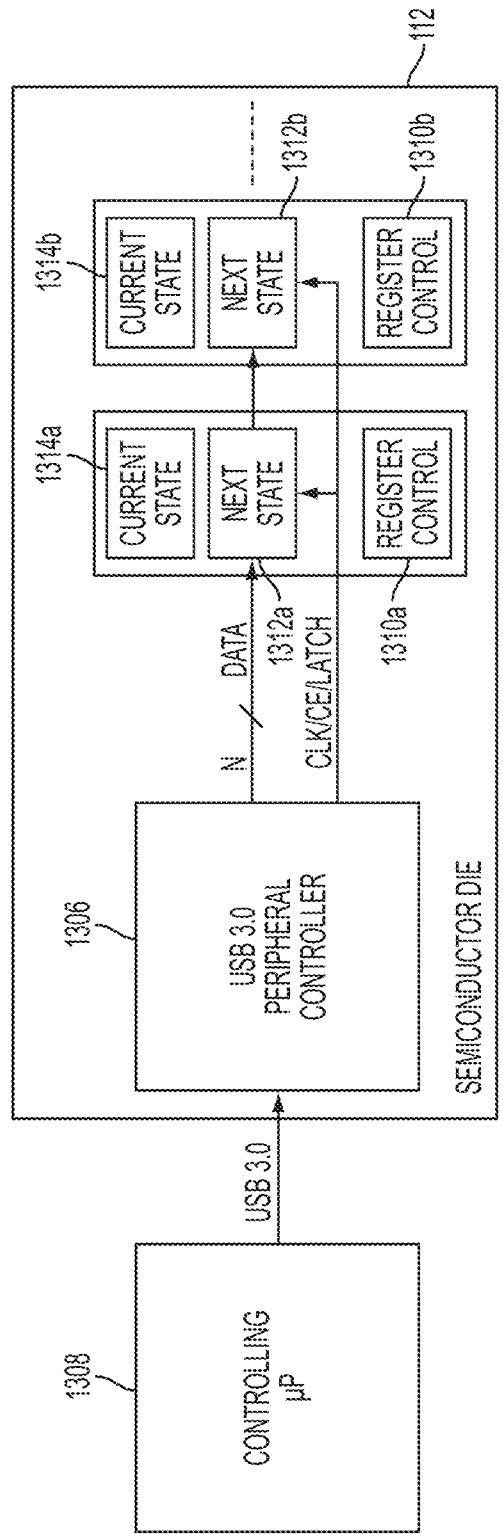
FIG. 13B shows an example of components that may be used to selectively determine values for one or more of the operational parameters used by the TX control circuits and/or the RX control circuits

FIG. 13B shows another example of components that may be used to selectively determine values for one or more of the operational parameters used by the waveform generator 1006 in the embodiments of FIGS. 12A-B (e.g., "θ," "$f_o$," "r," "$V0_{LOW}$," "$V0_{HIGH}$," "$V1_{HIGH}$," and/or "$V1_{LOW}$") and/ or values for one or more operational parameters for the RX control circuit 106, e.g., to control the LNA 1702, VGA 1704, etc. (discussed below in connection with FIGS. 17, 22, 24, 26, 27, 29, and 30). Such values may, for example, be stored in a set of "next state" registers 1312a-b and a corresponding set of "current state" registers 1314a-b for each transducer element 304.

As shown, a peripheral control module 1306, e.g., a USB 3.0 peripheral controller, may be integrated on the semiconductor die 112 so as to allow an external microprocessor 1308 to selectively communicate new values to the next state registers 1302 associated with some or all of the transducer elements 304 in an array 102. In some embodiments, each group of state registers 1312, 1314 may be controlled by a corresponding register control module 1310a-b. As shown, in some embodiments, the register control modules 1310a-b may be daisy chained from one register control module 1310 to the next.

Figure 15B:
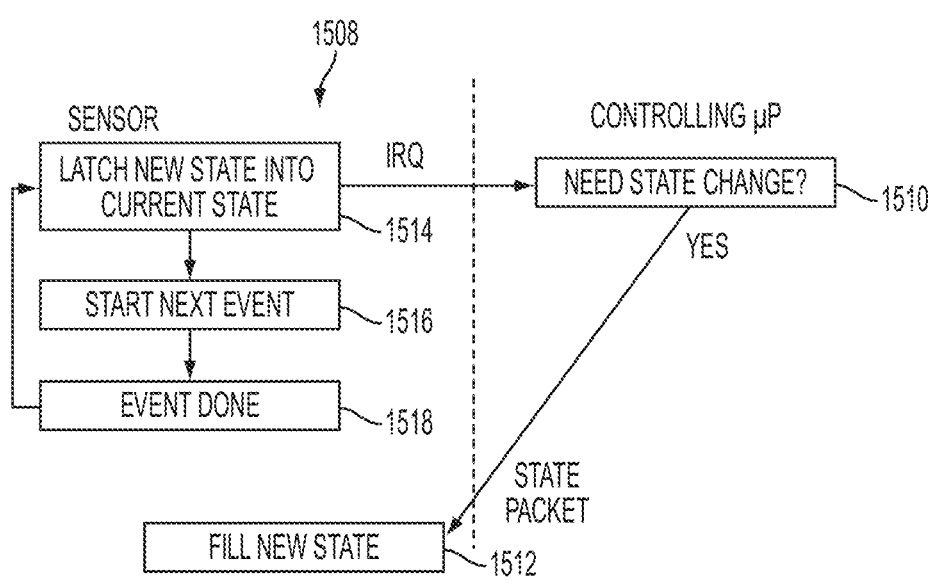
FIG. 15B shows an illustrative example of a routine that may be employed in connection with the embodiment of FIG. 13A to selectively determine values for one or more of the operational parameters used by the TX control circuits and/or the RX control circuits.

FIG. 15B shows an example of a routine 1508 that may be followed to selectively configure the registers 1312, 1314 in some embodiments. As shown, the microprocessor 1308 may, for example, receive an interrupt signal IRQ over the USB 3.0 link prior to each frame. Upon receiving such an interrupt, the microprocessor 1308 may determine whether the state of the current registers 1314 needs to be changed for the next event (see step 1510). If the microprocessor 1308 determines that the state should change, it may push a new complete sequence down the chain (see step 1512) and latch the new values into the next state registers 1312. The new values in the next state registers 1312 may then be latched into the current state registers 1302 on the frame boundary (see step 1514) for use in executing the next event (sec steps 1516 and 1518). The above process may then be repeated to latch any desired new values into the next state registers 1312. Using such a technique to selectively control operational parameters of the TX control circuit 104 and/or the RX control circuit 106, may, for example reduce the required local memory requirements on the die 112, and may allow every pulse to have a unique definition with any arbitrary combination since the microprocessor 1308 may have fewer resource constraints than the sensor 102.

Figure 16:
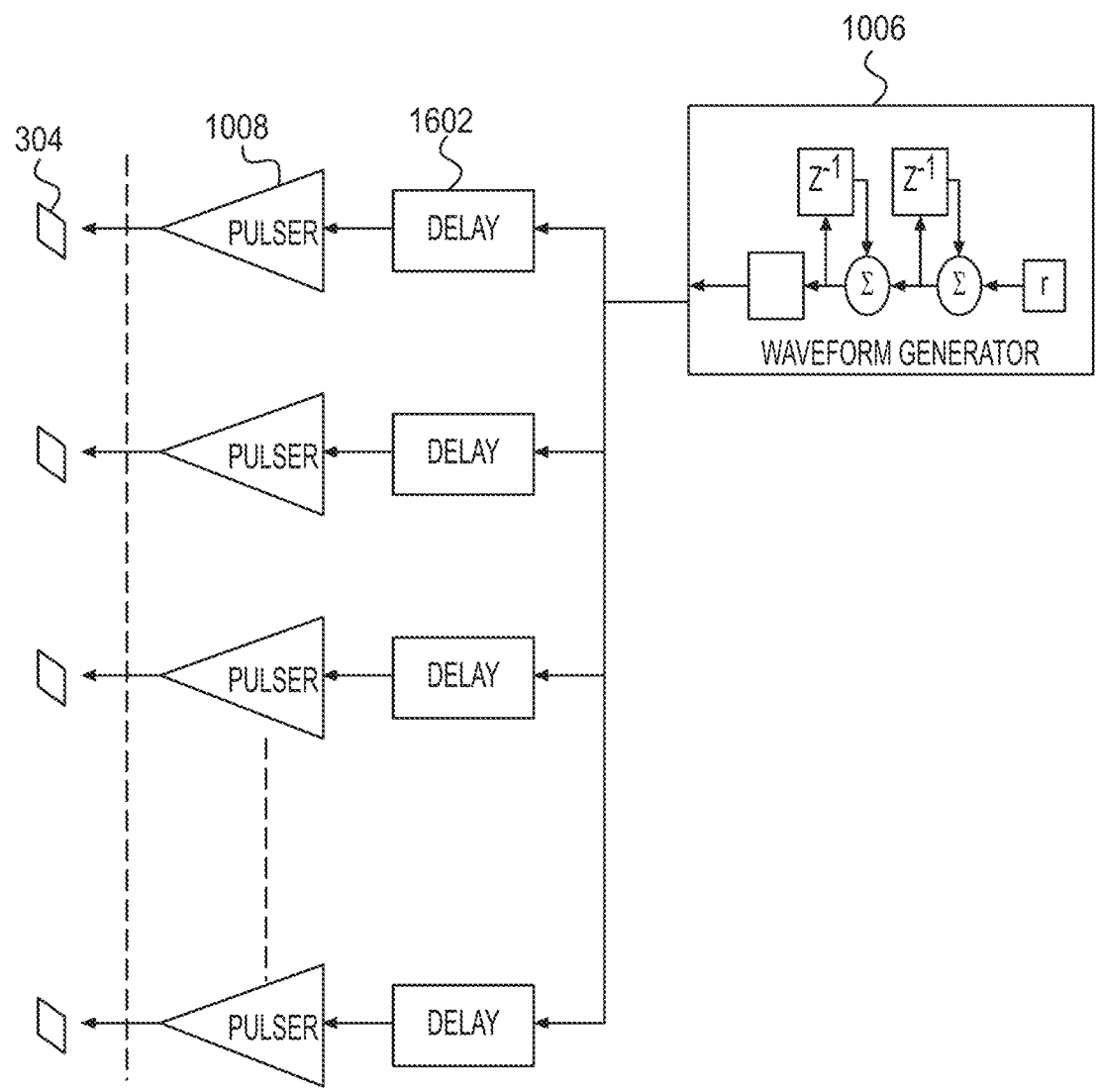
FIG. 16 shows an alternative implementation of an ultrasound device in which a single waveform generator may be shared by two or more TX control circuits.

FIG. 16 shows an alternative implementation of an ultrasound device 100 in which a single waveform generator 1006 may be shared by two or more TX control circuits 104. The shared waveform generator 1006 may, for example, be included in the timing & control circuit 108. As shown, rather than using the timing & control circuit 108 to selectively enable the TX control circuits 104 in a desired sequence, delay elements 1602 may be disposed between the shared waveform generator 1006 and the respective pulsers 1008 in the TX control circuits 106, with the delay elements 1602 being selected so as to cause the output of the shared waveform generator 1006 to reach the respective pulsers 1008 according to a desired timing sequence. The delay elements 1008 may, for example, be located in the TX control circuits 104, in the timing & control circuit 108, or elsewhere. Using the illustrated technique, the transducer elements 304 of an array 102 may be pulsed according to any desired timing sequence, as determined by the delays provided by the respective delay elements 1602.

Figure 17:
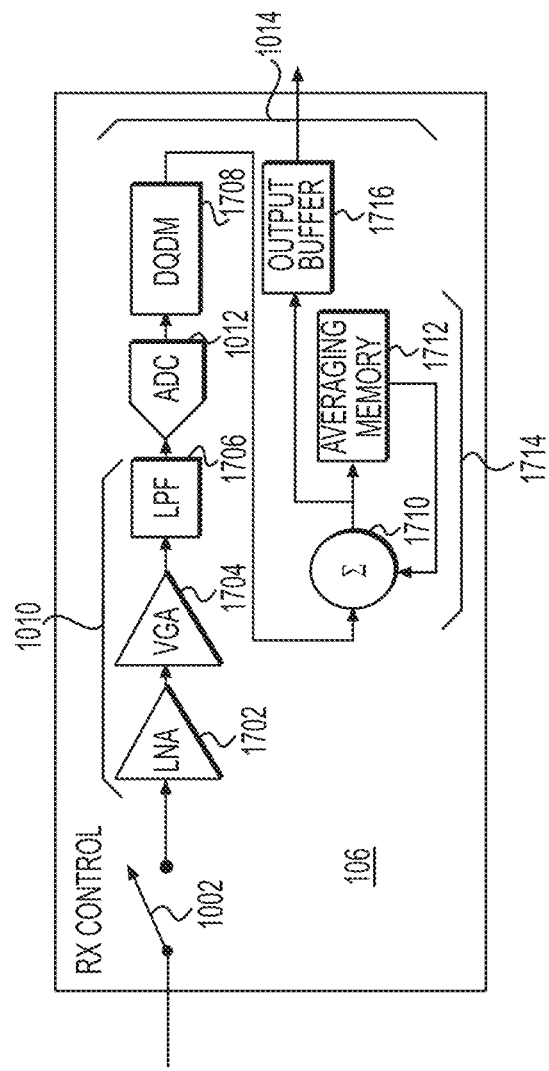
FIGS. 17-18 and 22-28 show illustrative examples of components that may be included within the analog processing block and the digital processing block of the RX control circuit shown in FIG. 10.

FIG. 17 shows an illustrative example of components that may be included within the analog processing block 1010 and the digital processing block 1014 of each RX control circuit 106 (see FIG. 10). In some embodiments, the components of the RX control circuit 106 may, for example, collectively have a bandwidth from DC to 50 MHz and provide a gain of 50 dB. with a noise figure of less than 4 dB, aliased harmonic rejection of 45 dB, and channel isolation of 40 dB. Such parameters are listed for illustrative purposes only and are not intended to be limiting. Other performance parameters are possible and contemplated.

As shown in FIG. 17, the analog processing block 1010 may, for example, include a low-noise amplifier (LNA) 1702, a variable-gain amplifier (VGA) 1704, and a low-pass filter (LPF) 1706. In some embodiments, the VGA 1704 may be adjusted, for example, via a time-gain compensation (TGC) circuit 1902 (shown in FIG. 19) included in the event controller 1302 of the timing & control circuit 108. The LPF 1706 provides for anti-aliasing of the acquired signal. In some embodiments, the LPF 1706 may, for example, comprise a 2nd order low-pass filter having a frequency cutoff on the order of 5 MHz. Other implementations are, however, possible and contemplated. As noted above, the ADC 1012 may, for example, comprise a 10-bit, 20 Msps, 40 Msps, or 80 Msps ADC.

Figure 18:
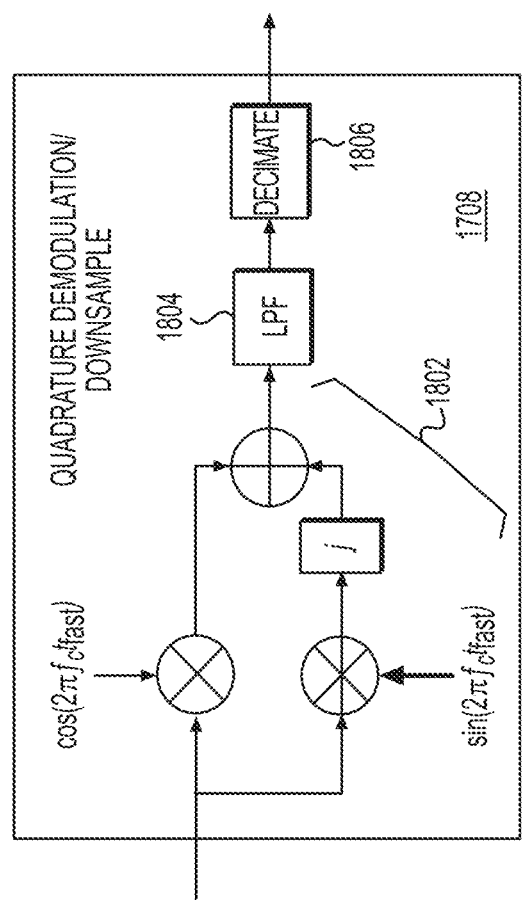

In the example of FIG. 17, the digital control block 1014 of the RX control circuit 106 includes a digital quadrature demodulation (DQDM) circuit 1708, an averaging circuit 1714 (including an accumulator 1710 and an averaging memory 1712), and an output buffer 1716. The DQDM circuit 1708 may, for example, be configured to mix down the digitized version of the received signal from center frequency to baseband, and then low-pass filter and decimate the baseband signal. An illustrative example of a quadrature demodulation circuit that may be employed as the DQDM 1708 is shown in FIG. 18. As shown, the DQDM 1708 may, for example, include a mixer block 1802, a low-pass filter (LPF), and a decimator circuit 1806. The illustrated circuit may allow for a lossless reduction of bandwidth by removing unused frequencies from the received signal, thus significantly reducing the amount of digital data that needs to be processed by the signal conditioning/processing circuit 110 and offloaded from the die 112. The bandwidth reduction achieved by these components may help to facilitate and/or improve the performance of the "ultrasound-on-a-chip" embodiments described herein.

In some embodiments, it may be desirable to match the center frequency "fe" of the mixer block 1802 with the frequency of interest of the transducer cells 602 that are used in the array(s) 102. Examples of additional components that may, in some embodiments, be included in RX control circuits 106, in addition to or in lieu of the DQDM 1708 and/or the other components illustrated in FIG. 17 are described below in connection with FIGS. 22-28. The averaging block 1714 in the embodiment shown (including accumulator 1710 and averaging memory 1712) functions to average received windows of data.

Figure 19:
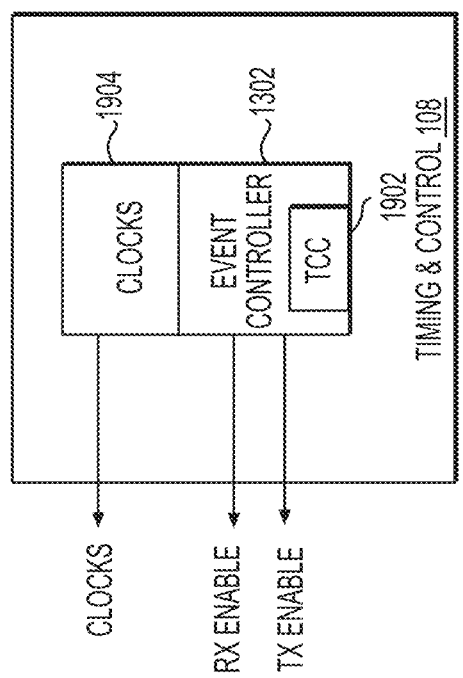
FIG. 19 shows an example implementation of the timing & control circuit shown in FIG. 1.
Figure 20:
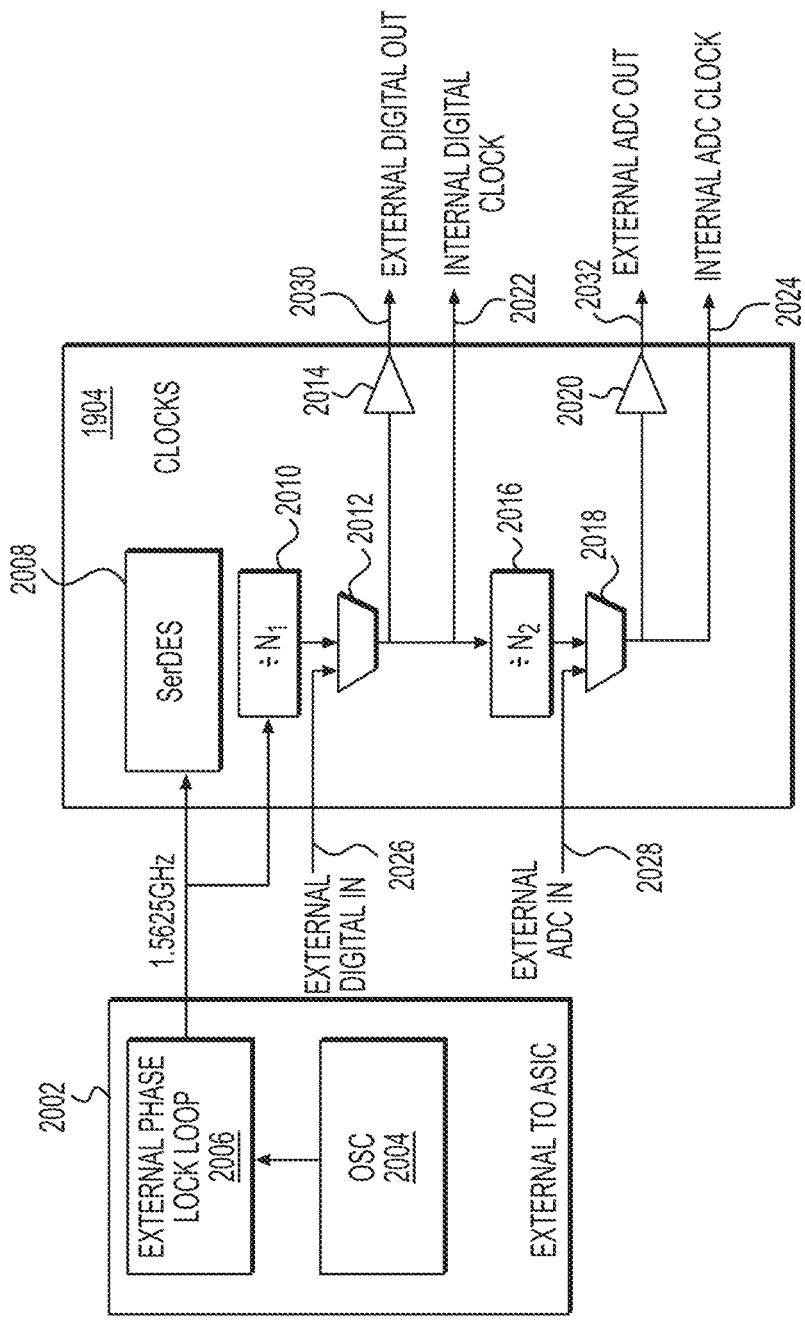
FIG. 20 shows an example implementation of the clock generation circuit shown in FIG. 19.

FIG. 19 shows an example implementation of the timing & control circuit 108. As shown, in some embodiments, the timing & control circuit 108 may include both a clock generation circuit 1904, and an event controller 1302. The clock generation circuit 1904 may be used, for example, to generate some or all of the clocks used throughout the device 100. An example implementation of the clock generation circuit 1904 is shown in FIG. 20. As shown, in some embodiments, an external circuit 2002 may be used to generate a high-speed (e.g., 1.5625 GHz) clock, e.g., using an oscillator 2004 and a phase lock loop (PLL) 2006, that can be fed to the clock generation circuit 1904. In addition to being fed to serializer/deserializer (SerDes) circuitry 2008, the clock may be stepped down (e.g., via frequency divider circuit 2010) to a first frequency for use for clocking certain components on the die 112, and may be further stepped down (e.g, via frequency divider circuit 2016) to a second frequency for use by other components on the die 112. In some embodiments, for example, the frequency divider circuit 2010 may divide the 1.5625 GHz clock so as to yield a 40 MHz clock on the clock line 2022 for use within the die 112, and the frequency divider circuit 2016 may further divide the 40 MHZ clock so as to yield a 20 MHz clock on the clock line 2024 for use within the die.

As shown, in some embodiments, the die 112 may have terminals 2026, 2028 connected to inputs of multiplexers 2012, 2018, respectively, to accept clock signals from external sources, and may additionally have output terminals 2030, 2032 connected to the outputs of the multiplexers 2012, 2018, respectively, to allow clock signals to be fed off-chip. By appropriately controlling the multiplexers, this configuration can allow multiple chips to be synchronized by daisy chaining clocks. Thus, for some implementations, this technique allows multiple devices 100 to be extended into a fully synchronized, coherent M×N array of devices 100 that can operate as a unit to image a subject.

Returning to FIG. 19, one illustrative example an event controller 1302 that may be included in the timing & control circuit 108 is described above in connection with FIG. 13A. As shown in FIG. 19, however, in some embodiments, the event controller 1302 may additionally comprise a TGC circuit 1902 that may be used, for example, to control the gain of the VGAs 1704 in the analog processing blocks 1010 of the RX control circuits 106.

Figure 21:
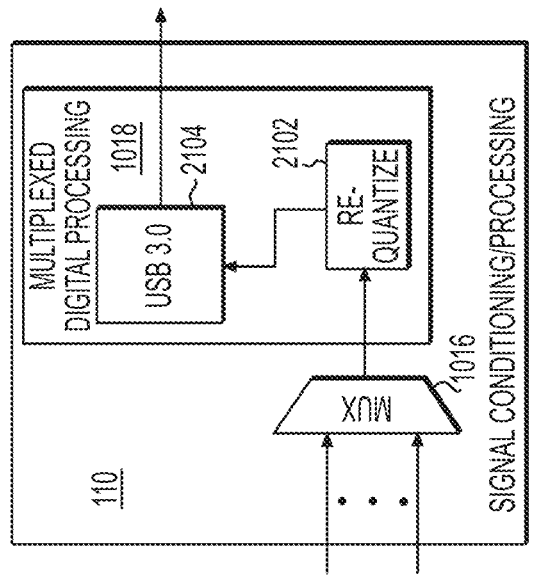
FIG. 21 shows an illustrative example of components that may be included in the multiplexed digital processing block of the signal conditioning/processing circuit shown in FIG. 10.

FIG. 21 shows an illustrative example of components that may be included in the multiplexed digital processing block 1018 of the signal conditioning/processing circuit 110 on the die 112. As shown, the multiplexed digital processing block 1018 may, for example, include a re-quantizer 2102 and a USB 3.0 module 2104. In some embodiments, the re-quantizer 2102 may, for example, perform lossy compression to provide bandwidth reduction. The re-quantizer 2102 may operate in any of numerous ways, and aspects of the present technology do not necessarily require the use of any particular type of re-quantization technique. In some embodiments, the re-quantizer 2102 may, for example, find a maximum magnitude of the incoming signal, scale all signals up to make the maximum signal full-scale, and then throw away the lower N-bits from the signal. In other embodiments, the re-quantizer 2102 may additionally or alternatively covert the signal to log space and keep only N bits of the signal. In yet other embodiments, the re-quantizer 2102 may additionally or alternatively employ Huffman coding and/or vector quantization techniques.

As shown in FIG. 21, one option for outputting a high-speed serial data stream from the die 112 is a USB 3.0 module. Details as to the structure and operation of such a USB 3.0 module are described, for example, in the Universal Serial Bus Revision 3.0 Specification, available at http://www.usb.org, the entire content of which is incorporated herein by reference. Although FIG. 21 illustrates the use of a USB 3.0 module to provide a high-speed serial data stream from the chip, it should be appreciated that other data output techniques may additionally or alternatively be employed. For example, one or more 10 GB, 40 GB, or 100 GB Ethernet modules may additionally or alternatively be employed. In other embodiments, other high-speed parallel or high-speed serial data output modules and/or techniques may additionally or alternatively be employed.

Figure 22:
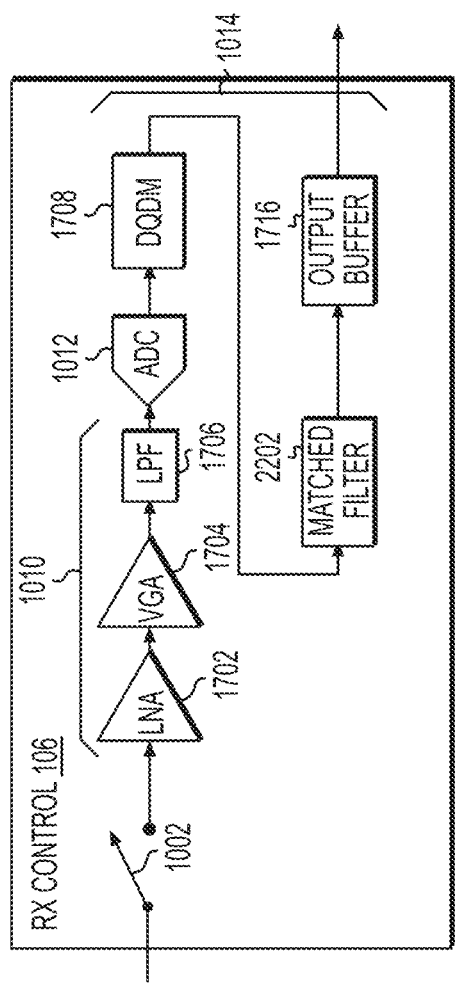

FIG. 22 shows an example implementation of the RX control circuit 106 that includes a matched filter 2202 that may, for example, perform waveform removal and improve the signal-to-noise ratio of the reception circuitry. Although labeled a "matched" filter, the filter circuit 2202 may actually operate as either a matched filter or a mismatched filter so as to decouple waveforms from the received signal. The matched filter 2202 may work for either linear frequency modulated (LFM) or non-LFM pulses.

Figure 23:
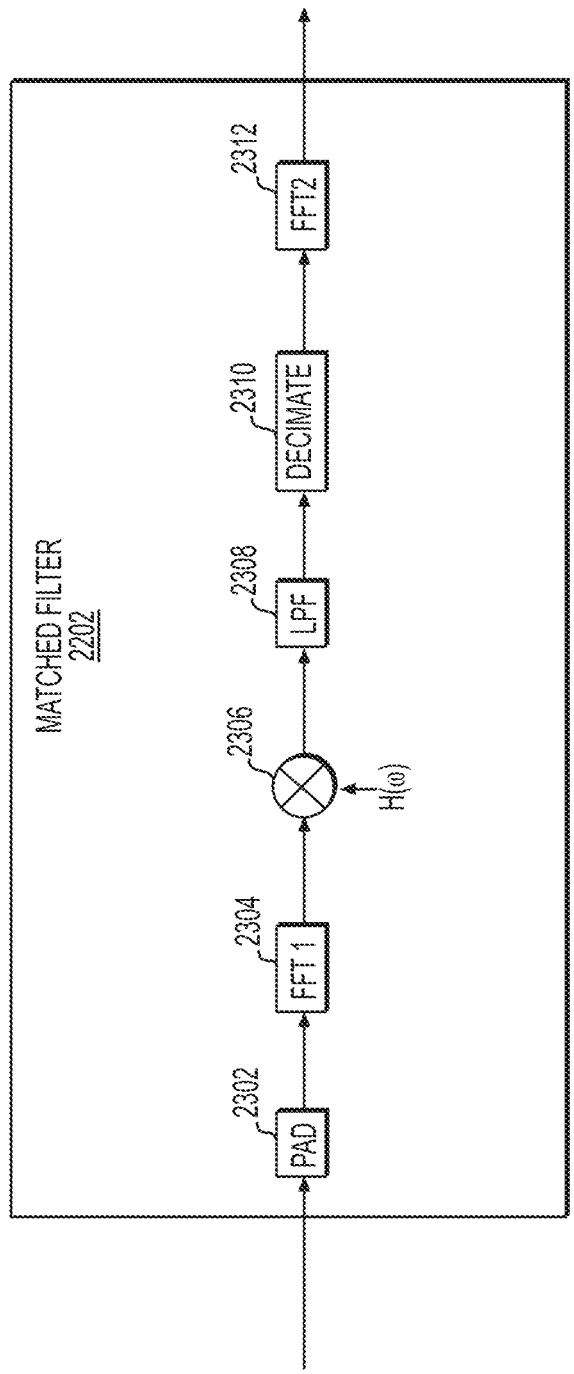

An illustrative embodiment of a circuit suitable for use as the matched filter 2202 is shown in FIG. 23. As shown, the matched filter 2202 may, for example, include a padding circuit 2302, a fast Fourier transformation (FFT) circuit 2304, a multiplier 2306, a low-pass filter 2308, a decimator circuit 2310, and an inverse FFT circuit 2312. If employed, the padding circuit 2302 may, for example, apply padding to the incoming signal sufficient to avoid artifacts from an FFT implementation of circular convolution.

To operate as a "matched" filter, the value of "$H(\omega)$" applied to the multiplier 2306 should be a conjugate of the transmission waveform $T_x(\omega)$. In some embodiments, the filter 2202 may thus indeed operate as a "matched" filter, by applying a conjugate of the transmission waveform $T_x(\omega)$ to the multiplier 2306. In other embodiments, however, the "matched" filter 2202 may instead operate as a mismatched filter, in which case some value other than a conjugate of the transmission waveform $T_x(\omega)$ may be applied to the multiplier 2206.

Figure 24:
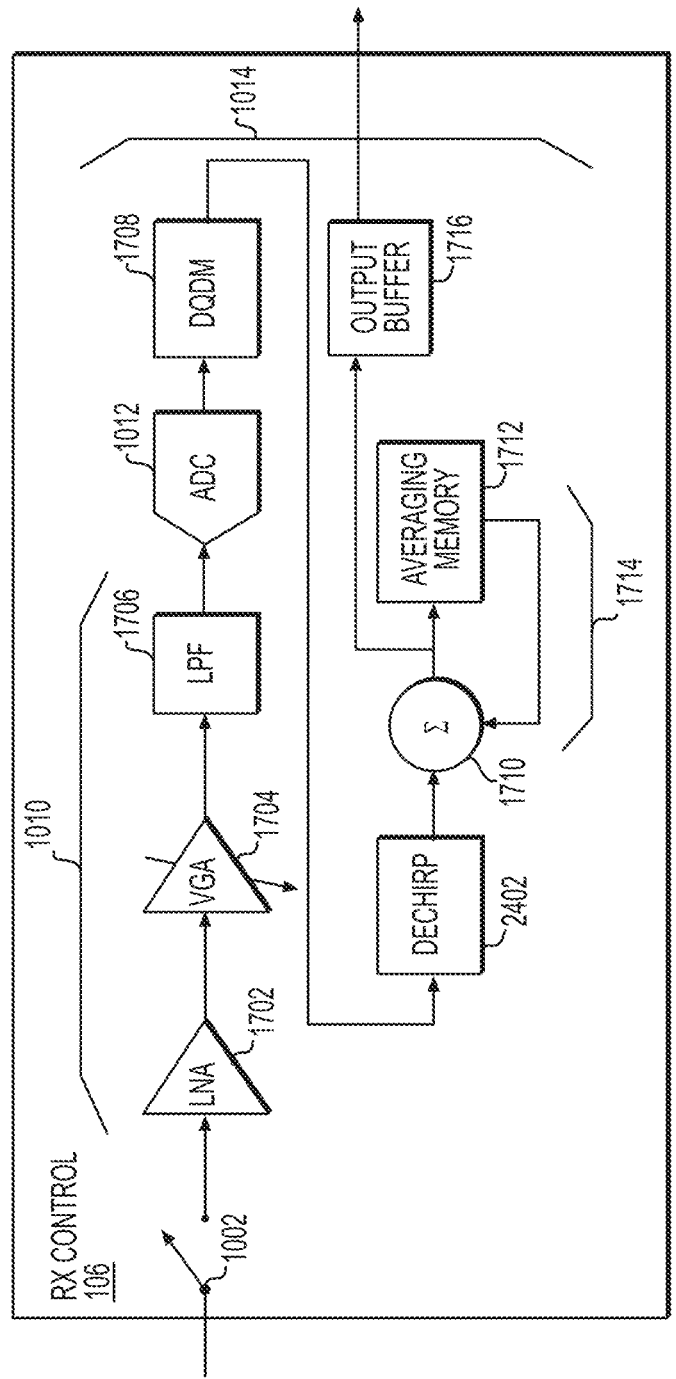

FIG. 24 shows another example implementation of the RX control circuit 106. In the FIG. 24 embodiment, the RX control circuit 106 includes a dechirp circuit 2402 that can perform yet another technique to reduce bandwidth by isolating signals of interest. Dechirp circuits as also sometimes referred to as "digital ramp" or "stretch" circuits. In various embodiments, a dechirp circuit 2402 may be included within the analog processing block 1010, or may be included within the digital processing block 1014 of the RX, or may be included in both the analog processing block 1010 and the digital processing block 1014 of the RX control circuit 106. Using a dechirp circuit with an LFM waveform effectively converts time to frequency.

Figure 25:
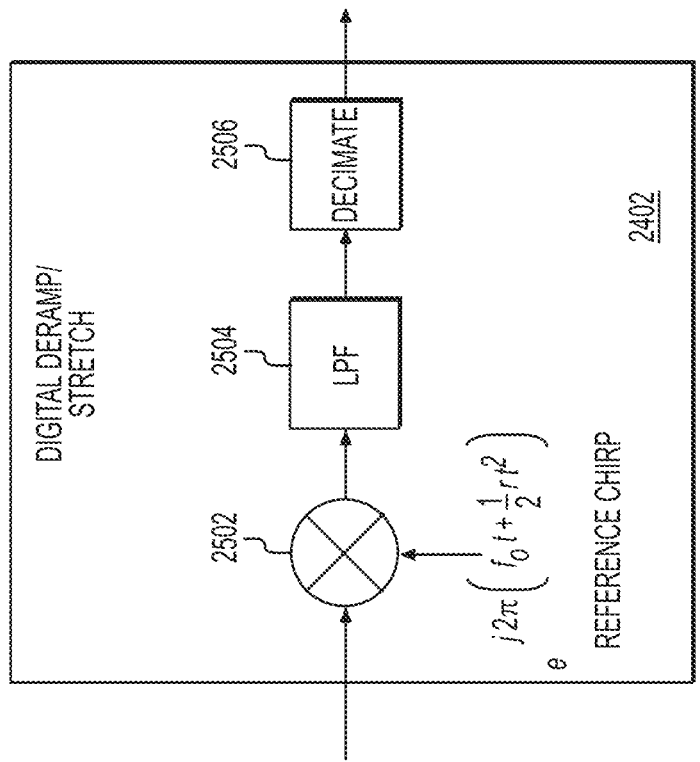

An example of a digital dechirp circuit 2402 is shown in FIG. 25. As shown, the dechirp circuit 2402 may include a digital multiplier 2502, a digital low pass filter 2504, and a decimator circuit 2506. (An analog dechirp circuit—discussed below in connection with FIG. 26—would employ an analog multiplier and filter, rather than a digital multiplier and filter, and would not include the decimator circuit 2506). The "reference chirp" shown in FIG. 25 may, for example, be the same "chirp" as that generated by the waveform generator 1006 in the corresponding TX control circuit 104.

Figure 26:
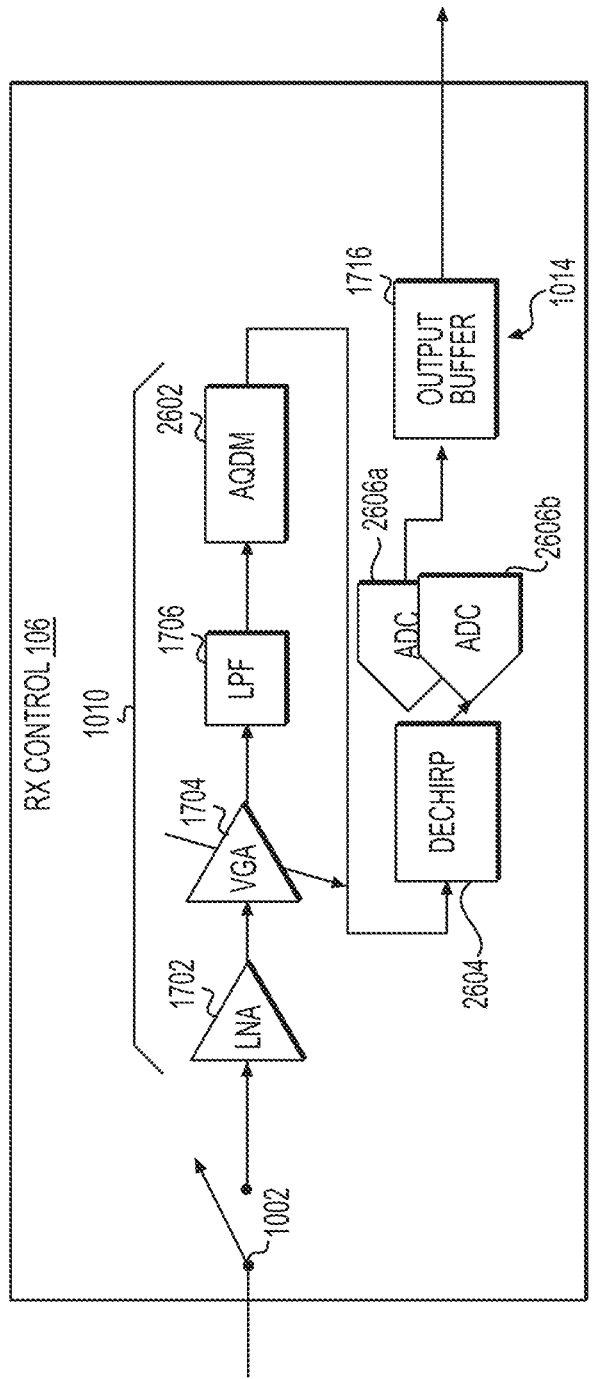

FIG. 26 shows yet another example implementation of an RX control circuit 106. In this example, rather than using a DQDM circuit and a digital dechirp circuit in the digital processing block 1014, an analog quadrature demodulation (AQDM) circuit 2602 and an analog dechirp circuit 2604 are included in the analog processing block 1010. In such an embodiment, the AQDM 2602 may, for example, employ an analog mixer (not shown) and a local oscillator (not shown) to mix the incoming signal to baseband and then employ a low-pass analog filter (not shown) to remove unwanted frequencies from the analog signal. As shown in FIG. 26, two ADCs 2606a-b (e.g., two 10-bit 10 Msps, 20 Msps, or 40 Msps ADCs) may be employed in this embodiment to convert the output of the analog dechirp circuit 2604 into a digital signal format, but each of the ADCs 2606a-b may run at half the rate as the ADC 1012 employed in the other examples, thus potentially reducing power consumption.

Figure 27:
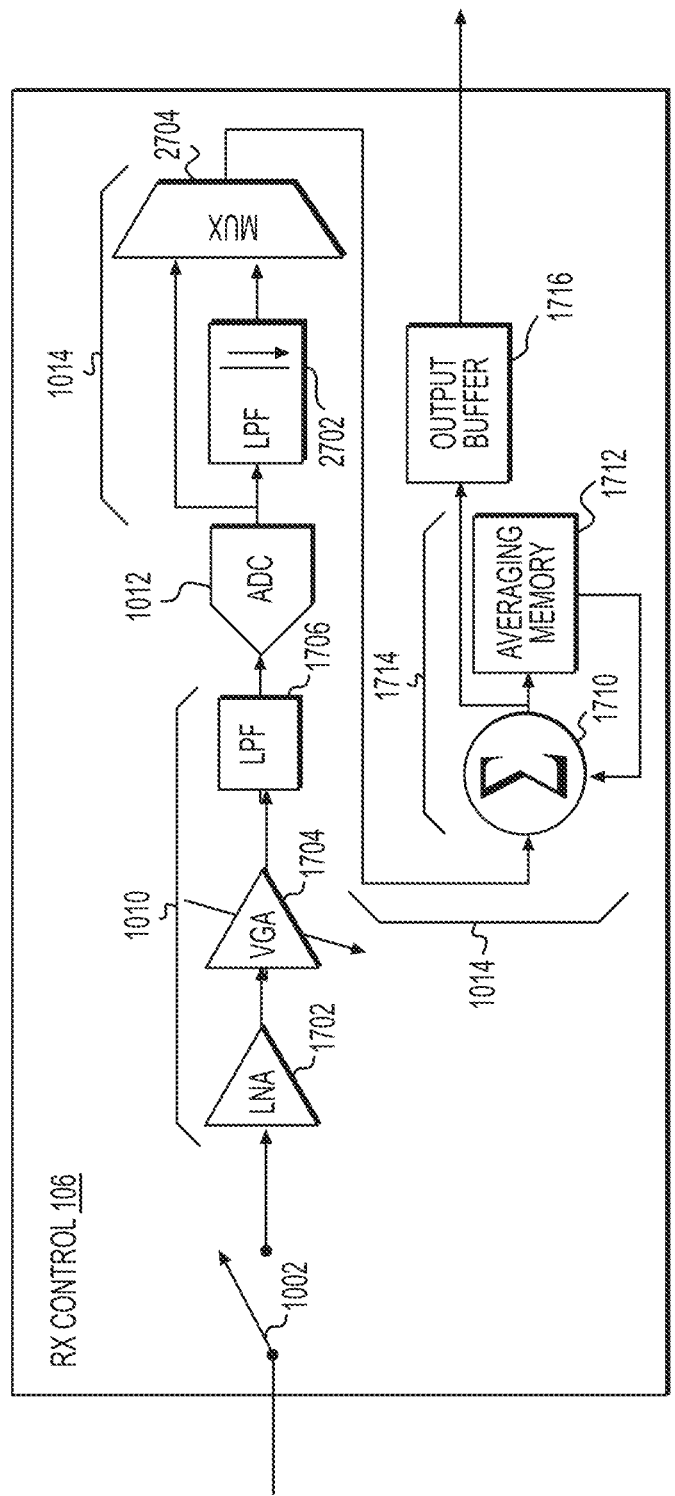
Figure 28:
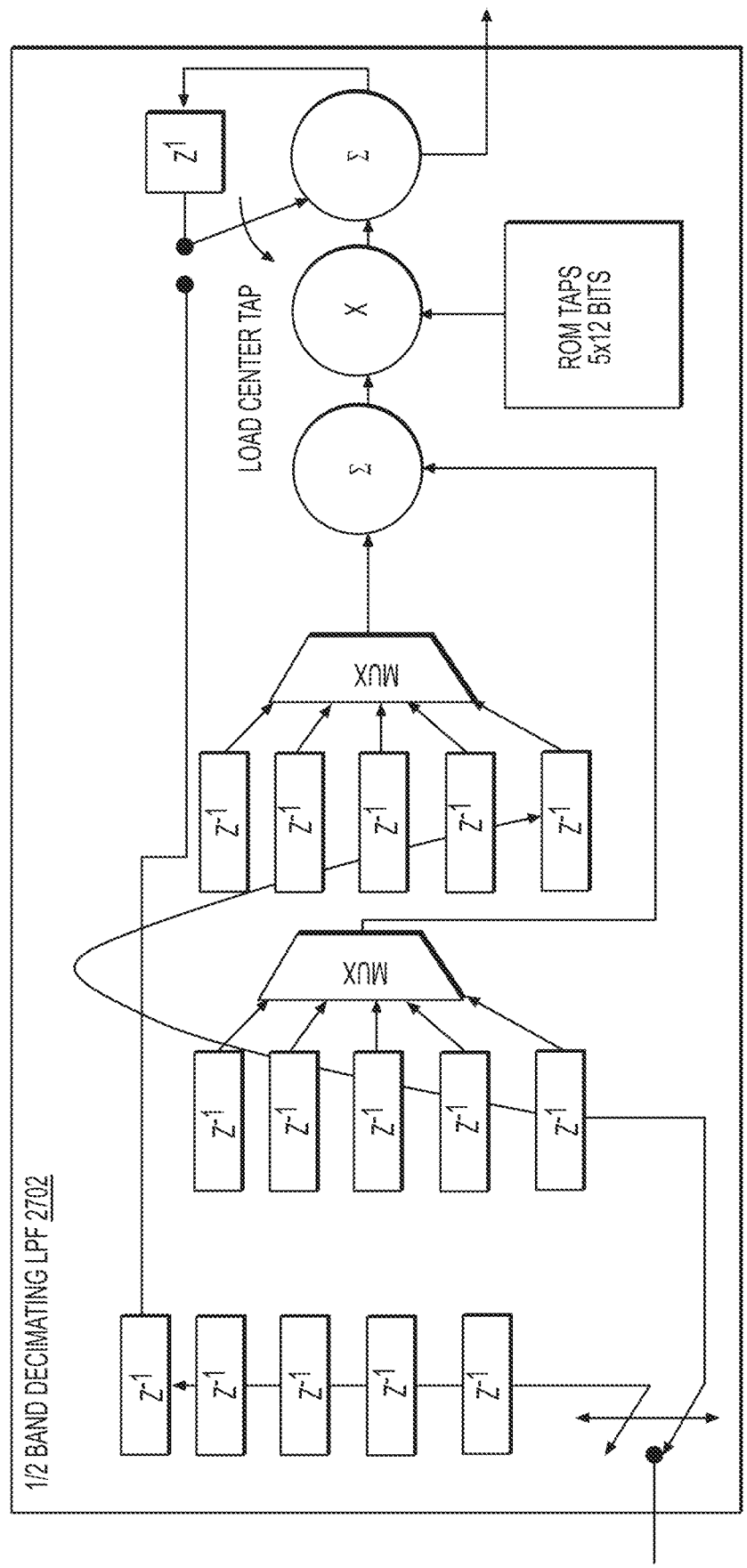

Still another example of an RX control circuit 106 is shown in FIG. 27. In this example, a low-pass filter 2702 and multiplexer 2704 are included in the digital processing block 1014, together with an averaging block 1714. In some embodiments, the low-pass filter 2702 may, for example, include a ½ band decimating finite impulse response (FIR) filter, and its operation may be configured to minimize the number of non-zero taps. An illustrative example of such a FIR filter 2702 is shown in FIG. 28.

It should be appreciated that, in various embodiments, each RX control circuit 106 may use any of the foregoing analog and digital circuit elements either alone or in combination with any of the other described circuit elements, and aspects of the present technology do not necessarily require the specific configurations and/or combinations illustrated herein. For example, each RX control circuit 106 may, in some embodiments, include any one or more of an AQDM 2602, an analog dechirp circuit 2604, a DQDM 1708, a matched and/or unmatched filter 2202, a digital dechirp circuit 2402, an averaging block 1714, and a low-pass filter 2702, in any combination and in any order with respect to the other components, provided analog-to-digital and/or digital-to-analog conversion is performed, as necessary. Importantly, the use of any or all of the above-described bandwidth reduction techniques may, for some embodiments, help make the "ultrasound-on-a-chip" designs described herein a practical, viable, and commercially feasible solution.

Figure 29:
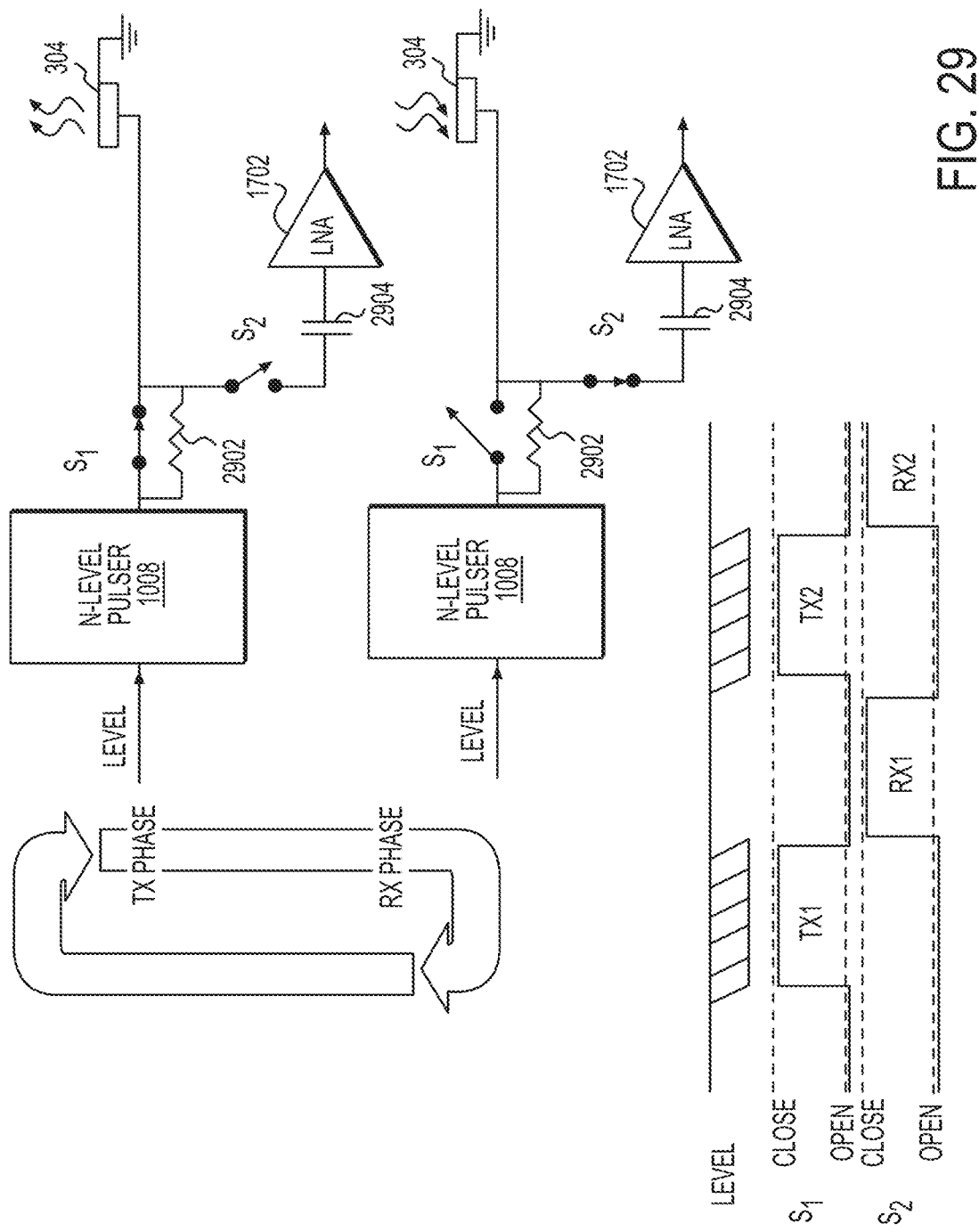
FIGS. 29-30 illustrate examples of techniques for biasing transducer elements in an array or other arrangement.

FIG. 29 illustrates an example of a novel technique for biasing the transducer elements 304 in an array 102. As shown, the side of each of the transducer elements 304 that faces the patient may be connected to ground, so as to minimize risk of electric shock. The other side of each transducer element 304 may be connected to the output of the pulser 1008 via a resistor 2902. Accordingly, each transducer element 304 is always biased via the output of the pulser 1008, regardless of whether the switch S1 is open or closed. In some embodiments, e.g., embodiments employing transducer elements 304 comprising one or more CUTs or CMUTs, the bias voltage applied across the element may be on the order of 100V.

As illustrated in the accompanying timing diagram of FIG. 29, the switch S1 may be closed during a transmit operation and may be open during a receive operation. Conversely, the switch S2 may be closed during a receive operation and may be open during a transmit operation. (Note that there is always a gap between the opening of switch S1 and the closing of switch S2, as well as between the opening of switch S2 and the closing of switch S1, so as to ensure the pulser 1008 does not apply an outgoing pulse to the LNA 1702 in the RX control circuit 106.)

As also shown in the timing diagram, the pulser 1008 may hold the bottom plate of the transducer element 304 at its high output level at all times except when it is applying a waveform pulse to its transducer element 304, and the waveform pulse applied during the transmit phase may be referenced from the high output level of the pulser 1008. Accordingly, each individual pulser 1008 is able to maintain an ideal bias on its corresponding transducer element 304 at all times. As shown in FIG. 29, a capacitor 2904 may be placed between the switch S2 and the LNA 1702 of the RX control circuit 106 so as to block the DC bias signal (i.e., the high output of the pulser 1008) from reaching the LNA 1702 during receive operations (i.e., when switch S2 is closed).

Biasing the transducer elements 304 via their respective pulsers 1008 may provide benefits in some embodiments, such as reducing cross-talk that would otherwise occur if the elements 304 were biased via a common bus, for example.

Figure 30:
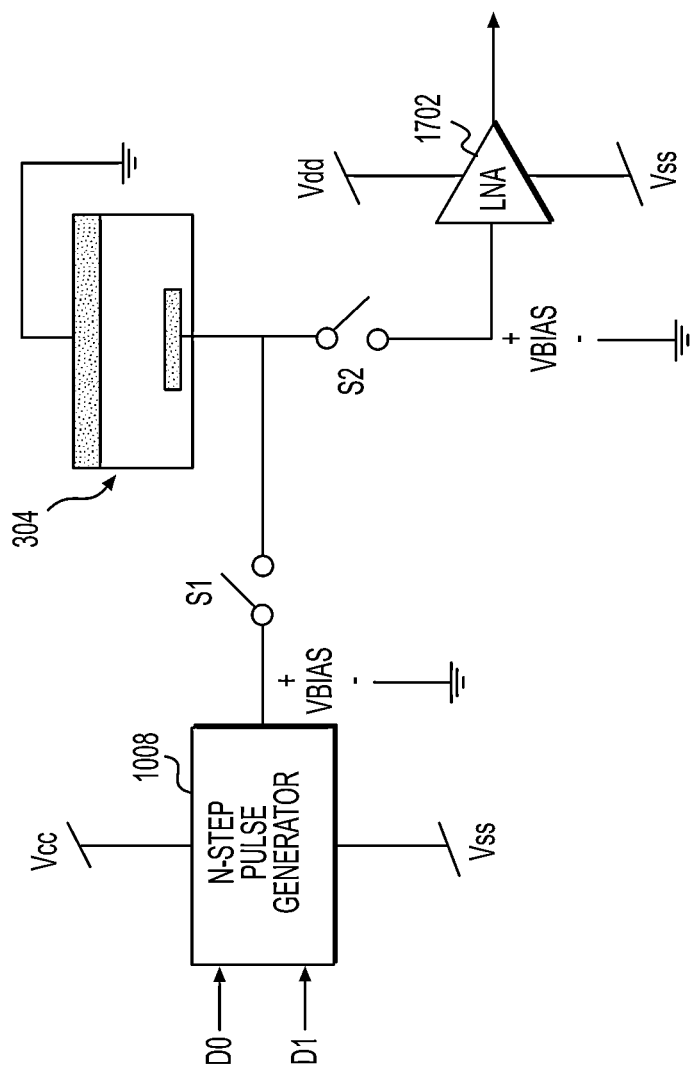

FIG. 30 shows another illustrative example of a technique for biasing the transducer elements 304 in an array 102. As with the embodiment of FIG. 29, the side of the transducer element 304 facing the patient may be grounded, and a switch S1 may be positioned between the output of the pulser 1008 and the other side of the transducer element 304. A switch S2 in this case may be positioned directly between the non-grounded side of the transducer element 304 and the LNA 1702 of a RX control circuit 106. In this example, a capacitor is not positioned between the switch S2 and the LNA 1702, thus resulting in a potentially significant savings of real estate on the die 112 that would otherwise be consumed by such capacitors. In some embodiments, one of the two switches, i.e., either switch S1 or switch S2 may always be closed. In transmit mode, switch S1 may be closed and switch S2 may be open. Conversely, in receive mode, switch S2 may be open and switch S1 may be closed.

To create the appropriate bias voltage at the output of each pulser 1008 and the input of each LNA 1702, as illustrated in FIG. 30, the entire die 112 (except for the portion that is used to bias the other side of the transducer elements 304, e.g., the top metal layer of the transducer array 102) may be biased at an optimal bias voltage for the transducer elements 304. This arrangement may thus facilitate safe high-voltage biasing of the transducer elements 304 via both the pulsers 1008 and the LNAs 1702 at all times. In some embodiments, the power supply of the chip may be floated so that it is not grounded, and some or all of the control, configuration, and communication inputs/outputs to the die 112 can be isolated, e.g., using optical isolation techniques or appropriately sized capacitors, thus DC blocking the high-voltage from leaving the chip.

Figure 31:
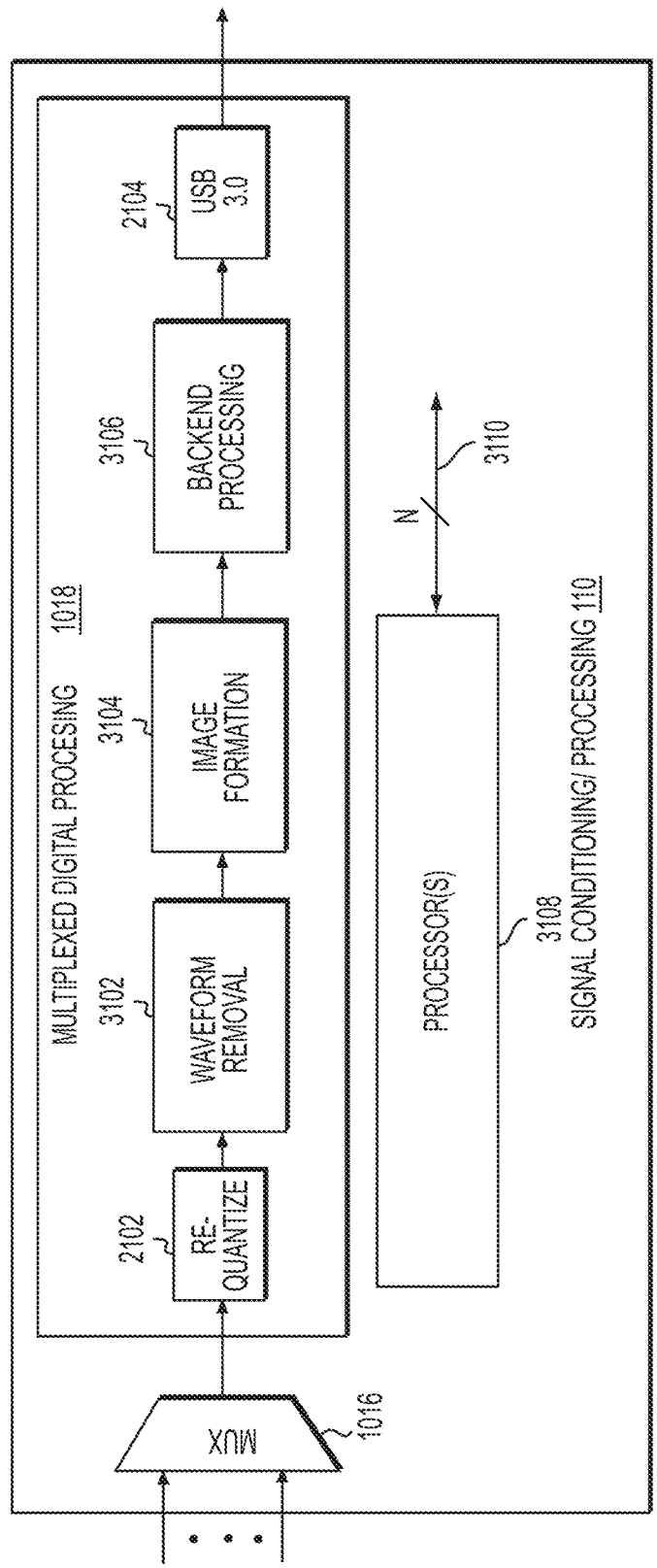
FIG. 31 shows examples of components that may be included in the multiplexed digital processing block of the signal conditioning/processing circuit shown in FIG. 10.

FIG. 31 shows an illustrative example of components that may be included in the multiplexed digital processing block 1018 of the signal conditioning/processing circuit 110 on the die 112, in addition to or in lieu of the components discussed above in connection with FIG. 10. In some embodiments, one or more of the illustrated components may be integrated on the die 112, together with some or all of the other circuitry described herein, provided a sufficiently small process is used for the CMOS or other integrated circuit fabrication methodology that is employed to fabricate the die 112.

In the example of FIG. 31, the signal conditioning/processing circuitry 110 includes a re-quantizer module 2102, a waveform removal circuit and/or software 3102, an image formation circuit and/or software 3104, a backend processing circuit and/or software 3106, and a USB 3.0 module 2104. As the re-quantizer module and USB 3.0 module, and alternatives thereto, were discussed above in connection with FIG. 21, those components will not be described further here. As shown, in some embodiments, one or more processors 3108, e.g. CPUs, GPUs, etc., and/or large-scale memories may be integrated on the die 112, together with the other circuitry discussed above, so as to enable some or all of the waveform removal functionality, image formation functionality, and/or backend processing functionality, as described below, to be implemented via software routines executed by such components, as well as to achieve other functionality of the other components of the device 100 described above. Accordingly, in such embodiments, the waveform removal module 3102, image formation module 3104, and/or backend processing module 3106 shown in FIG. 31 may be implemented partially or entirely via software stored in memory either on the die 112 or in one or more off-chip memory modules. In some embodiments, one or more high-speed buses 3110, such as those used by a unified Northbridge chip, or similar components may be employed to allow high-speed data exchange among the processors(s) 3108, memory modules, and/or other components either located on the die 112 or disposed at some off-chip location. In other embodiments, some or all of such functionality of the image formation module 3104, and/or backend processing module 3106 may additionally or alternatively be performed using one of more dedicated circuits integrated on the die 112.

In some embodiments, the waveform removal circuit and/or software 3102 may, for example, contain circuitry and/or software, similar to that discussed above in connection with the RX control circuits 106, to perform deconvolution of the waveform, dechirping, FFTs, FIR filtering, matched filtering and/or mismatched filtering, etc. Any or all of the foregoing functionality may be performed, either alone or together with any of the other functionality, in any order, by the waveform removal circuit and/or software 3102 on the die 112. Alternatively, in some embodiments, such waveform removal circuit and/or software 3102 may be separate from the die 112 but co-located with the die 112 in an ultrasound unit 200 and the same circuit board and/or in the same housing.

In some embodiments, the image formation circuit and/or software 3104 may, for example, contain circuitry and/or software configured to perform apodization, back projection and/or fast hierarchy back projection, interpolation range migration (e.g., Stolt interpolation) or other Fourier resampling techniques, dynamic focusing techniques, and/or delay and sum techniques, tomographic reconstruction techniques, etc. Any or all of the foregoing functionality may be performed, either alone or together with any of the other functionality, in any order, by the image formation circuit and/or software 3104 on the die 112. In some embodiments, the image formation circuit and/or software 3104 and the waveform removal circuit and/or software 3102 may both be located on the die 112. Alternatively, in some embodiments, such image formation circuit and/or software 3104 and/or the waveform removal circuit and/or software 3102 may be separate from the die 112 but co-located with the die 112 in an ultrasound unit 200 and the same circuit board and/or in the same housing.

In some embodiments, the backend processing circuit and/or software 3106 on the die 112 may, for example, contain circuitry and/or software configured to perform down-range and/or cross-range autofocusing, frequency dispersion compensation, non-linear apodization, remapping, compression, denoising, compounding, Doppler, elastography, spectroscopy, and/or basis pursuit techniques, etc. Any or all of the foregoing functionality may be performed, either alone or together with any of the other functionality, in any order, by the back-end processing circuit and/or software 3106 on the die 112. In some embodiments, the backend processing circuit and/or software 3106, the image formation circuit and/or software 3104, and/or the waveform removal circuit and/or software 3102 may all three be located on the die 112. Alternatively, in some embodiments, such backend processing circuit and/or software 3106, image formation circuit and/or software 3104, and/or the waveform removal circuit and/or software 3102 may be separate from the die 112 but co-located with the die 112 in an ultrasound unit 200 and the same circuit board and/or in the same housing.

In some embodiments, memory used to achieve some or all of the above-described functionality may be located on-chip, i.e., on the die 112. In other embodiments, however, some or all of the memory used to implement some or all of the described functionality may be located off-chip, with the remainder of the circuitry, software, and/or other components being located on the die 112.

Although not separately shown, it should be appreciated that, in some embodiments, some or all of the operational parameters of the timing & control circuit 108, the individual TX control circuits 104, the individual RX control circuits 106 and/or the signal processing/control circuit 110 may be selectively configured or programmed via one or more serial or parallel input ports to the die 112. For example, the timing & control circuit 110 may include a set of externally-writable registers containing values for the parameters $N_{TXSamples}$, $N_{TXEvents}$, $N_{RXSamples}$, and/or $N_{RXEvents}$ discussed above in connection with FIGS. 14 and 15; the registers 1202 of the TX control circuits 104 discussed above in connection with FIGS. 12A-B may be selectively programmed via one or more input ports; operational parameters of one or more of the components of the RX control circuit 106 discussed above in connection with FIGS. 17, 18, and 22-28 may be selectively programmed via one or more input ports; operational parameters for one or more of the re-quantizer circuit 2102 and/or USB 3.0 circuit 2104 or other modules discussed above in connection with FIG. 21 may be programmed via one or more input ports; and/or operational parameters for one or more of the waveform removal circuit 3102, image formation circuit 3104, and/or backend processing circuit 3106 discussed above in connection with FIG. 31 may be programmed via one or more input ports.

FIGS. 32A-B illustrate embodiments in which some or all of the waveform removal circuit and/or software 3102, the image formation circuit and/or software 3104, and/or the backend processing circuit and/or software 3106 may be located off-chip, e.g., on a computing device 3202, 3206 separate from the device 100. As shown in FIG. 32A, on a computing device 3202 not including one or more field-programmable gate arrays (FPGAs) 3208, waveform removal may be performed by software executed by the processor 3204 of the computing device 3202, together with image formation and backend processing functions. As shown in FIG. 32B, on a computing device 3206 that includes one or more FPGAs 3208, waveform processing functionality may be performed by the FPGA(s) 3208 in addition to or in lieu of the processor 3204 of the computing device 3206 performing such functionality.

As described herein, aspects of the present disclosure provide for integration of ultrasonic transducer elements with circuitry on a single chip. The ultrasonic transducer elements may be used for ultrasound imaging applications, HIFU, or both. It should be appreciated that such elements may operate at voltages higher than those conventionally used for CMOS integrated circuitry, e.g., higher than voltages typically supported by deep submicron CMOS circuitry. For example, such ultrasonic transducer elements may operate at voltages between 20 V and 120 V, between 30 V and 80 V, between 40 V and 60 V, at any voltage within those ranges, or at any other suitable voltages. HIFU applications may utilize higher voltages than ultrasound imaging applications.

Thus, integration of ultrasonic transducer elements with circuitry on a single chip may be facilitated by making such circuitry compatible with higher voltages than traditionally used for CMOS integrated circuitry, i.e., by operating standard CMOS deep submicron circuitry at higher than customary voltages.

There are two main issues that can limit the operating voltage of NMOS and PMOS devices in CMOS circuits: (1) gate oxide breakdown, and (2) source and drain (diffusion) breakdown. In many designs, diffusion breakdown is the first limitation, in that the diffusion is specifically engineered in field effect transistors (FETs) to break down before the gate oxide so as to protect the gate oxide. To increase the diffusion breakdown voltage, the relative concentrations in the source/drain regions to the substrate should be adequate. In some embodiments, lower doping levels in the source and drain regions may increase breakdown voltage.

With respect to gate oxide breakdown, an excessive electric field may stress the gate oxide, leading to rupture or gate leakage current. To increase the gate-to-drain or gate-to-source breakdown voltage, the maximum electric field should be reduced.

Various methods can be used to make high-voltage CMOS circuits. Such methods may, for example, be implemented at the level of mask logic operations and device layout. The standard diffusion junction in NMOS technologies is N+ degenerately doped to P-well retrograde doped typically on the order of $10^{17}$ to $10^{18}$ dopants/cm$^3$. A 3V device typically breaks down at 6 volts. The source and drain may, for example, be defined by the same implant that dopes the poly-Si gate. This is generally called a self-aligned transistor.

The standard gate-to-drain interface is a Lightly Doped Drain (LDD). The LDD may, for example, be doped to reduce the electric field but may be minimized in size in order to keep device length large enough to maintain gate control.

CMOS circuitry may, for example, be turned into high-voltage CMOS circuitry by changing the diffusion scheme. For example, a mask-aligned source and drain using N-well and P-well regions may be employed. For NMOS implementations, the diffusion may be changed to N-well source/drain with P-substrate. For PMOS, the diffusion may be changed to P-well source/drain regions with N-Well and Deep N-well. The source and drains may be defined by Shallow Trench Isolation (STI). Alternatively, for larger voltages, the source and drains may be defined by gap space and thermal diffusion.

Examples of circuit layouts and associated structures that may be used to implement high-voltage CMOS circuits in the various embodiments set forth in this disclosure are shown in FIGS. 33-42.

Figure 33:
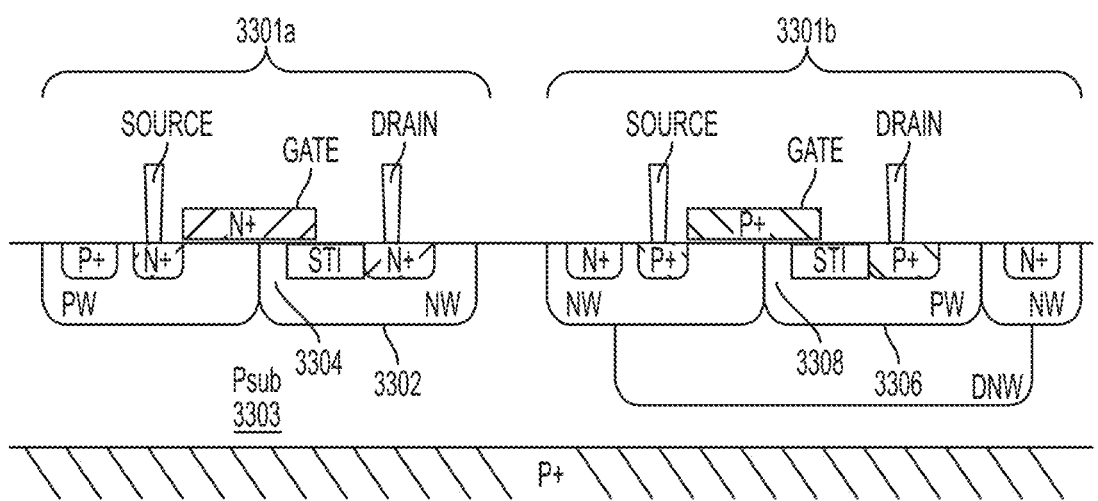
FIG. 33 shows an example of a high voltage NMOS and PMOS layout that may be used in some embodiments.

FIG. 33 shows an example of a high voltage NMOS 3301a and PMOS 3301b layout that may be used in some embodiments, for example to provide high voltages a deep submicron nodes. The reference numerals set forth in FIG. 33 correspond to the following features and/or characteristics of the illustrated layout: 3302—Large junction breakdown due to N-well (NW)/P-substrate (Psub 3303); 3304—Reduced E-field due to LDD; 3306—Large junction breakdown due to P-well (PW)/NW; and 3308—Reduced E-field due to LDD.

Figure 34:
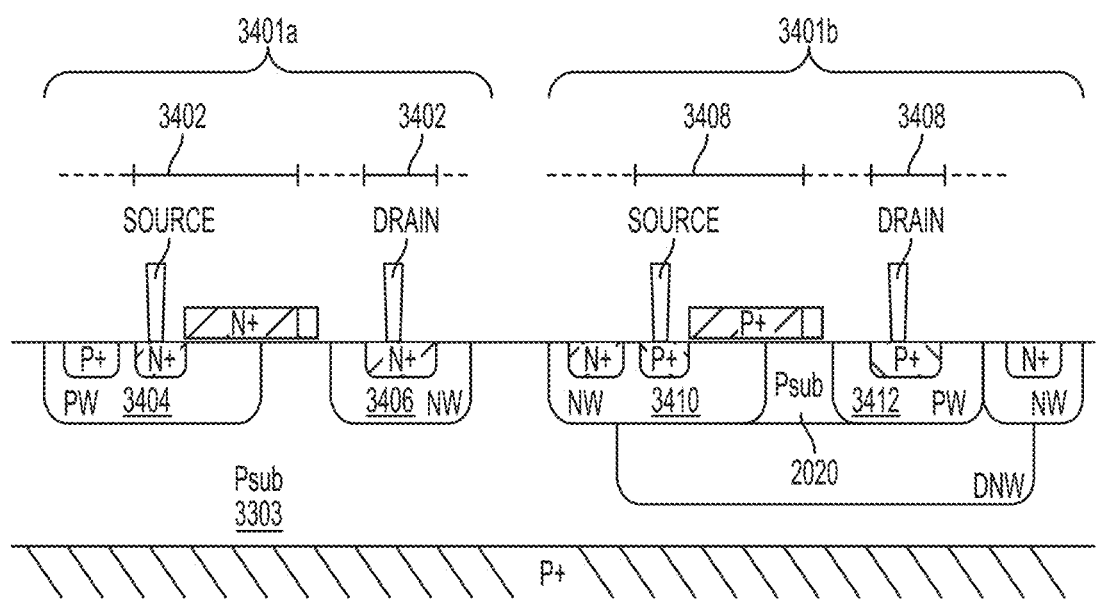
FIG. 34 shows an example of a very high voltage NMOS and PMOS layout that may be used in some embodiments.

FIG. 34 shows an example of a very high voltage NMOS 3401a and PMOS 3401b layout that may be used in some embodiments. The reference numerals set forth in FIG. 34 correspond to the following features and/or characteristics of the illustrated layout: 3402—Mask defined doping for N+ implant; 3404—Thermally diffused PW/Psub; 3406—Thermally diffused NW/Psub; 3408—Mask defined doping for P+ implant; 3410—Thermally diffused NW/Psub; and 3412—Thermally diffused PW/Psub.

Figure 35:
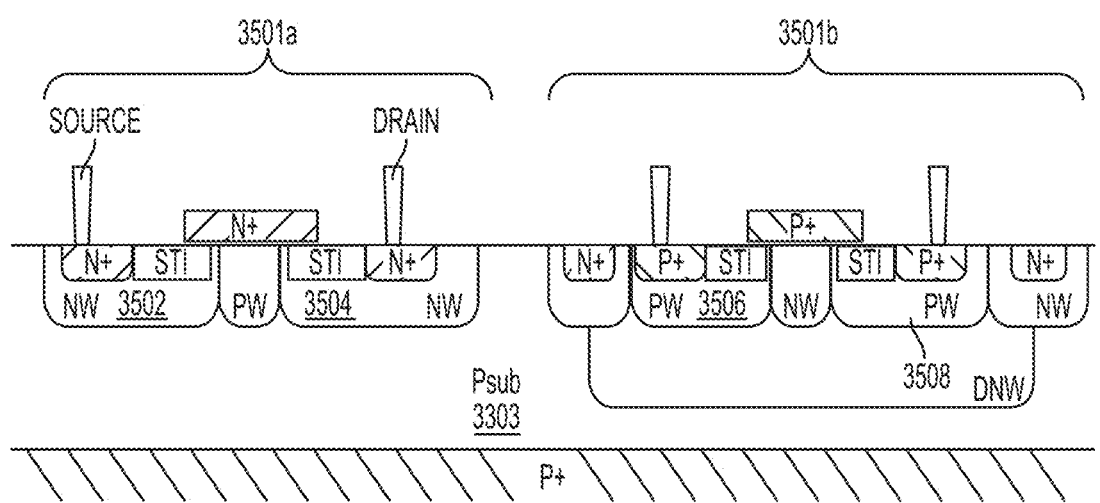
FIG. 35 shows an example of a high voltage NMOS and PMOS bidirectional or cascoding layout that may be used in some embodiments.

FIG. 35 shows an example of a high voltage NMOS 3501a and PMOS 3501b bidirectional or cascoding layout that may be used in some embodiments. The reference numerals set forth in FIG. 35 correspond to the following features and/or characteristics of the illustrated layout: 3502—N-well source and source gate extension; 3504—N-well drain and gate extension; 3506—P-Well source and source gate extension; and 3508—P-well drain and gate extension.

Figure 36:
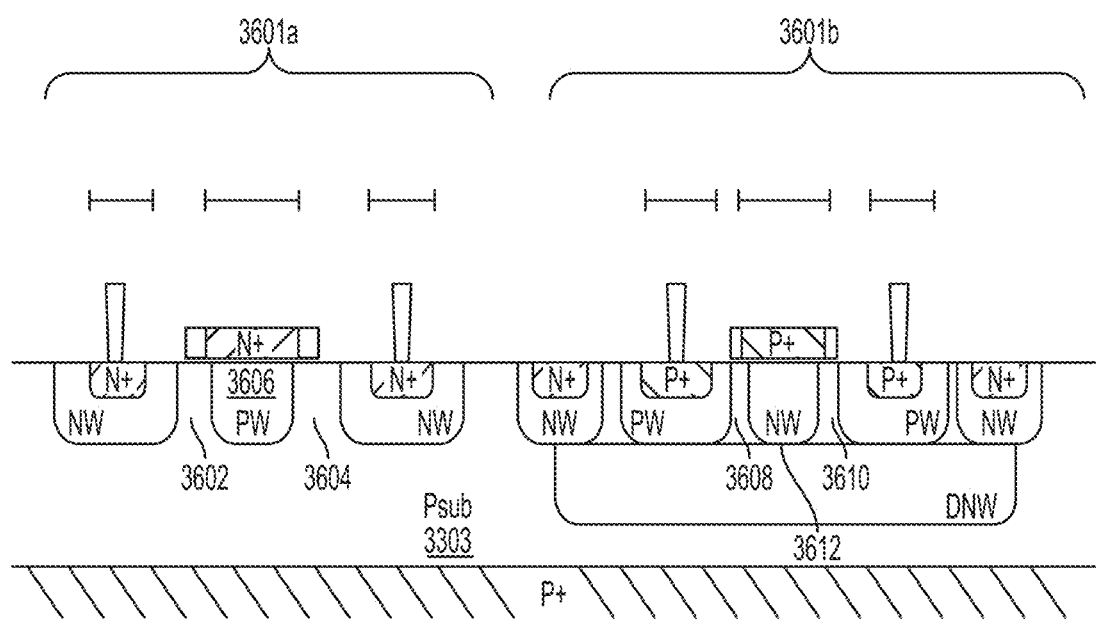
FIG. 36 shows an example of a very high voltage NMOS and PMOS bidirectional or cascoding layout that may be used in some embodiments.

FIG. 36 shows an example of a very high voltage NMOS 3601a and PMOS 3601b bidirectional or cascoding layout that may be used in some embodiments. The reference numerals set forth in FIG. 36 correspond to the following features and/or characteristics of the illustrated layout: 3602, 3604—Thermally diffused source and drain in Psub; 3606—Optional P-well gate implant for threshold increase; 3608, 3610—Thermally diffused source and drain in Psub; and 3612—Optional N-well gate implant for threshold increase.

Figure 37:
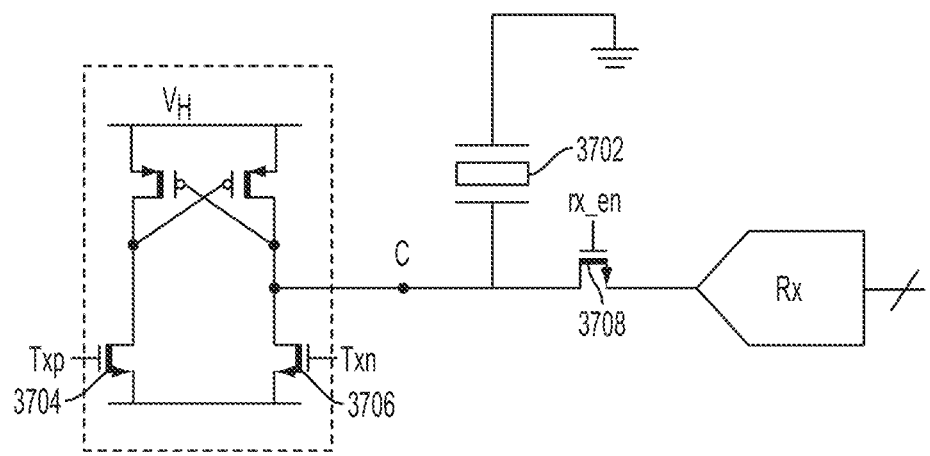
FIG. 37 shows an example of a pulser using a high voltage NMOS and PMOS layout with a high voltage switch that may be used in some embodiments.

FIG. 37 shows an example of a pulser using a high voltage NMOS and PMOS layout with a high voltage switch that may be used in some embodiments. The reference numerals set forth in FIG. 37 correspond to the following features and/or characteristics of the illustrated layout: 3702—CUT; 3704 and 3706 represent transistor switches. To disable the pulser, set Txp=0, Txn=1, and then set Txn=0 (PMOS will hold state as long as c node stays within low voltage rails). 3708 represents an Enable switch for receive an enable signal rx_en to isolate from high voltage. The transistors may have thick channels as illustrated by the thick gate lines in the figure, which signifies a high voltage (HV) device.

Figure 38A:
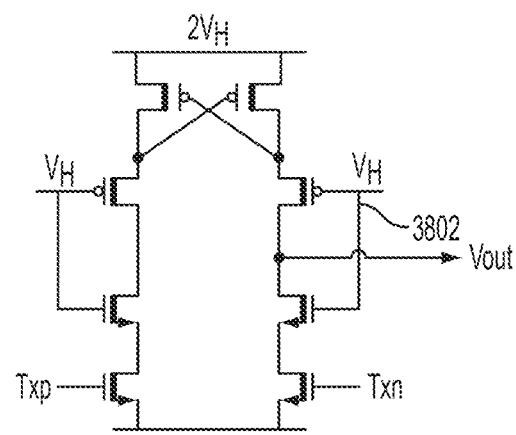
FIGS. 38A and 38B show examples of double and quadruple voltage pulse drivers, respectively, that may be used in some embodiments.
Figure 38B:
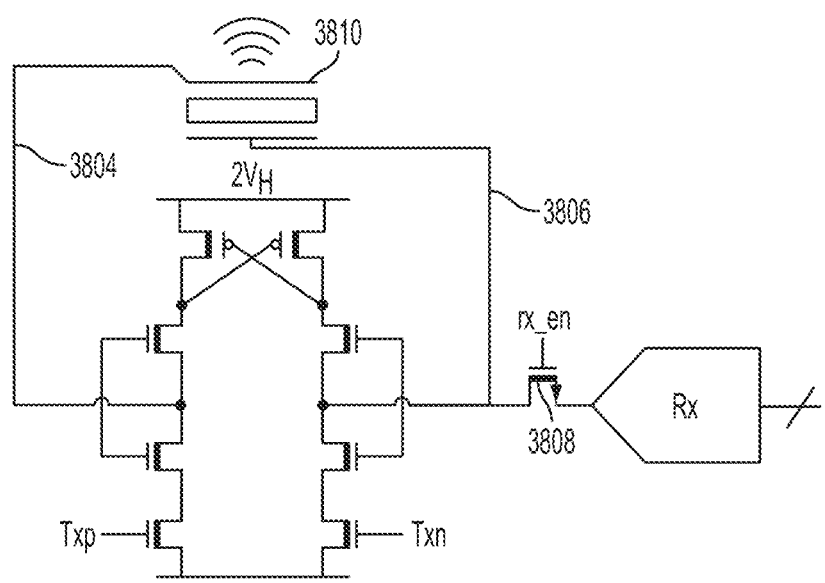

FIGS. 38A and 38B show examples of a double and quadruple voltage pulse drivers, respectively, that may be used in some embodiments. The reference numerals set forth in FIGS. 38A and 38B correspond to the following features and/or characteristics of the illustrated layout: 3802—Added cascading devices; 3804, 3806—terminals of a transducer element to be driven with an H-bridge circuit; 3808—a receive element. In operation, turn on the switch in receive mode (set Txn=1, Txp=0, and then set Txn=0); 3810—Top plate of transducer, which is automatically biased in Receive.

Figure 39A:
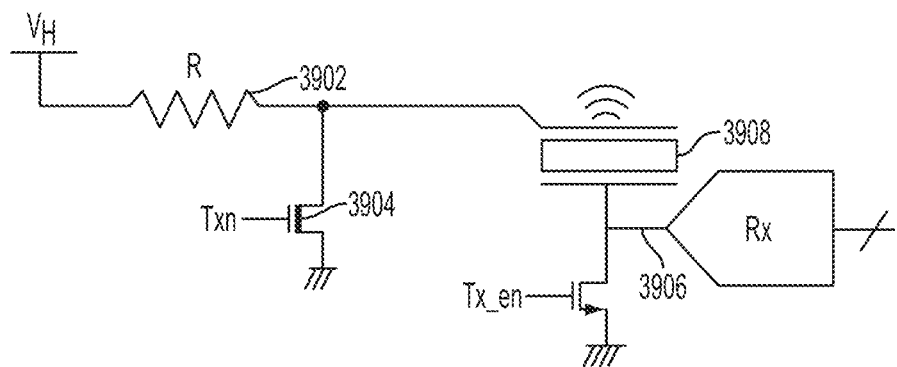
FIGS. 39A-B show an example of a pulser that does not employ a receive isolation switch, which may be used in some embodiments.
Figure 39B:
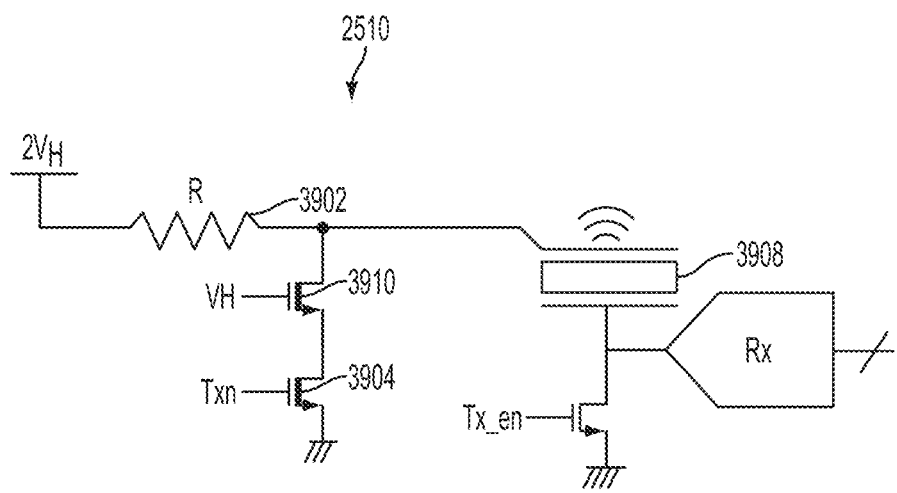

FIGS. 39A-B show an example of a pulser that does not employ a receive isolation switch, which may be used in some embodiments. The reference numerals set forth in FIG. 39A-B correspond to the following features and/or characteristics of the illustrated layout: 3902—Resistor defined by N-well in Psub or by nonsilicided polysilicon on FOX; 3904—High-voltage NMOS pull down device; 3906—Direct connection to RX (no switch yields less parasitics); 3908—Automatic receive bias; and 3910—Cascode device for double voltage.

Figure 40A:
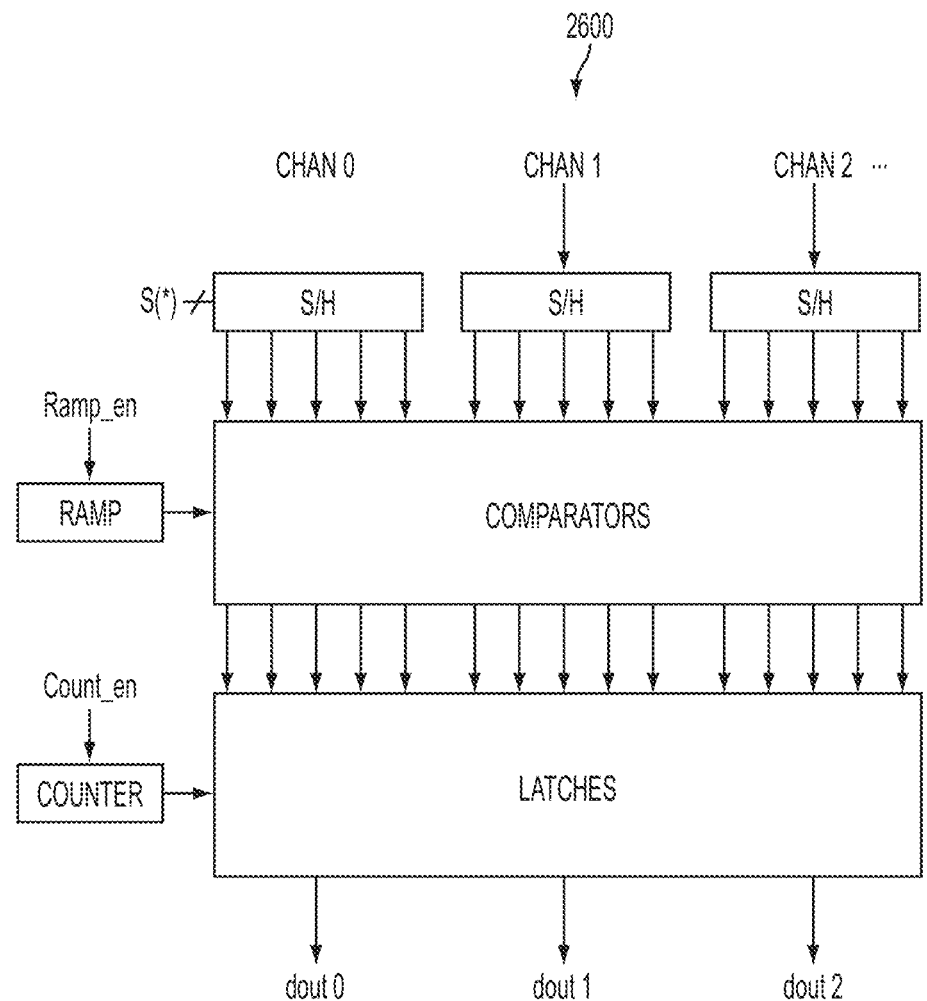
FIGS. 40A and 40B show an example of a time-interleaved single slope analog-to-digital converter (ADC) and the operation thereof, respectively, that, in some embodiments, may be employed as one or more of the ADCs reference herein.
Figure 40B:
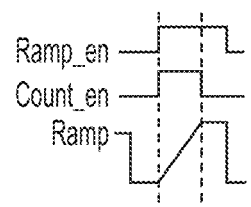

FIGS. 40A and 40B show an example of a time-interleaved single slope ADC and the operation thereof, respectively, that, in some embodiments, may be employed as one or more of the ADCs reference herein. In the illustrated example, N parallel ADCs are used for one channel to take alternating samples such that the sampling frequency of each ADC is much lower than the Nyquist criterion. Such single slope ADCs may, for example, allow large-scale sharing of resources: bias, ramp, and gray counter. Such an ADC approach may thus provide a highly scalable, low power option.

Figure 41:
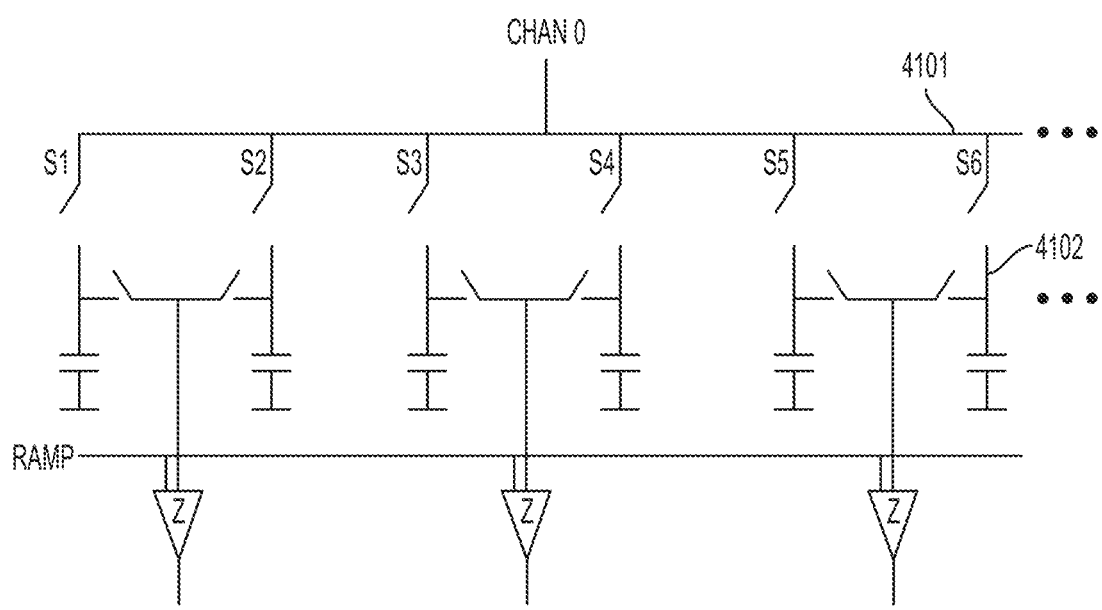
FIG. 41 shows an example of a time interleaved sample and hold circuit that may be employed in some embodiments.

FIG. 41 shows an example of a time interleaved sample and hold circuit that may be employed in some embodiments. In the example shown, reference numeral 4102 signifies a step during which evens are sampled, and then odds are sampled, and reference numeral 4104 signifies a step during which the odds are compared, and then the evens are compared.

Figure 42A:
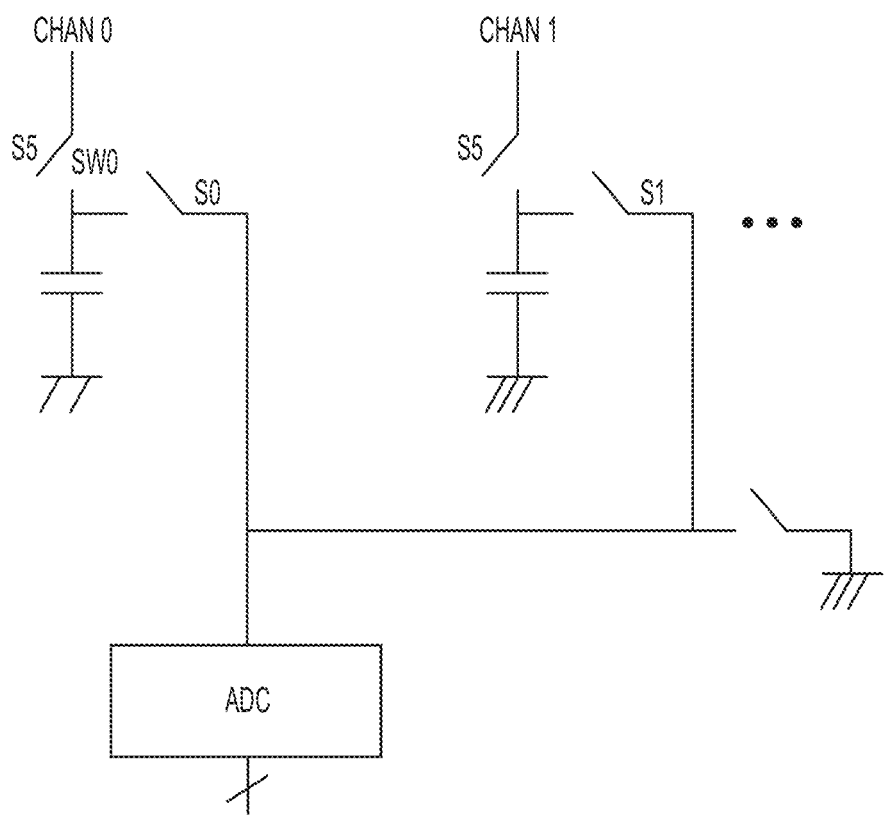
FIGS. 42A and 42B show an example of a time shared high speed ADC and the operation thereof, respectively, that, in some embodiments, may be employed as one or more of the ADCs referenced herein.
Figure 42B:
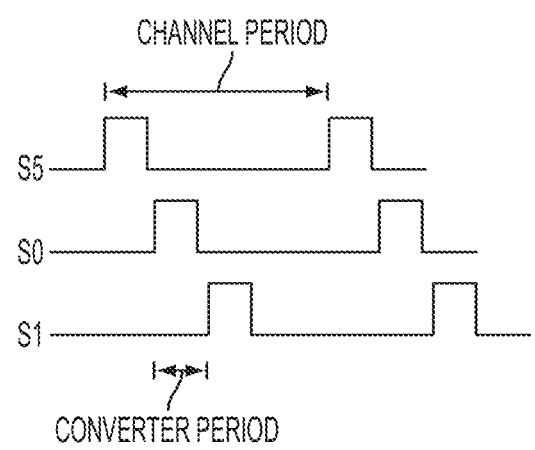

FIGS. 42A and 42B show an example of a time shared high speed ADC and the operation thereof, respectively, that, in some embodiments, may be employed as one or more of the ADCs referenced herein. Such an ADC may, for example, employ a pipelined, SAR, or flash architecture. Because a single high speed ADC having such an architecture may be used to sample N channels, such an ADC approach may significantly reduce area requirements.

The high voltage CMOS circuitry described herein may be configured to drive voltages higher than those conventionally attainable with CMOS circuitry, and to provide high voltages at deep submicron nodes. In some embodiments, voltages up to approximately 10 V may be handled or driven, up to approximately 20 V may be handled or driven, up to approximately 30 V may be handled or drive, up to approximately 40 V may be handled or driven, up to approximately 50 V may be handled or driven, up to approximately 60 V may be handled or driven, any voltage within those ranges, or other suitable voltages, as non-limiting examples.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A hand-held ultrasound device for placement on a subject, the hand-held ultrasound device comprising:
    a semiconductor device including:
        a plurality of ultrasonic transducer elements;
        a plurality of pulsers coupled to the plurality of ultrasonic transducer elements; and
        a plurality of waveform generators configured to drive the plurality of pulsers;
        receive processing circuitry configured to process ultrasound signals received by the plurality of ultrasonic transducer elements; and
        a plurality of independently controllable registers configured to store a plurality of different parameters for the waveform generators; and
    a housing to support the semiconductor device.

2. The hand-held ultrasound device of claim 1, wherein the plurality of ultrasonic transducer elements comprise independently controllable ultrasonic transducer elements disposed on a semiconductor substrate of the semiconductor device.

3. The hand-held ultrasound device of claim 1, wherein the plurality of ultrasonic transducer elements comprise capacitive micromachined ultrasonic transducers (CMUTs).

4. The hand-held ultrasound device of claim 1, wherein the housing comprises a hand-held housing in which the semiconductor device is disposed.

5. The hand-held ultrasound device of claim 1, wherein the plurality of waveform generators are configured to independently control the plurality of ultrasonic transducer elements.

6. The hand-held ultrasound device of claim 1, wherein a first independently controllable register of the plurality of independently controllable registers is configured to store a signal sampling event control parameter for sampling ultrasound signals received by the plurality of ultrasonic transducer elements.

7. The hand-held ultrasound device of claim 1, wherein a first independently controllable register of the plurality of independently controllable registers is configured to store a phase of an ultrasound waveform generated by the plurality of waveform generators.

8. The hand-held ultrasound device of claim 1, wherein a first independently controllable register of the plurality of independently controllable registers is configured to store a frequency of an ultrasound waveform generated by the plurality of waveform generators.

9. The hand-held ultrasound device of claim 1, wherein the plurality of ultrasonic transducer elements comprises a first ultrasonic transducer element having at least one first capacitive micromachined ultrasonic transducer (CMUT) and a second ultrasonic transducer element having at least one second CMUT,
a first waveform generator of the plurality of waveform generators is coupled to the first ultrasonic transducer element and configured to provide a first ultrasound waveform to the first CMUT, and
a second waveform generator of the plurality of waveform generators is coupled to the second ultrasonic transducer element and configured to provide a second ultrasound waveform to the second CMUT.

10. The hand-held ultrasound device of claim 1, further comprising a controller configured to control values stored by the plurality of independently controllable registers.

11. The hand-held ultrasound device of claim 10, wherein the semiconductor device further includes:
   a first analog-to-digital converter (ADC) forming part of the receive processing circuitry and coupled to a first ultrasonic transducer element of the plurality of ultrasonic transducer elements and configured to convert an analog signal provided by the first ultrasonic transducer element into a digital signal;
   a second ADC forming part of the receive processing circuitry and coupled to a second ultrasonic transducer element of the plurality of ultrasonic transducer elements and configured to convert an analog signal provided by the second ultrasonic transducer element into a digital signal; and
   a serial data output port configured to communicate a digital stream of data that includes the digital signals from the first and second ADCs from the handheld ultrasound device to an external device.

12. The hand-held ultrasound device of claim 11, wherein the semiconductor device comprises a first chip, and wherein the hand-held ultrasound device further comprises a second chip disposed within the housing, the second chip comprising digital processing circuitry forming part of the receive processing circuitry and electrically coupled to the serial data output port.

13. The hand-held ultrasound device of claim 10, wherein a first independently controllable register of the plurality of independently controllable registers of the first and second waveform generators is configured to store a phase.

14. The hand-held ultrasound device of claim 10, wherein a first independently controllable register of the plurality of independently controllable registers of the first and second waveform generators is configured to store a frequency.

15. The hand-held ultrasound device of claim 1, wherein the plurality of independently controllable registers are configured to store a plurality of different parameters for the receive processing circuitry.

16. A hand-held ultrasound device for placement on a subject, the hand-held ultrasound device comprising:
   a semiconductor device including:
      a plurality of ultrasonic transducer elements;
      a plurality of pulsers coupled to the plurality of ultrasonic transducer elements; and
      a plurality of waveform generators configured to drive the plurality of pulsers;
      receive processing circuitry configured to process ultrasound signals received by the plurality of ultrasonic transducer elements; and
      a plurality of independently controllable registers configured to store a plurality of different parameters for the waveform generators; and
   a housing to support the semiconductor device, wherein the plurality of ultrasonic transducer elements comprises a first ultrasonic transducer element and a second ultrasonic transducer element,
   the plurality of pulsers comprises:
      a first pulser coupled to the first ultrasonic transducer element so that the first ultrasonic transducer element emits an ultrasonic pulse; and
      a second pulser coupled to the second ultrasonic transducer element so that the second ultrasonic transducer element emits an ultrasonic pulse,
      a first waveform generator of the plurality of waveform generators is coupled to the first pulser to provide a first waveform to the first pulser in response to receipt, by a first transmit control circuit of the semiconductor device, of a transmit enable signal,
      a second waveform generator of the plurality of waveform generators is coupled to the second pulser to provide a second waveform to the second pulser in response to receipt, by a second transmit control circuit of the semiconductor device, of the transmit enable signal; and
   the semiconductor device further includes:
      at least one first delay component that impacts a length of a first delay between when the first transmit control circuit receives the transmit enable signal and when the first waveform is applied to the first pulser; and
      at least one second delay component that impacts a length of a second delay between when the second transmit control circuit receives the transmit enable signal and when the second waveform is applied to the second pulser,
      wherein the at least one first delay component is configured differently than the at least one second delay component, so that the length of the second delay is different than the length of the first delay.

17. The hand-held ultrasound device of claim 16, wherein the first ultrasonic transducer element comprises a capacitive micromachined ultrasonic transducer (CMUT).

18. The hand-held ultrasound device of claim 16, wherein the first pulser is a tri-level pulser.

19. The hand-held ultrasound device of claim 16, wherein the first pulser is configured to control the first ultrasonic transducer element to apply a pulse as part of high intensity focused ultrasound (HIFU).

20. The hand-held ultrasound device of claim 16, wherein the plurality of independently controllable registers are configured to store a plurality of different parameters for the receive processing circuitry.

* * * * *